US007368577B2

(12) United States Patent
Assaf et al.

(10) Patent No.: US 7,368,577 B2
(45) Date of Patent: *May 6, 2008

(54) THIAZOLE-BASED NITRIC OXIDE DONORS HAVING ARYL SUBSTITUENT(S) AND USES THEREOF

(75) Inventors: Peter Assaf, Kfar-Miilya (IL); Elham Gazaleen-Mariee, Yaffia (IL); Michael Naveh, Ramat-HaSharon (IL)

(73) Assignee: Renopharm Ltd., Nazareth (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/266,431

(22) Filed: Nov. 4, 2005

(65) Prior Publication Data

US 2006/0183718 A1 Aug. 17, 2006

Related U.S. Application Data

(63) Continuation of application No. PCT/IL2005/000481, filed on May 5, 2005.

(60) Provisional application No. 60/651,619, filed on Feb. 11, 2005, provisional application No. 60/567,824, filed on May 5, 2004.

(51) Int. Cl.
*A61K 31/426* (2006.01)
*C07D 277/28* (2006.01)

(52) U.S. Cl. ...................... 548/205; 514/365
(58) Field of Classification Search ................ 548/205
See application file for complete search history.

(56) References Cited

U.S. PATENT DOCUMENTS

| 4,505,857 | A | * | 3/1985 | Egli ........................... 534/768 |
| 4,923,886 | A | * | 5/1990 | Shiokawa et al. .......... 514/365 |
| 5,404,871 | A | | 4/1995 | Goodman et al. |
| 5,542,410 | A | | 8/1996 | Goodman et al. |
| 5,807,847 | A | | 9/1998 | Thatcher et al. |
| 5,874,063 | A | | 2/1999 | Briggner et al. |
| 5,883,122 | A | | 3/1999 | Thatcher et al. |
| 5,983,956 | A | | 11/1999 | Trofast |
| 6,221,398 | B1 | | 4/2001 | Jakupovic et al. |
| 6,268,533 | B1 | | 7/2001 | Gao et al. |
| 6,310,052 | B1 | | 10/2001 | Thatcher et al. |
| 6,566,324 | B2 | | 5/2003 | Nadel et al. |
| 6,571,790 | B1 | | 6/2003 | Weinstein |
| 6,637,430 | B1 | | 10/2003 | Voges et al. |
| 6,652,323 | B2 | | 11/2003 | Yanda |
| 6,916,835 | B2 | | 7/2005 | Thatcher et al. |
| 2002/0177622 | A1 | | 11/2002 | Thatcher et al. |
| 2005/0137191 | A1 | | 6/2005 | Thatcher et al. |

FOREIGN PATENT DOCUMENTS

| EP | 452782 A1 * | 10/1991 |
| WO | WO 99/55319 | 4/1999 |
| WO | WO 00/30614 | 2/2000 |
| WO | WO 01/49275 | 7/2001 |
| WO | WO 03/086282 | 10/2003 |

OTHER PUBLICATIONS

U.S. Appl. No. 09/473,713, filed Dec. 29, 1999, Thatcher et al.
Kumar et al. "Design, Synthesis, and Evaluation of α-Ketoheterocycles as Class C β-Lactamase Inhibitors", Bioorganic & Medicinal Chemistry, 9: 2035-2044, 2001.
Cavicchi et al. "Inhibition of Inducible Nitric Oxide Synthase in the Human Intestinal Epithelial Cell Line, DLD-1, by the Inducers of Heme Oxygenase 1, Bismuth Salts, Heme, and Nitric Oxide Donors", GUT, 47(6): 771-778, 2000. Abstract.
Salas et al. "Nitric Oxide Supplementation Ameliorates Dextran Sulfate Sodium-Induced Colitis in Mice", Laboratory Investigation, 82(5): 597-607, 2002. Abstract, p. 602, Col. 1, Lines 3-19.
Ueda et al. "Structure-Activity Relationships of 2-Aminothiazole Derivatives as Inducible Nitric Oxide Synthase Inhibitor", Chemical & Pharmaceutical Bulletin, 52(5): 634-637, 2004. Abstract, p. 634, col. 2, Last Line—p. 635, col. 1, Line 2, Table 2, Expls. 5a, 5b, 7, p. 636, col. 1, Lines 17-18, 25-39.
Münzel et al. "Evidence fpr Enhanced Vascular Superpxide Anion Production", The Journal of Clinical Investigation, 95: 187-194, 1995.
Chung et al. Identification of the Subcellular Site for Nitroglycerin Metabolism to Nitric Oxide in Bovine Coronary Smoth Muscle Cells, The Journal of Pharmacology and Experimental Therapeutics, 253(2): 614-619, 1990.
McGuire et al. "Inhibition of NADPH-Cytochrome P450 Reductase and Glyceryl Trinitrate Biotransformation by Diphenyleneidononium Sulfate", Biochemical Pharmacology, 56: 881-893, 1998.
Needleman et al. "Sulfhydryl Requirement for Relaxation of Vascular Smooth Muscle", The Journal of Pharmacology and Experimental Therapeutics, 187(2): 324-331, 1973.
Bueb et al. "Natural Polyamines Stimulate G-Proteins", Biochemical Journal, 282: 545-550, 1992.
Loscalzo "N-Acetylcysteine Potentiates Inhibition of Platelet Aggregation by Nitroglycerin", Journal of Clinical Investigation, 76: 703-708, 1985.
Kurz et al. "Nitroglycerin Metabolism in Vascular Tissue: Role of Glutathione S-Transferases and Relationship Between NO and NO2-Formation", Biochemical Journal, 292: 545-550, 1993.

* cited by examiner

*Primary Examiner*—Laura L. Stockton

(57) ABSTRACT

Disclosed are novel NO-donating compounds, designed such that when NO is released from the compound a residue which is a naturally occurring metabolite is formed, and thus a development of tolerance to the compounds upon repetitive administration is prevented or decreased. Also disclosed are methods of preparing such NO-donating compounds, pharmaceutical compositions and medical devices containing such compounds and methods utilizing such compounds in the treatment of various medical conditions.

4 Claims, 22 Drawing Sheets

US 7,368,577 B2

THIAZOLE-BASED NITRIC OXIDE DONORS HAVING ARYL SUBSTITUENT(S) AND USES THEREOF

RELATED APPLICATIONS

The present application is a Continuation of PCT Application No. PCT/IL2005/000481, filed on May 5, 2005, which claims priority from U.S. Provisional Application No. 60/567,824, filed on May 5, 2004 and from U.S. Provisional Patent Application No. 60/651,619, filed on Feb. 11, 2005. The contents of each of the above applications are incorporated herein by reference.

FIELD AND BACKGROUND OF THE INVENTION

The present invention relates to novel, non-tolerance inducing, NO-donating compounds and their use in the treatment of various disorders and diseases such as, for example, cardiovascular diseases, inflammation, tumor suppression and psychiatric and neurological diseases.

Nitric oxide (NO) mediates multiple physiological and pathophysiological processes in the cardiovascular and neurological systems.

Biological NO is synthesized by the enzyme nitric oxide synthase (NOS) that generates NO from L-arginine. This enzyme exists in three different forms (referred to as isoforms), NOS-1, NOS-2 and NOS-3. Each isoform generates NO under different conditions. NOS-1 is the neural isoform (also known as the brain isoform) and is a key component in synaptic transmission. NOS-2 (also known as inducible NOS is responsible for generating high concentrations of NO (100 to 1000 folds higher then the normal NO biological concentration), typically in response to the presence of bacteria. NOS-2 is produced by macrophages and is responsible for their effects to repair injury and warding off infections. NOS-3 (also known as endothelial NOS or eNOS) is found in endothelial cells lining the inner surface of all blood vessels and lymph ducts. eNOS is activated by the pulsatile flow of blood through vessels, which exerts "shear stress" on the membrane of the endothelial cells. The NO generated by eNOS is responsibly for maintaining the diameter of blood vessels, to thereby maintain an optimal level of tissues perfusion, as well as for the growth of new blood vessels (angiogenesis).

Pharmacological compounds that release NO (also known as NO-donors) have been useful tools for evaluating the pivotal role of NO in physiology and therapeutics. These agents constitute two broad classes of compounds, those that release NO or one of its redox congeners spontaneously, and those that require enzymatic metabolism to generate NO. Several commonly used cardiovascular drugs exert their beneficial action, in part, by modulating the NO pathway.

Dysfunction of the normally protective endothelium is found in several cardiovascular diseases, including atherosclerosis, hypertension, heart failure, coronary heart disease, arterial thrombotic disorders and stroke. Endothelial dysfunction leads to nitric oxide (NO) deficiency, which has been implicated in the underlying pathobiology of many of these disorders (NO insufficiency states) [Loscalzo J. and Vita J., Nitric Oxide and the Cardiovascular System. Totawa, N.J.: Humana Press; 2000]. NO insufficiency may reflect an absolute deficit of NO (synthesis), impaired availability of bioactive NO, or enhanced NO inactivation. Whatever its biochemical basis, NO insufficiency limits NO-mediated signal transduction of normal or protective physiological processes. In light of this pathobiology, replacement or augmentation of endogenous NO by exogenously administered NO donors has provided the foundation for a broad field of pharmacotherapeutics in cardiovascular and neurological medicine.

The beneficial effects of nitric oxide (NO) as a therapeutic agent in general, and as a blood vessel dilator (vasodilator) in particular, was first observed in 1857, and demonstrated by the therapeutic activity of a family of compounds, known as nitrovasodilators, that have been used purposely for almost 150 years.

While NO was originally described as a potent vasodilator [ISIS-4, Lancet. 1995; 345: 669-685 and Brunton T L, Lancet. 1867; 2: 97-98], it is now also recognized as a protecting agent against thrombosis and atherogenesis through inhibition of monocyte and platelet adhesion [Murrell W, Lancet. 1879; 1: 80-81, 11-15, 151-152, 224-227, 642-646], platelet aggregation [Chung S-J et al., J Pharmacol Exp Ther. 1990; 253: 614-619] and smooth muscle cell proliferation [McGuire J J et al., Biochem Pharmacol. 1998; 56: 881-893].

Dysfunction in NO synthesis has been implicated as a major contributory factor in development of a wide range of cardiovascular diseases including hypertension [Kurz M A et al., Biochem J. 1993; 292: 545-550 and Needleman P et al., J Pharmacol Exp Ther. 1973; 187: 324-33 1], coronary artery disease and heart failure [Loscalzo J, J Clin Invest. 1985; 76: 703-708 and Munzel T et al., J Clin Invest. 1995; 95: 187-194]. The detrimental effects of reduced NO synthesis, as a result of enzyme dysfunction or endothelial damage, are often exacerbated in cardiovascular disease by increased generation of oxygen free radicals which rapidly inactivate NO [Munzel T et al., J Clin Invest. 1996; 98: 1465-1470] forming cytotoxic peroxynitrite and, ultimately, inactive nitrate. Thus, delivery of supplementary NO to areas of the vasculature where the protective effects of endogenous NO have been adversely affected is an attractive therapeutic option.

It is now well established that NO is an important bioregulator, involved not only in blood clotting and blood pressure, but also in the control of neurotransmission, and possibly the destruction of cancerous tumor cells [Evig, C B. et al., Nitric Oxide, 2004, 10(3), 119-29]. NO was found to affect neurotransmission, both directly and indirectly. NO is known to affect the cGMP level and hence promotes phosphorylation of ion channels, especially potassium channels, which are necessary for normal transmission of nerve signals. As it affects the blood flow, NO further promotes the transportation of oxygen and glucose to nerve cells, and thus promotes ATP production and hence potassium/sodium homeostasis which is essential for neurotransmission. Moreover, recent studies have linked NO to psychiatric and neurological diseases, and suggest the augmentation of brain NO-levels as a treatment of brain diseases characterized by excessive activity of brain dopamine systems and/or nitric oxide systems (Brain Research Bulletin, 1996, Vol. 40, No. 2, pp. 121-127, Molecular and Chemical Neuropathology, 1996, Vol. 27, Humana Press, Inc. 1044-7393/96/2703-0275 and Schizophrenia Research, 1995, 15(1, 2): 65).

While NO is a gas, it may be directly administered by inhalation. However, although this administration route is used in cases where improved patient oxygenation is required, as, for example, in pulmonary hypertension (high blood pressure in the lungs) and in patients with sickle cell anemia, such direct administration of the NO active form may not reach the target organ and/or biological system, and is oftentimes associated with both biochemical and medical complications, including, for example, methemoglobinemia and direct pulmonary injury.

In a search for alternative routes for administering NO, it was found that NO may be delivered and generated in situ by means of prodrugs. These prodrugs are known as NO-donors, which are metabolized by means of an enzymatic mechanism so as to generate or release active NO.

NO-donors, which are also referred to interchangeably, herein and in the art, as NO prodrugs or NO-donating agents) are pharmacologically active substances that spontaneously release, or are metabolized to, NO or its redox congeners.

Organic nitrate esters represent a class of NO-donating agents used in cardiovascular therapeutics since the nineteenth century. The preliminary reports of the clinical use of organic nitrates and nitrites were derived from the work of Brunton [*Lancet*. 1867; 2: 97-98] in 1867 and the seminal work of Murrell [*Lancet*. 1879; 1: 80-81, 11-15, 151-152, 224-227, 642-646] in 1879, which showed the clear benefits of nitroglycerin in the treatment of angina pectoris.

Additional examples of organic nitrate and nitrite esters NO-donors that act as nitrovasodilators include erythrityl tetranitrate, pentaerythritol tetranitrate, amyl nitrite, isosorbide dinitrate, isosorbide 5-mononitrate, and nicorandil. These compounds were found to have direct vasoactive effects and have been used for many years to treat ischemic heart disease, heart failure, hypertension and other cardiovascular diseases [Gruetter C A et al., *J Cyclic Nucleotide Res*. 1979; 5: 211-224, *J Pharmacol Exp Ther*. 1980; 214: 9-15, *J Pharmacol Exp Ther*. 1981; 219: 181-186 and ISIS-4, *Lancet*. 1995; 345: 669-685]. The principal action of these compounds involves vasorelaxation, mediated by guanylyl cyclase activation and by direct inhibition of nonspecific cation channels in vascular smooth muscle cells (VSMCs). As such, these agents represent the prototypical form of NO-replacement therapy.

The mechanism of action by which organic nitrate esters such as nitroglycerin generate bioactive NO typically involves enzymatic metabolism. Studies conducted in this respect suggested that nitroglycerin (glyceryl trinitrate; GTN) induces vasorelaxation by generating NO or a related S-nitrosothiol (SNO), which is formed by direct interactions of GTN with low-molecular-weight thiols [28], through an enzymatic system that is located within microsomal membranes, has an estimated apparent molecular mass of 160 kDa, and manifests enhanced activity in the presence of reducing equivalents, especially thiols [Chung S-J et al., *J Pharmacol Exp Ther*. 1990; 253: 614-619], which are known to potentiate the action of organic nitrate esters [Napoli C et al., *Nitric Oxide*. 2001; 5: 88-97 and Loscalzo J. et al., *J Clin Invest*. 1985; 76: 703-708].

Thus, it was found that NO and SNO activate the soluble target enzyme guanylyl cyclase (sGC), increasing tissue levels of the second messenger cGMP. A cGMP-dependent protein kinase I (cGK-I) mediates vasorelaxation by phosphorylating proteins that regulate intracellular Ca2+levels [Lincoln, T. M. et al., *J. Appl. Physiol*, 2001. 91:1421-1430]. However, it was further found that nitroglycerin could also dilate blood vessels through a cGMP-independent pathway [Chen, Z. et al., *Proc. Natl. Acad. Sci. U.S.A*. 2002, 99:8306-8311].

Other candidate enzymes that were suggested as being involved in NO metabolism includes glutathione S-transferases [Lau, D. T. et al., *Pharm. Res.,* 1992, 9:1460-1464], the cytochrome P-450 system in conjunction with NADPH and glutathione-S-transferase activities [McGuire J J, et al., *Biochem Pharmacol*. 1998; 56: 881-893, Kurz M A et al., *Biochem J*. 1993; 292: 545-550, McDonald, B. J. et al., *Biochem. Pharmacol.,* 1993, 45:268-270], xanthine oxido reductase [O'Byrne, S. et al., *J. Pharmacol. Exp. Ther.,* 2000, 292:326-330], and mitochondrial aldehyde dehydrogenase (ALDH-2) [Chen, Z. et al., *Proc. Natl. Acad. Sci. USA* 2002, 99: 8306-8311].

However, while the beneficial effects of administering NO-donors have been widely recognized, treatment with conventional nitrate preparations, as those described hereinabove, is typically limited by their therapeutic bioavailability half-life, lack of selectivity, systemic absorption accompanied by potentially adverse hemodynamic effects, and drug tolerance, with the latter being with the presently most limiting feature associated with administration of NO-donors [Ignarro L J. et al., *J Cardiovasc Pharmacol*. 1999; 34: 879-886, Kojda G. et al., *Cardiovasc Res*. 1999; 43: 562-571, Loscalzo J. et al., *Humana Press;* 2000, Loscalzo J. et al., *Circ Res*. 2001; 88: 756-762, Loscalzo J., *Circulation*. 2000; 101: 2126-2129 and Napoli C. et al., *Nitric Oxide*. 2001; 5: 88-97]. The inadequacies in current NO-donor prodrugs have limited their use to only short-term management of angina pectoris and acute heart failure.

Since drug-tolerance presently presents the most challenging limit for the clinical use of organic nitrite and nitrate esters, efforts have been made to study this phenomenon. Initially, it was hypothesized that tolerance was caused by abnormalities in the nitrate biotransformation process (also referred to in the art as mechanism-based or classical tolerance), but recent investigations associated it with increased angiotensin II-dependent vascular production of superoxide anion from NAD(P)H oxidase and endothelial NO synthase (eNOS) [Munzel T. et al., *J Clin Invest*. 1995; 95: 187-194 and Munzel T, Kurz S, Rajagopalan S, Thoenes M, Berrington W R, Thompson J A, Freeman B. et al., *J Clin Invest*. 1996; 98: 1465-1470]. The superoxide anion generated by these enzymes reacts with NO derived from the NO donor to form peroxynitrite ($OONO^-$), as indicated by the finding of increased urinary 3-nitrotyrosine in nitrate-tolerant patients [Skatchkov M. et al., *J Cardiovasc Pharmacol Ther*. 1997; 2: 85-96]. Moreover, it was found that nitrate tolerance is also associated with cross-tolerance to endothelium-derived NO [Molina C R. et al., *J Cardiovasc Pharmacol*. 1987; 10: 371-378], both by the oxidative inactivation of this endogenous NO to peroxynitrite and by the "uncoupling" of eNOS activity [Munzel T. et al., *Circ Res*. 2000; 86: E7-E12].

The mechanisms underlying this time- and dose-dependent tolerance phenomenon are probably multifactorial and may involve neurohormonal counter regulatory mechanisms (also known as pseudo tolerance) [Gori, T. et al., *Circulation*. 2002, 106:2404-2408], increases in activity of the phosphodiesterase 1A1 [Kim, D. et al., *Circulation*. 2001, 104:2338-2343], desensitization of the sGC [Artz, J. D. et al., *J. Biol. Chem*. 2002, 277:18253-18256], increases in production of reactive oxygen species (ROS) [Munzel, T. et al., *J. Clin. Invest*. 1995, 95:187-194], and impairment of GTN biotransformation (also known as mechanism-based or classical tolerance) [Chen, Z. et al., *Proc. Natl. Acad. Sci. USA* 2002, 99:8306-8311].

Most recently, Chen et al. [*Proc. Natl. Acad. Sci. USA* 2002, 99:8306-8311] demonstrated that the biotransformation of GTN is primarily induced by ALDH-2, which catalyzes the conversion of GTN to 1,2-glyceryl dinitrate (1,2-GDN) and nitrite within mitochondria. The study of Chen et al. demonstrated that inhibitors of ALDH-2 blocked the vasorelaxation by GTN, which is dependent on cGMP (cGMP-independent relaxation was still evident), both in vitro and in vivo, and furthermore, that treatment of vascular tissue with high concentrations of GTN resulted in both inhibition of ALDH-2 and a shift in the GTN dose response relationship. Thus, it appears that inhibition of ALDH-2 also underlies classical mechanism-based tolerance in vitro. Chen et al. speculated that build up of GTN and/or NO by-products in mitochondria may lead to mitochondrial damage and uncoupling of respiration, whereby increased production of superoxide and other ROS would in turn oxidize critical thiols, including active-site thiols in ALDH-2 [Steinmetz, C. G. et al., Structure. 1997, 5:701-711], further attenuating GTN-biotransformation. Superoxide also inactivates endothelium-dependent vasodilators (thereby reducing cGK-I activity). Thus, mitochondrial production of ROS would promote both mechanism-based tolerance and cross-tolerance.

While the extent to which ALDH-2 contributes to GTN tolerance (impaired relaxation to GTN) and cross-tolerance (e.g., impaired endothelium-dependent relaxation) in vivo remains to be elucidated, these studies clearly indicate that the present use of organic nitrates as NO-donors is highly limited.

In order to repress, reverse or prevent nitrate tolerance, several agents and metabolites, such as low molecular weight thiols, ascorbate, L-arginine, tetrahydrobiopterin, hydralazine, ACE (angiotensin converting enzyme) inhibitors, and folate, have been used [Juggi, J S. et al., Can J Cardiol, 1991, 9(7), 419-25].

As an alternative treatment, novel NO-donating drugs which may offer selective effects, a prolonged half-life, and a reduced incidence of drug tolerance are currently in various developmental stages. Among these are diazeniumdiolates, known as "NONOates" (1-substituted diazen-1-ium-1,2-diolates, e.g., DETA NONOate) [Keefer L K. et al., Methods Enzymol. 1996, 268, pp. 281-93], S-nitrosothiols (e.g., SNAP) [Ng E S, Kubes P, Can J Physiol Pharmacol. 2003, 81(8), pp. 759-64] and mesoionic oxatriazoles (e.g., GEA3162 or 1,2,3,4-oxatriazolium-5-amino-3-(3,4-dichlorophenyl)-chloride) [Karup G. et al., Pol J Pharmacol. 1994, 46(6), pp. 541-52]. However, heretofore these compounds are still in pre-clinical phases and are mostly used as biochemical and pharmacological tools In view of the limitations associated with utilizing the presently known NO-donors in modern armamentarium, there is a widely recognized need for, and it would be highly advantageous to have novel NO-donating compounds devoid of the above limitations.

SUMMARY OF THE INVENTION

According to one aspect of the present invention described hereinbelow, there is provided an NO-donating compound, and/or a pharmaceutically acceptable salt thereof, which includes an NO-releasing group and a chemical moiety being covalently attached to the NO-releasing group, such that when NO is released from the compound, a residue which is a naturally occurring metabolite is formed, thereby preventing or decreasing a development of tolerance to the NO-donating compound upon repetitive administration thereof.

According to further features in preferred embodiments of the invention described below, the NO-releasing group is selected from the group consisting of a —ONO$_2$ group, a —SNO group, a diazeniumdiolate and a mesoionic oxatriazole.

According to still further features in the described preferred embodiments the NO-donating compound further includes a bioactive agent residue, as described hereinbelow, covalently attached to the chemical moiety.

According to still further features in the described preferred embodiments the bioactive agent residue is attached to the chemical moiety via a biocleavable moiety, as described hereinbelow.

According to still further features in the described preferred embodiments the naturally occurring metabolite is a thiamine metabolite.

According to still further features in the described preferred embodiments the chemical moiety includes a substituted or unsubstituted thiazole ring.

According to still further features in the described preferred embodiments the NO-donating compound has the general formula I:

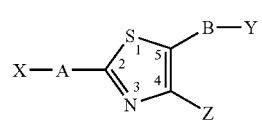

Formula I wherein:

A is selected from the group consisting of alkenyl, alkoxy, alkyl, alkynyl, amine, amine-oxide, aryl, aryloxy, azo, borate, C-amide, carbonyl, C-carboxylate, C-thiocarboxylate, cycloalkyl, diazo, disulfide, guanidine, guanyl, haloalkyl, heteroalicyclic, heteroaryl, hydrazine, N-amide, N-carbamate, N-dithiocarbamate, nitro, N-sulfonamide, N-thiocarbamate, O-carbamate, O-carboxylate, O-thiocarbamate, O-thiocarboxylate, oxime, oxygen, sulfur, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, sulfur, thioalkoxy, thioaryloxy, thiocarbonyl, thiophosphate, thiosulfate, thiosulfite, thiourea, triphosphate, urea, a biocleavable moiety and any combination thereof, or absent;

X is selected from the group consisting of acyl-halide, alkenyl, alkoxy, alkyl, alkynyl, amine, amine-oxide, aryl, aryloxy, azo, borate, C-amide, carbonyl, C-carboxylate, C-thiocarboxylate, cyano, cycloalkyl, diazo, disulfide, guanidine, guanyl, halide, haloalkyl, heteroalicyclic, heteroaryl, hydrazine, hydrogen, hydroxy, N-amide, N-carbamate, N-dithiocarbamate, nitro, N-sulfonamide, N-thiocarbamate, O-carbamate, O-carboxylate, O-thiocarbamate, O-thiocarboxylate, oxime, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, thioalkoxy, thioaryloxy, thiocarbonyl, thiohydroxy, thiophosphate, thiosulfate, thiosulfite, thiourea, triphosphate, urea, a bioactive agent residue as described herein, a moiety containing one or more NO-releasing group as described herein, a substituted or unsubstituted thiazole and any combination thereof;

B is selected from the group consisting of a saturated or unsaturated, substituted or unsubstituted alkylene chain having 1-20 carbon atoms, and a saturated or unsaturated, substituted or unsubstituted alkylene chain having 1-20 carbon atoms interrupted by one or more heteroatom, whereby the heteroatom or heteroatoms include oxygen, sulfur, nitrogen, phosphor, silicon and any combination thereof;

Y is the NO-releasing group; and

Z is selected from the group consisting of hydrogen, alkyl, alkenyl, alkynyl, amine, cycloalkyl, heteroalicyclic, aryl, heteroaryl, halide, haloalkyl, hydroxy, thiohydroxy, alkoxy, thioalkoxy, aryloxy and thioaryloxy.

According to still further features in the described preferred embodiments the bioactive agent residue is selected from the group consisting of a fatty acid residue, a metabolite residue, a carbohydrate residue, an amino acid residue, a peptide residue, a protein residue, a hydroxamic acid residue, a nicotinic acid residue, a nicotinamide residue, a carnitine residue, a co-enzyme residue, a beta carotene residue, a bromelain residue, a steroidal anti-inflammatory agent residue, a non-steroidal anti-inflammatory drug residue, an anti-psychotic agent residue, an anti-thrombogenic agent residue, an anti-platelet agent residue, an anti-coagulant residue, an anti-diabetic agent residue, a growth factor residue, a statin residue, a toxin residue, an antimicrobial agent residue, an analgesic residue, an anti-metabolic agent residue, a vasoactive agent residue, a vasodilator agent residue, a prostaglandin residue, a hormone residue, a thrombin inhibitor residue, an enzyme residue, an oligonucleotide residue, a nucleic acid residue, an antisense residue, a protein residue, an antibody residue, an antigen residue, a vitamin residue, an immunoglobulin residue, a cytokine residue, a cardiovascular agent residue, a chemotherapeutic agent residue, an antioxidant residue, a phospholipid residue, an anti-proliferative agent residue, a heparin residue, and any combination thereof.

According to still further features in the described preferred embodiments the bioactive agent residue is a non-steroidal anti-inflammatory drug residue, whereby the non-steroidal anti-inflammatory drug is, for example, aspirin, celecoxib, diclofenac, diflunisal, etodolac, fenoprofen, flurbiprofen, ibuprofen, indomethacin, ketoprofen, ketorolac, meclofenamate, mefenamic acid, nabumetone, naproxen, oxaprozin, oxyphenbutazone, phenylbutazone, piroxicam, rofecoxib sulindac and tolmetin.

According to still further features in the described preferred embodiments the bioactive agent residue is an anti-diabetic agent residue, whereby the anti-diabetic agent can be, for example, acarbose, acetohexamide, chlorpropamide, glimepiride, glipizide, glyburide, lipoic acid, meglitol, metformin, miglitol, nateglinide, pioglitazone, repaglinide, rosiglitazone, tolazamide, tolbutamide and troglitazone.

According to still further features in the described preferred embodiments the NO-releasing group (Y in Formula I above) is selected from the group consisting of a —$ONO_2$ group, a —SNO group, a diazeniumdiolate and a mesoionic oxatriazole, and is preferably a —$ONO_2$ group.

According to still further features in the described preferred embodiments Z in Formula I above is an alkyl, preferably methyl.

According to still further features in the described preferred embodiments B in Formula I above comprises an ethylene chain.

According to still further features in the described preferred embodiments B in Formula I above is selected from the group consisting of —$CH_2$—$CH_2$—O—$CH_2$—, —$CH_2$—$CH_2$—NH—$CH_2$— and —$CH_2$—$CH_2$—S—$CH_2$—.

According to still further features in the described preferred embodiments X in Formula I above is hydrogen or an alkyl such as, for example, methyl, ethyl and isopropyl.

According to still further features in the described preferred embodiments X in Formula I above is a haloalkyl, such as, for example, trifluoromethyl.

According to still further features in the described preferred embodiments X in Formula I above is aryl, such as, for example, a substituted or unsubstituted phenyl and a substituted or unsubstituted naphthalenyl.

According to still further features in the described preferred embodiments the substituted phenyl is, for example, 4-trifluoromethylphenyl and pentafluorophenyl.

According to further features in preferred embodiments of the invention X in Formula I above is a heteroaryl, such as, for example, pyridin-3-yl.

According to still further features in the described preferred embodiments X in Formula I above is a heteroalicyclic, such as, for example, piperidine-4-yl.

According to still further features in the described preferred embodiments X in Formula I above is amine, such as, for example, —$NH_2$ and —$N(CH_3)_2$.

According to still further features in the described preferred embodiments X in Formula I above is an alkoxy, such as, for example, methoxy.

According to still further features in the described preferred embodiments X in Formula I above is a moiety containing one or more NO-releasing group(s), such as, for example, 1-nitroxy-ethyl, [4-methyl-5-(2-nitrooxy-ethyl)-thiazol-2-yl]-diazene, 4-methyl-5-(2-nitrooxy-ethyl)-thiazole and 2-butyl-4-methyl-5-(2-nitrooxy-ethyl)-thiazole.

According to still further features in the described preferred embodiments X in Formula I above is a non-steroidal anti-inflammatory drug residue, such as, for example, an aspirin residue, an ibuprofen residue and a naproxen residue.

According to still further features in the described preferred embodiments X in Formula I above is an anti-diabetic agent residue, such as, for example, a lipoic acid residue.

According to still further features in the described preferred embodiments A in Formula I above is a biocleavable moiety and X is a bioactive agent, as described herein.

According to still further features in the described preferred embodiments the biocleavable moiety can be, for example, amide, carboxylate, carbonate, carbamate, phosphate, hydrazide, thiohydrazide, disulfide, epoxide, peroxo and methyleneamine.

Exemplary NO-donating compounds according to this and other aspects of the present invention are set forth in Tables 1 and 2 hereinbelow.

According to another aspect of the present invention there is provided a pharmaceutical composition, which comprises, as an active ingredient, an NO-donating compound as described hereinabove, and a pharmaceutically acceptable carrier.

According to still further features in the described preferred embodiments the pharmaceutical composition is packaged in a packaging material and identified in print, in or on the packaging material, for use in the treatment of a medical condition in which modulating an NO level is beneficial. Preferably modulating the NO level includes elevating the NO level.

According to still further features in the described preferred embodiments the medical condition in which modulating an NO level is beneficial is selected from the group consisting of a cardiovascular disease or disorder, a gastrointestinal disease or disorder, an inflammatory disease or disorder, a respiratory disease or disorder, a central nervous system disease or disorder, a neurodegenerative disease or disorder, a psychiatric disease or disorder, a blood pressure-associated disease or disorder, a coronary artery disease or disorder, atherosclerosis, a cholesterol level-associated disease or disorder, an arterial thrombotic disease or disorder, a heart failure, a stroke, a septic shock, a NSAID-induced gastric disease or disorder, an inflammatory bowel disease or disorder, an ischemic renal disease or disorder, a peptic ulcer, diabetes, pulmonary hypertension, sickle cell anemia, asthma, a chronic obstructive pulmonary disease or disorder, dementia, epilepsy, a neuroinflammatory disease or disorder, trauma, multiple sclerosis, an erectile dysfunction, a male and female sexual dysfunction and an age-related disease or disorder.

According to yet another aspect of the present invention there is provided a method of treating or preventing a medical condition in which modulating an NO level is beneficial, as described hereinabove, which is effected by administering to a subject in need thereof a therapeutically effective amount of an NO-donating compound as described hereinabove.

According to still further features in the described preferred embodiments administering of the NO-donating compound(s) is effected orally, rectally, intravenously, topically, intranasally, intradermally, transdermally, subcutaneously, intramuscularly, intrperitoneally, intraperitoneally, by inhalation or by intrathecal catheter.

According to still further features in the described preferred embodiments the NO-donating compound is administered either per se or as a part of the pharmaceutical composition described hereinabove.

According to still further features in the described preferred embodiments the therapeutically effective amount of the NO-donating compound(s) ranges between about 0.01 mg/kg body and about 5 mg/kg body.

According to still further features in the described preferred embodiments the method according to this aspect of the present invention further comprises administering to the subject an additional active ingredient, which is capable of treating or preventing the medical condition described hereinabove.

According to still another aspect of the present invention there is provided a method of synthesizing a compound having the general Formula I presented hereinabove. The method comprising:

providing a thioamide having a general Formula II:

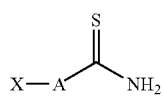

Formula II wherein the thioamide is preferably selected from the group consisting of N,N-dimethylthiourea, thiobenzamide, thiourea, N-allylthiourea, acetylthiourea, N-ethylthiourea, N,N-dimethylthiourea, alpha-naphthylthiourea, 1-[(3,5-bis-trifluoromethyl)phenyl]thiourea and dithiooxalamide;

providing a reactive compound having the general Formula III:

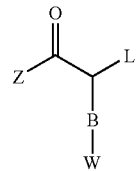

Formula III wherein:

L is a leaving group, preferably selected from the group consisting of halide, alkoxy, aryloxy, amine, hydroxy, azide, nitro, cyano, thiocyanate, O-carboxylate, thiohydroxy and sulfonate, and more preferably is halide;

Z and B are as defined above; and

W is a pre-nitratable group, preferably selected from the group consisting of alkoxy, aryloxy, thioalkoxy, thioaryloxy, silanoxy, silicate and O-carboxylate;

reacting the thioamide having the general Formula II and the compound having the general Formula III, to thereby generate a thiazole derivative having a general Formula IV:

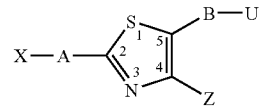

Formula IV wherein:

A, X, B and Z are as defined above; and

U is a nitratable group, preferably selected from the group consisting of hydroxy and thiohydroxy; and converting the nitratable group into an NO-releasing group.

Preferably, converting the nitratable group into an NO-releasing group is effected by reacting the thiazole derivative of Formula IV with a nitrating agent, which contains the NO-releasing moiety. Further preferably, the NO-releasing moiety is $ONO_2$ and the nitrating agent is nitric acid.

In a preferred embodiment of this aspect of the present invention, the compound of Formula III is 5-acetoxy-3-chloro-2-pentanone.

According to still further features in the described preferred embodiments providing the thioamide comprises:

providing an amide having a general Formula V:

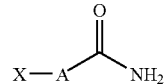

Formula V wherein:

X and A are as defined above;

whereby the amide is preferably selected from the group consisting of propionamide, acetamide, isobutyramide, L-(-)-lactamide, trifluoroacetamide, carbamic acid methyl ester, hexanedioic acid diamide, piperidine-4-carboxylic acid amide, thionicotinamide, naproxenamide, 4-(trifluoromethyl)-thiobenzamide, azodicarbonamide, 2-(4-isobutyl-phenyl)-propionamide, isonicotinamide, 2,2,2-trifluoroacetamide, glycinamide, 4-aminobenzamide, 2,3,4,5,6-pentafluorobenzamide, 2-aminobenzamide, ethyloxamate, 2,6-difluorobenzamide, N-phenylurea, 2,4-dichlorophenylacetamide, 2,4-dichlorophenoxyacetmide, 2-phenylbutyamide, azodicarbonamide, 3,5-difluorobenzamide, DL-lipoamide, Rubeanic acid, adpamide, aalonamide, acrylamide and 2-hydroxy-benzamide; and reacting the amide with a thiolating agent.

Preferably, the thiolating agent is phosphorous pentasulfide.

According to still further features in the described preferred embodiments the pre-nitratable group is acetate and the nitratable group is hydroxy.

According to an additional aspect of the present invention there is provided a method of synthesizing a compound having the general Formula I hereinabove, in which A is a biocleavable moiety.

The method according to this aspect of the present invention comprises:

providing a thiazole having a general Formula VI:

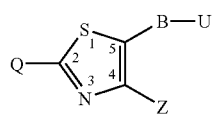

Formula VI wherein:

Z, B and U are as defined above; and

Q is a first reactive group;

whereby the thiazole is preferably 2-(2-amino-4-methyl-thiazol-5-yl)-ethanol or 5-(2-hydroxy-ethyl)-4-methyl-thiazole-2-carboxylic;

providing a compound the general Formula VII:

 Formula VII wherein:

X is as defined above; and

K is a second reactive group;

whereby this compound is preferably selected from consisting of 2-(6-methoxy-naphthalen-2-yl)-propionic acid, 4-[1,2]dithiolan-3-yl-butyric acid, 2-(4-isobutyl-phenyl)-propionic acid, nicotinic acid, 1-oxy-nicotinic acid, 2,6-difluoro-benzoic acid, phthalazin-1-yl-hydrazine, 3-chloropropene, 4-acetylamino-benzoic acid, hexadecanoic acid, 2-acetoxy-benzoic acid, pyrrolidine-2-carboxylic acid, (2,4-dichloro-phenyl)-acetic acid, (2,4-dichloro-phenoxy)-acetic acid and 17-hydroxy-10,13-dimethyl-1,2,6,7,8,9,10,11,12, 13,14,15,16,17-tetradecahydro-cyclopenta[a]phenanthren-3-one;

reacting the thiazole having the general Formula VI and the compound having the general Formula VII, to thereby generate a thiazole derivative having a general Formula IV:

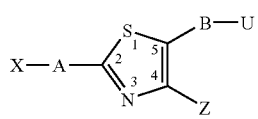

Formula IV wherein:

A, X, B and Z are as defined above; and

U is a nitratable group as described hereinabove; and converting the nitratable group into an NO-releasing group, as described hereinabove.

According to still further features in the described preferred embodiments, the biocleavable moiety is selected from the group consisting of amide, carboxylate, carbonate, carbamate, phosphate, hydrazide, thiohydrazide, disulfide, epoxide, peroxo and methyleneamine.

According to still further features in the described preferred embodiments the first reactive group and the second reactive group are each independently selected from the group consisting of amine, halide, acyl-halide, sulfonate, sulfoxides, phosphate, hydroxy, alkoxy, aryloxy, thiohydroxy, thioalkoxy, thioaryloxy, cyano, nitro, azo, isocyanate, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. Preferably, the first reactive group and the second reactive group are each independently selected from the group consisting of amine, hydrazine, alkoxy, halide and carboxylate.

According to still an additional aspect of the present invention there is provided a medical device which includes an NO-donating compound as described hereinabove and a delivery system configured for delivering the NO-donating compound to a bodily site of a subject.

According to still further features in the described preferred embodiments the bodily site in selected from the group consisting of skin, scalp, a dermal layer, an eye, an ear, a small intestines tissue, a large intestines tissue, a kidney, a pancreas, a liver, a digestive tract, a respiratory tract, a bone, a bone marrow tissue, a mucosal membrane, a nasal membrane, the blood system, a blood vessel, a muscle, a pulmonary cavity, an artery, a vein, a capillary, a heart, a heart cavity, a male reproductive organ, a female reproductive organ and a visceral organ.

According to still further features in the described preferred embodiments the NO-donating compound forms a part of the pharmaceutical composition described hereinabove.

According to still further features in the described preferred embodiments the delivering is effected by inhalation and the delivery system is selected from the group consisting of a metered dose inhaler, a respirator, a nebulizer inhaler, a dry powder inhaler, an electric warmer, a vaporizer, an atomizer and an aerosol generator.

According to still further features in the described preferred embodiments the delivering is effected transdermally and the delivery system is selected from the group consisting of an adhesive plaster and a skin patch.

According to still further features in the described preferred embodiments the delivering is effected topically and the delivery system is selected from the group consisting of an adhesive strip, a bandage, an adhesive plaster, a wound dressing and a skin patch.

According to still further features in the described preferred embodiments the delivering is effected by implanting the medical device in a bodily organ.

According to still further features in the described preferred embodiments the delivery system further includes a biocompatible matrix. Preferably the biocompatible matrix includes a biodegradable polymer. Further preferably, the biocompatible matrix includes a slow release carrier.

According to still further features in the described preferred embodiments the delivery system is selected from the group consisting of an aortic aneurysm graft device, an atrioventricular shunt, a catheter, a defibrilator, a heart valve, a hemodialysis catheter, a hemodialysis graft, an indwelling arterial catheter, an indwelling venous catheter, a needle, a pacemaker, a pacemaker lead, a patent foramen ovale septal closure device, a stent, a stent graft, a suture, a synthetic vascular graft, a thread, a tube, a vascular anastomosis clip, a vascular aneurysm occluder, a vascular clip, a vascular prosthetic filter, a vascular sheath and a drug delivery port, a venous valve and a wire.

According to another aspect of the present invention there is provided a use of an NO-donating compound as described herein in the treatment of a medical condition in which modulating an NO level is beneficial, as detailed herein.

According to another aspect of the present invention there is provided a use of an NO-donating compound as described herein for the preparation of a medicament for treating or preventing a medical condition in which modulating an NO level is beneficial, as detailed herein.

The present invention successfully addresses the shortcomings of the presently known configurations by providing a novel class of NO-donating agents, which are both highly efficient in treating NO-deficiencies and are not associated with drug tolerance, and which may further have therapeutically active agent attached thereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

The term "therapeutically effective amount" or "pharmaceutically effective amount" denotes that dose of an active ingredient or a composition comprising the active ingredient that will provide the therapeutic effect for which the active ingredient is indicated, herein, modulating and preferably elevating an NO level.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

Figure 5:
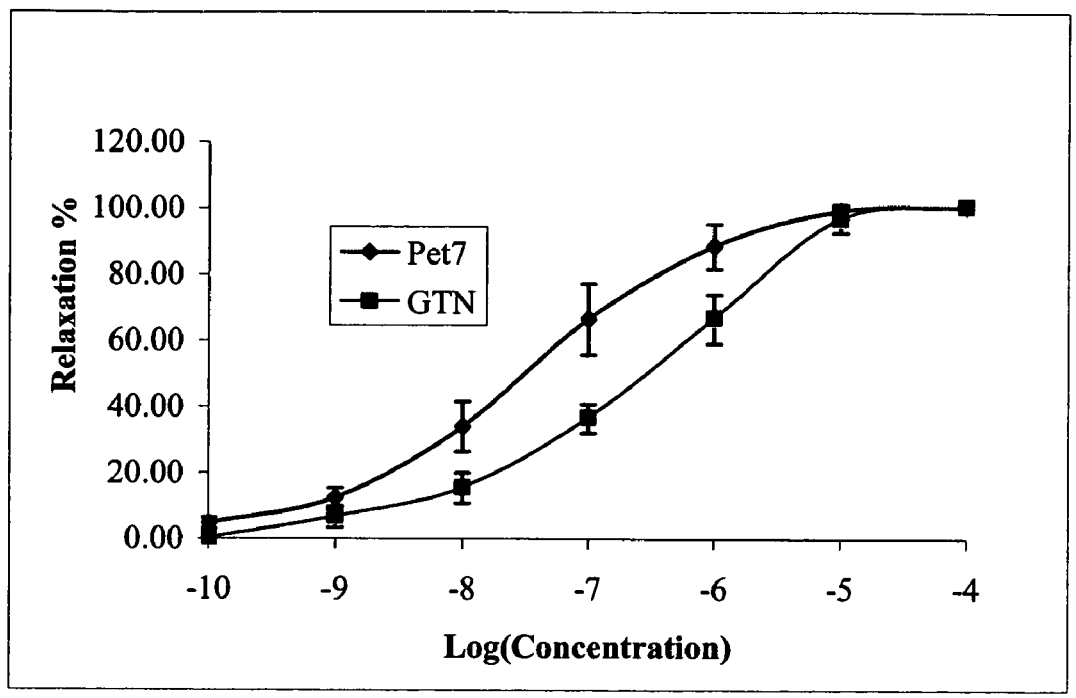
Figure 6:
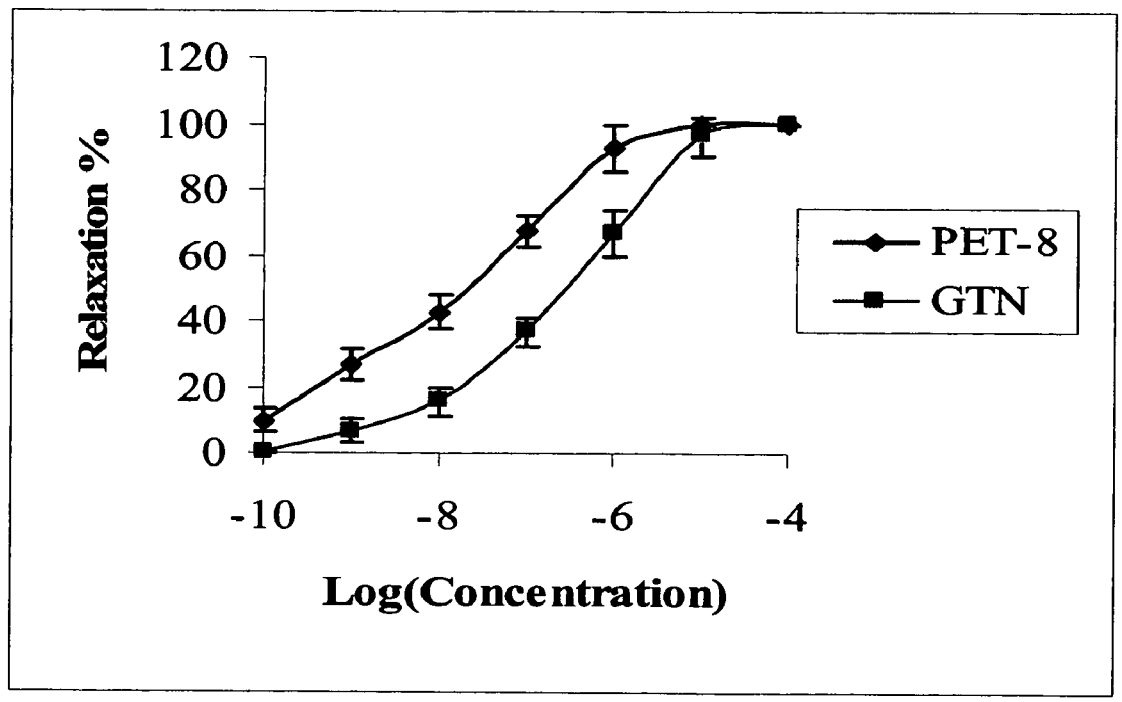
Figure 7:
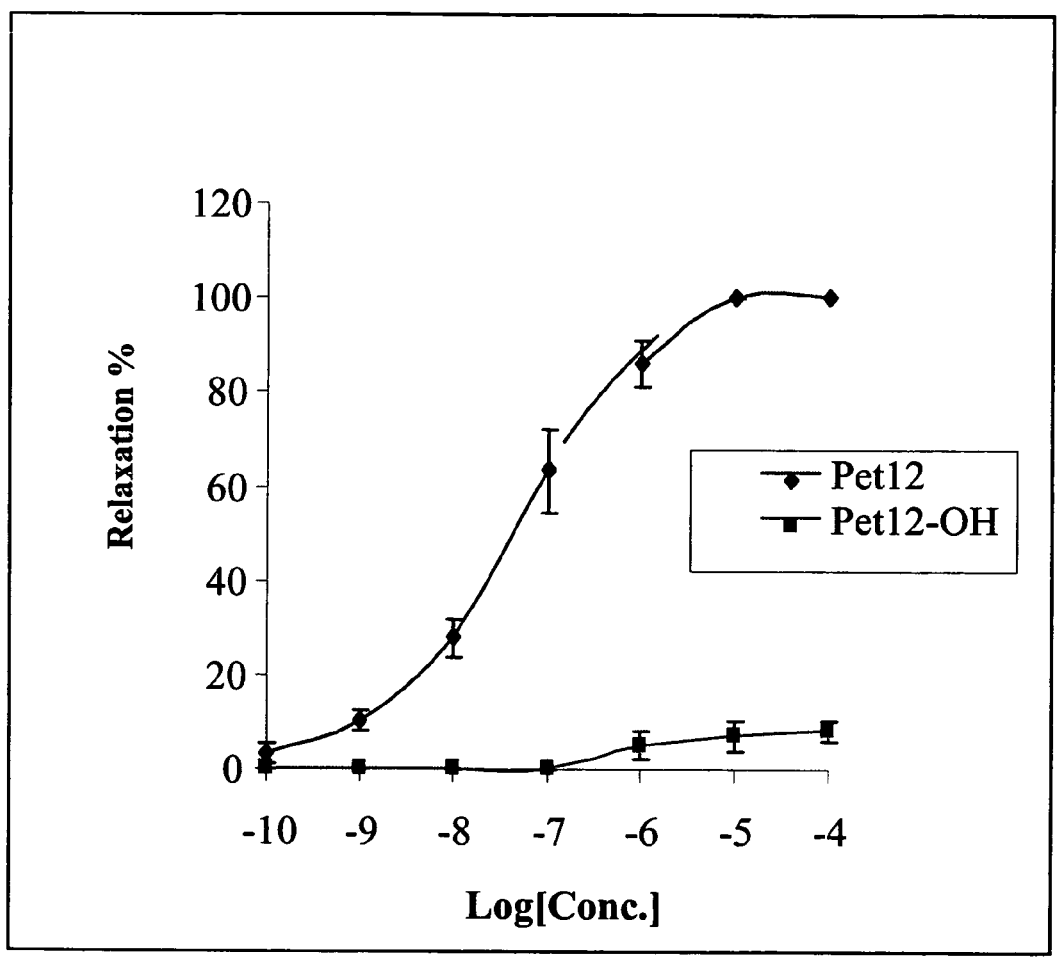
Figure 8:
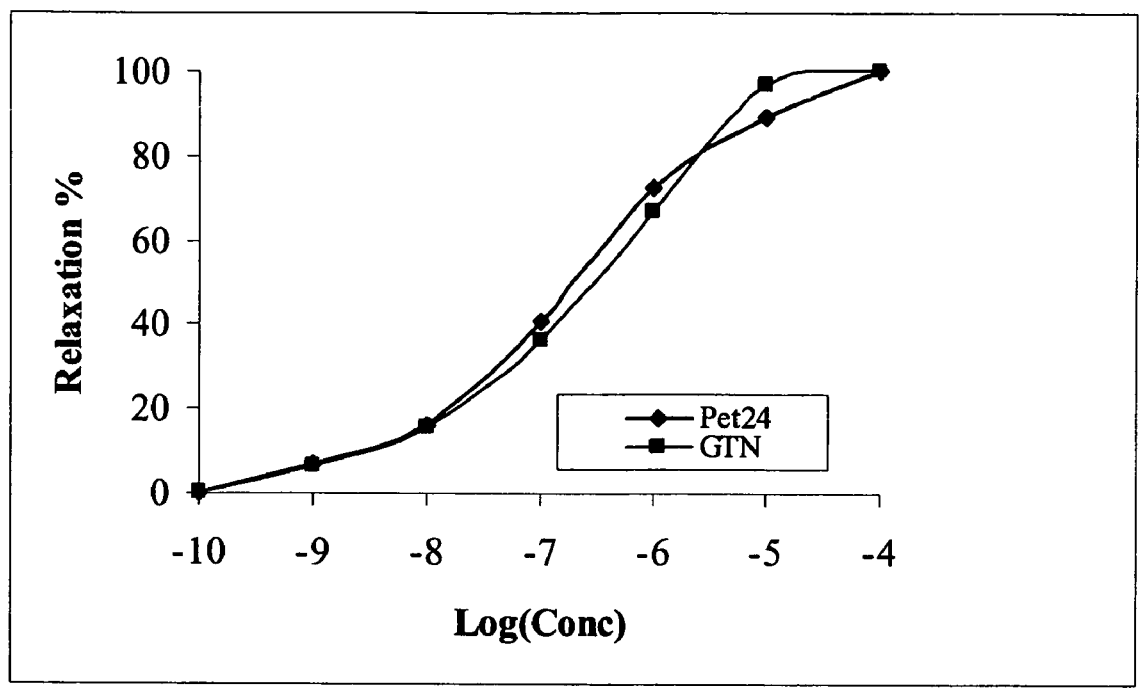
Figure 9:
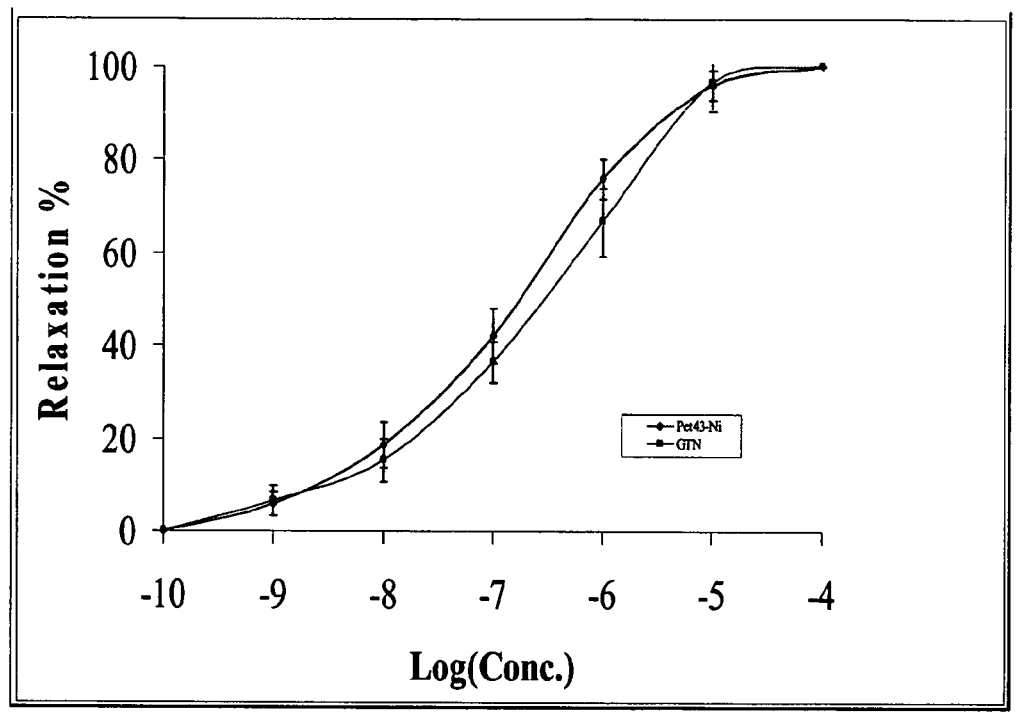
Figure 10:
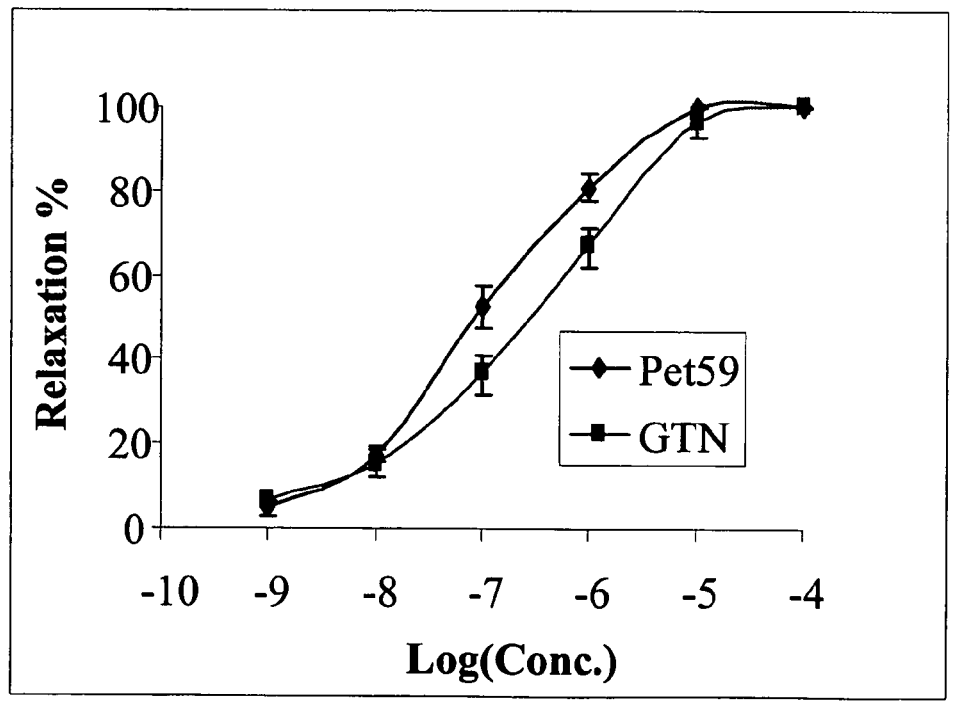
Figure 11:
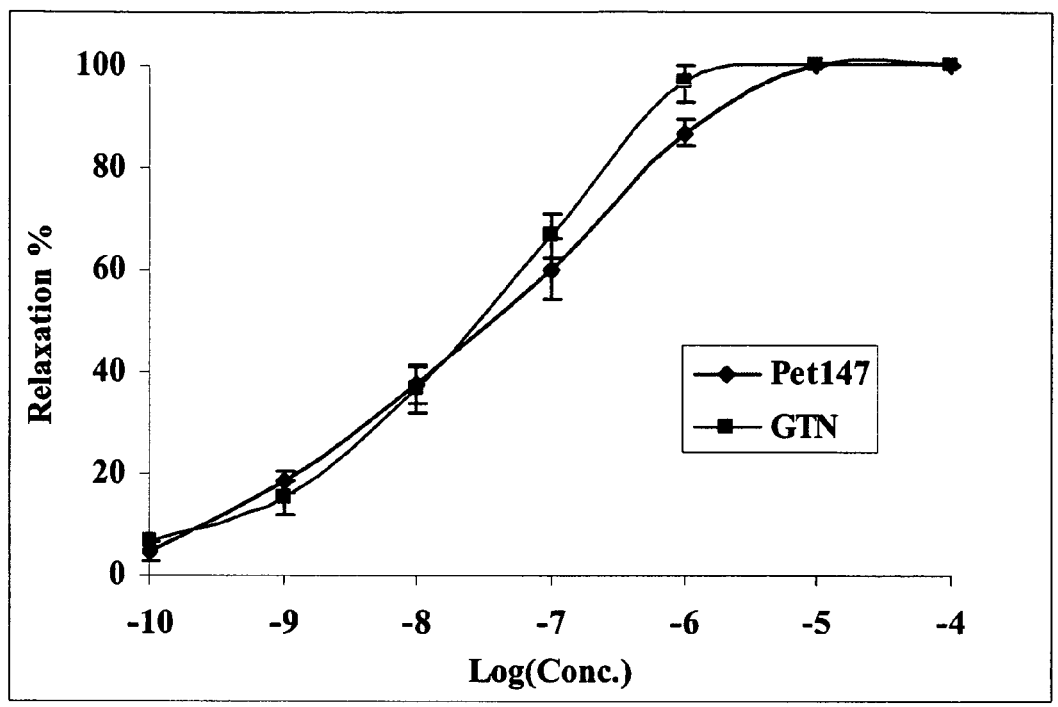
Figure 12:
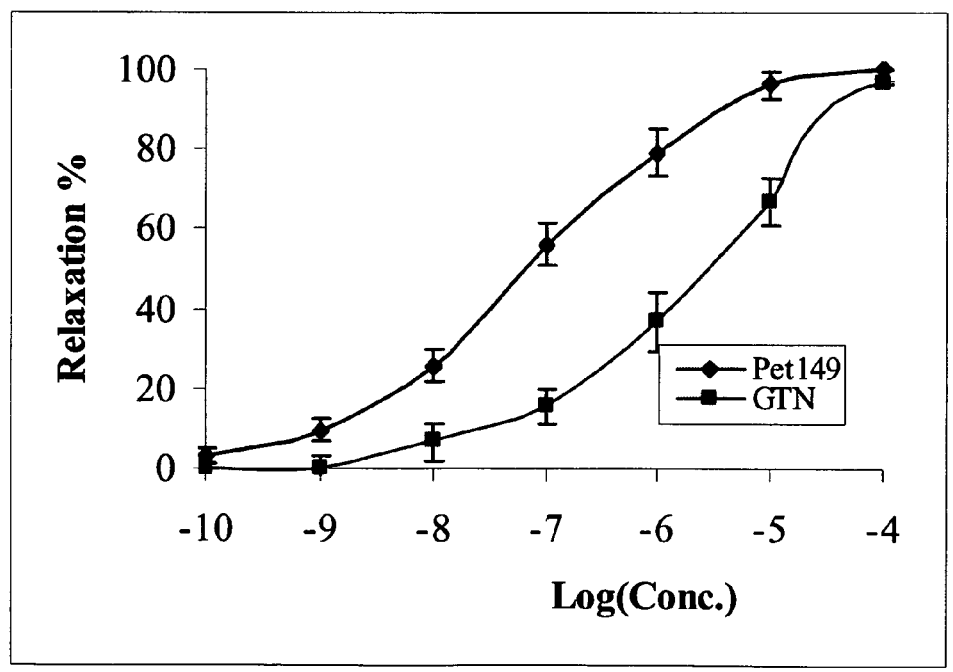
Figure 13:
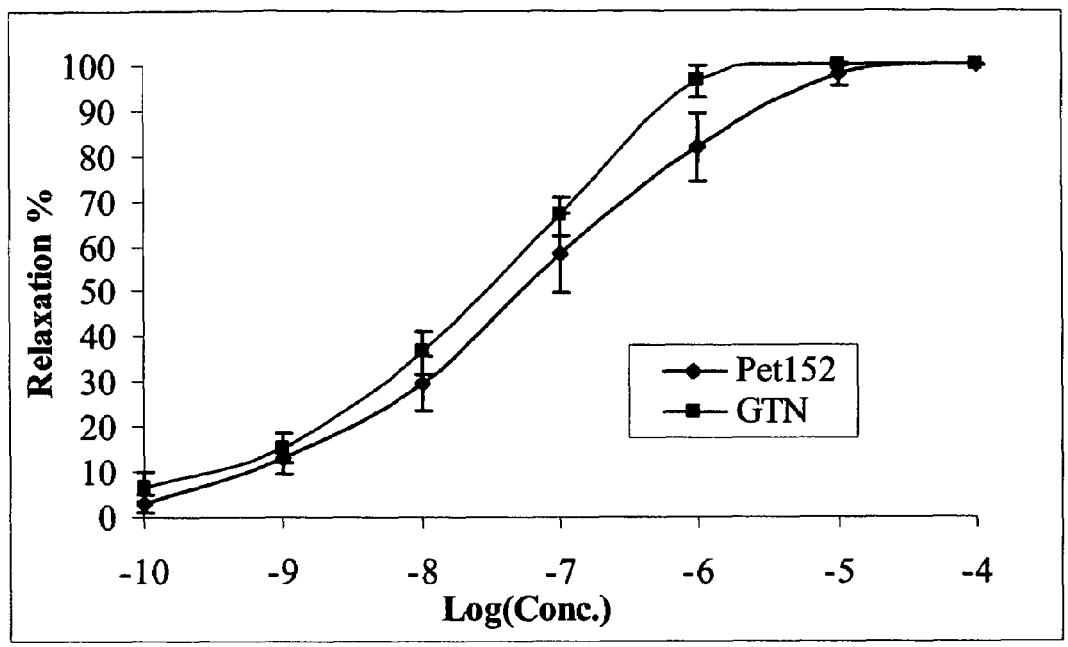
Figure 14:
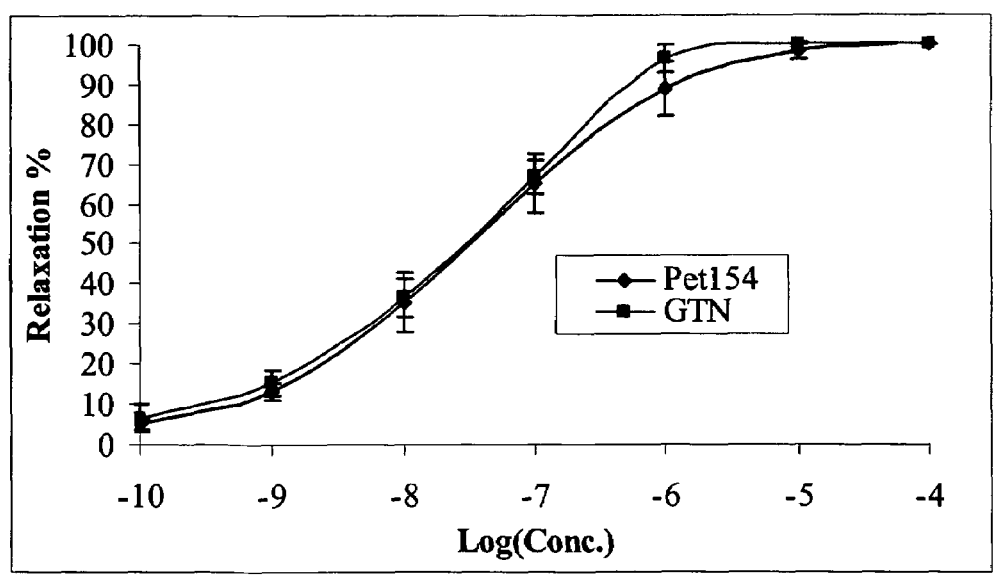
Figure 15:
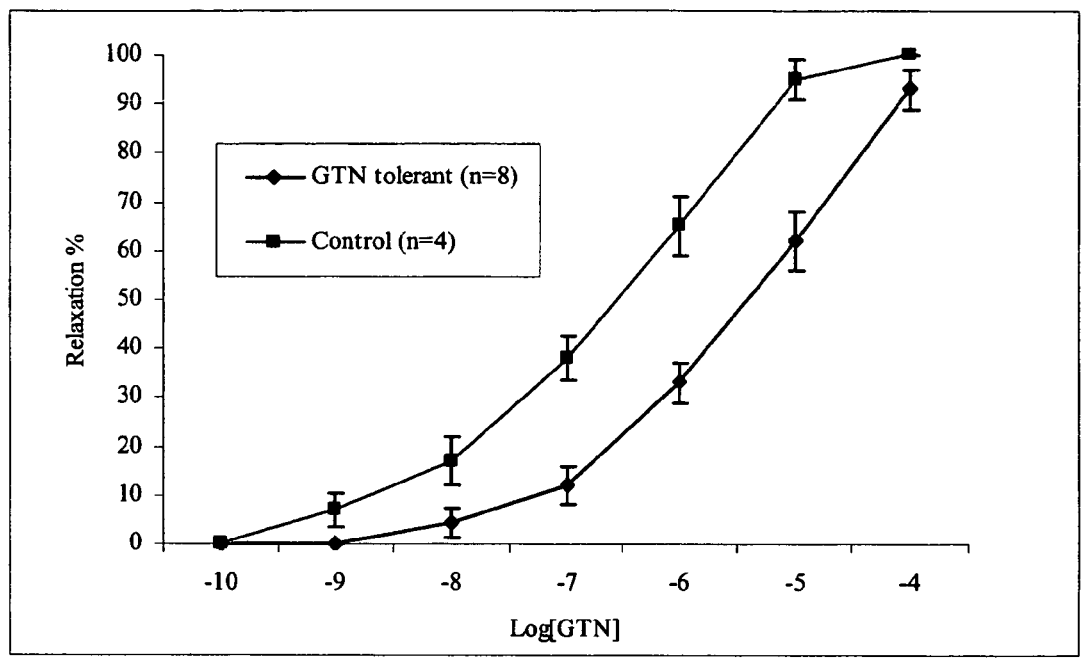
Figure 16:
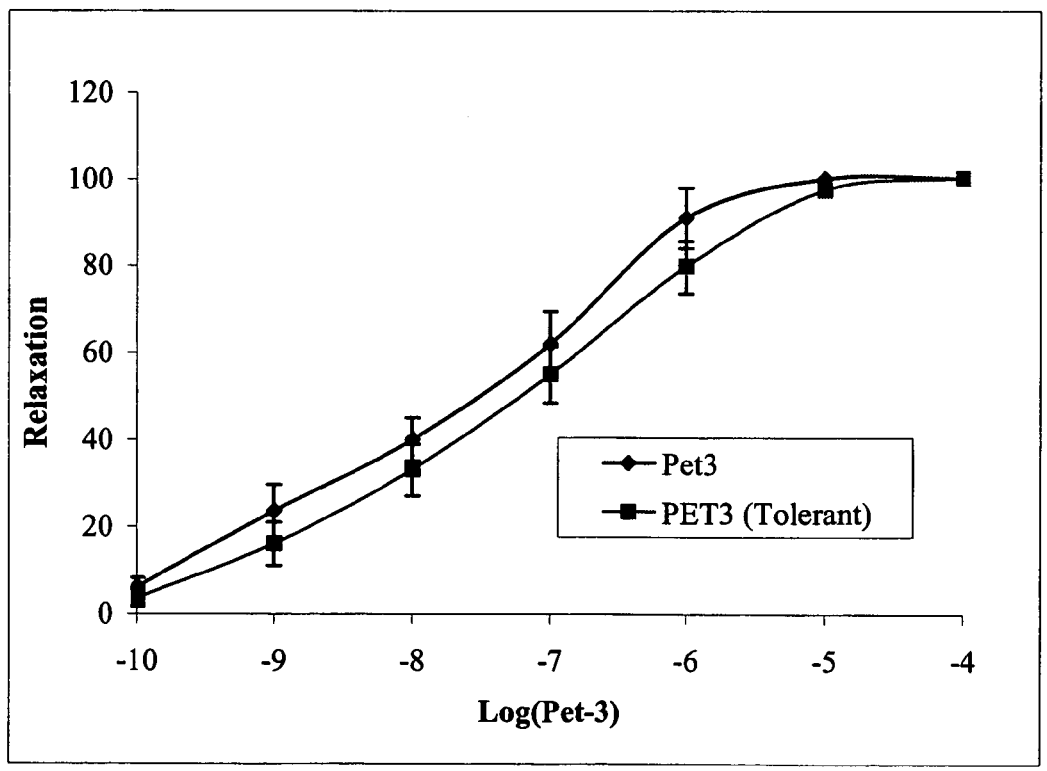
Figure 17:
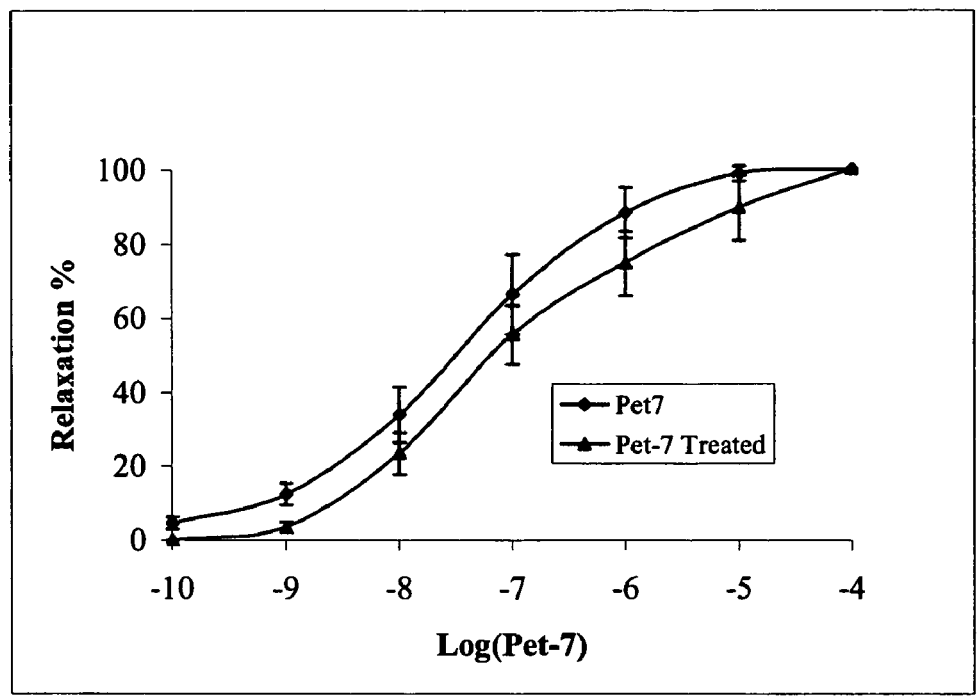
Figure 18:
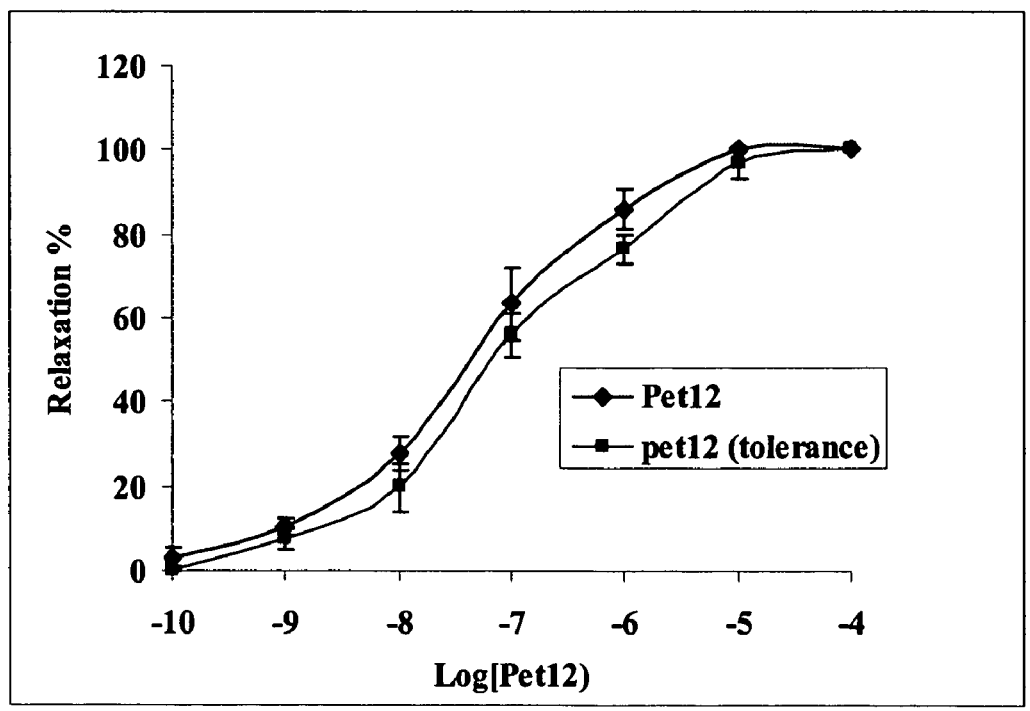
Figure 19:
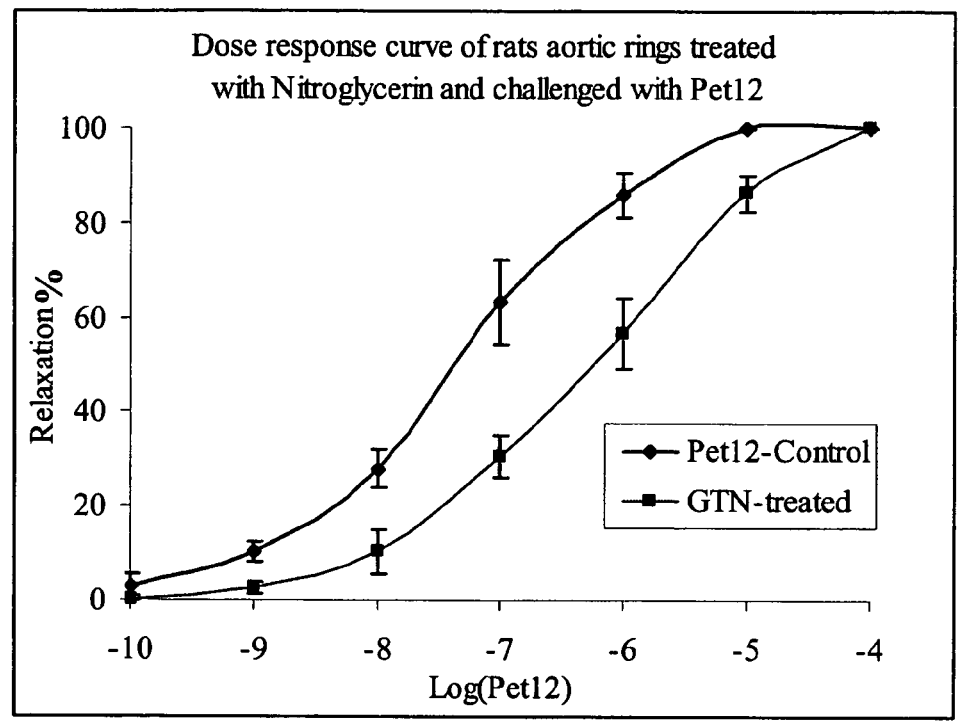
Figure 20:
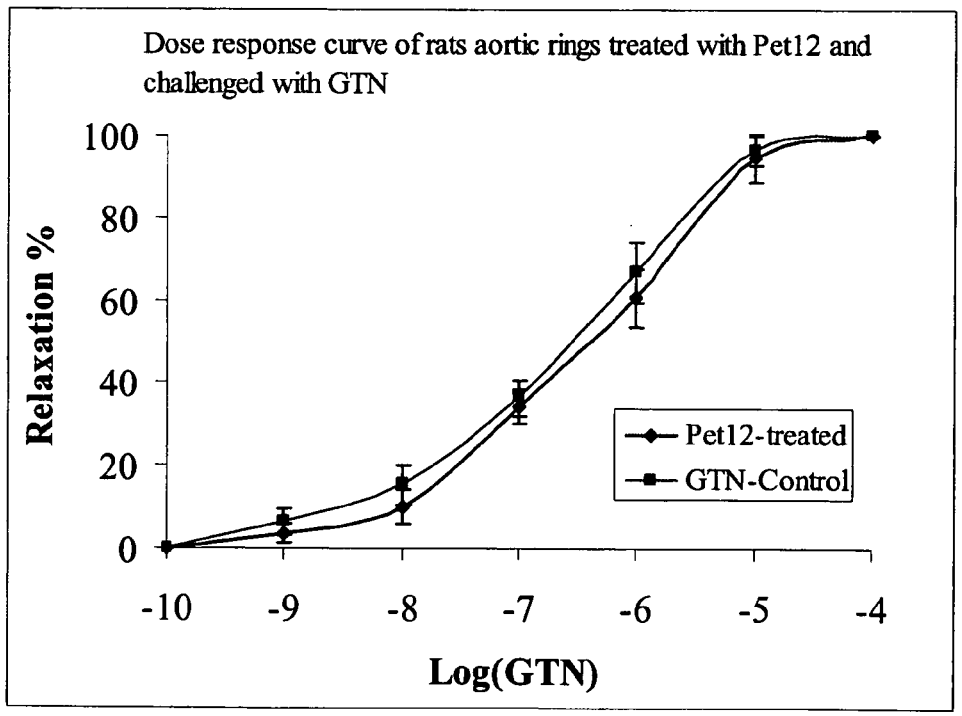
Figure 21:
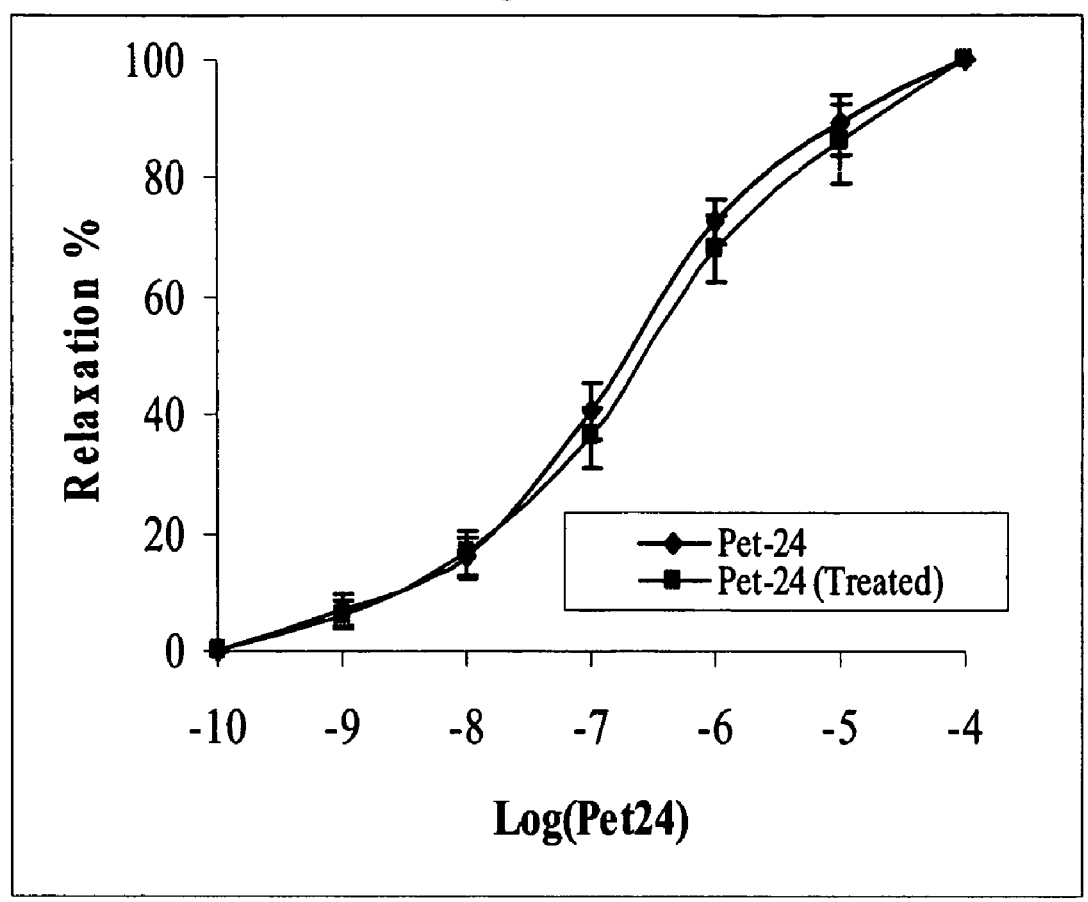
Figure 22:
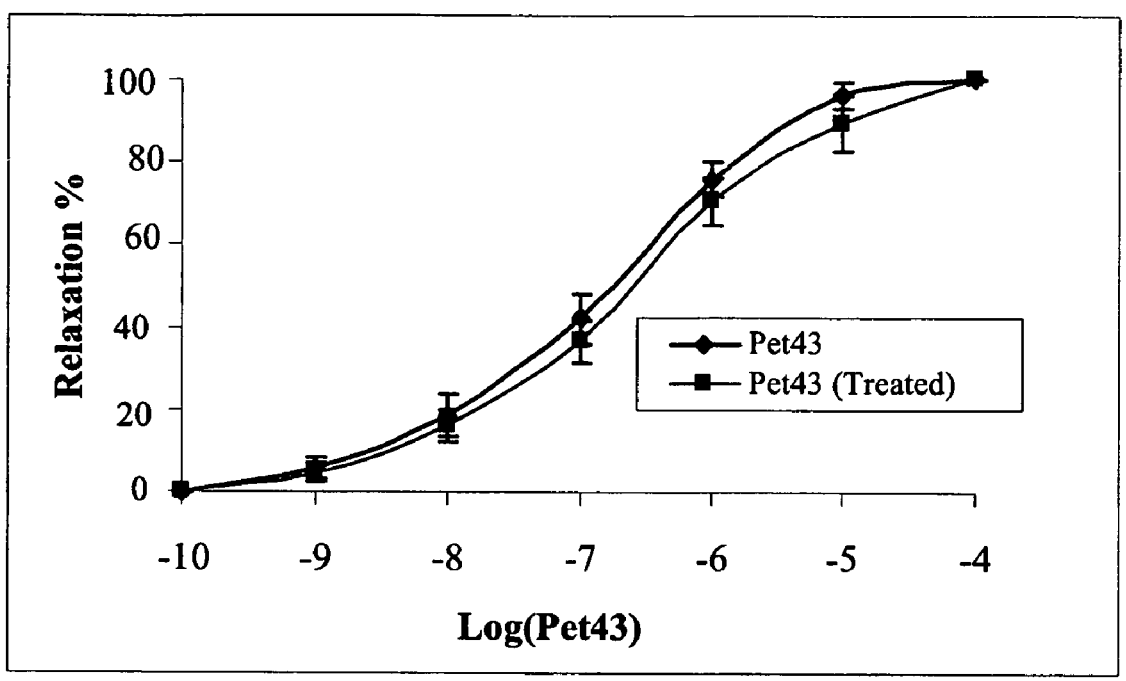
Figure 23:
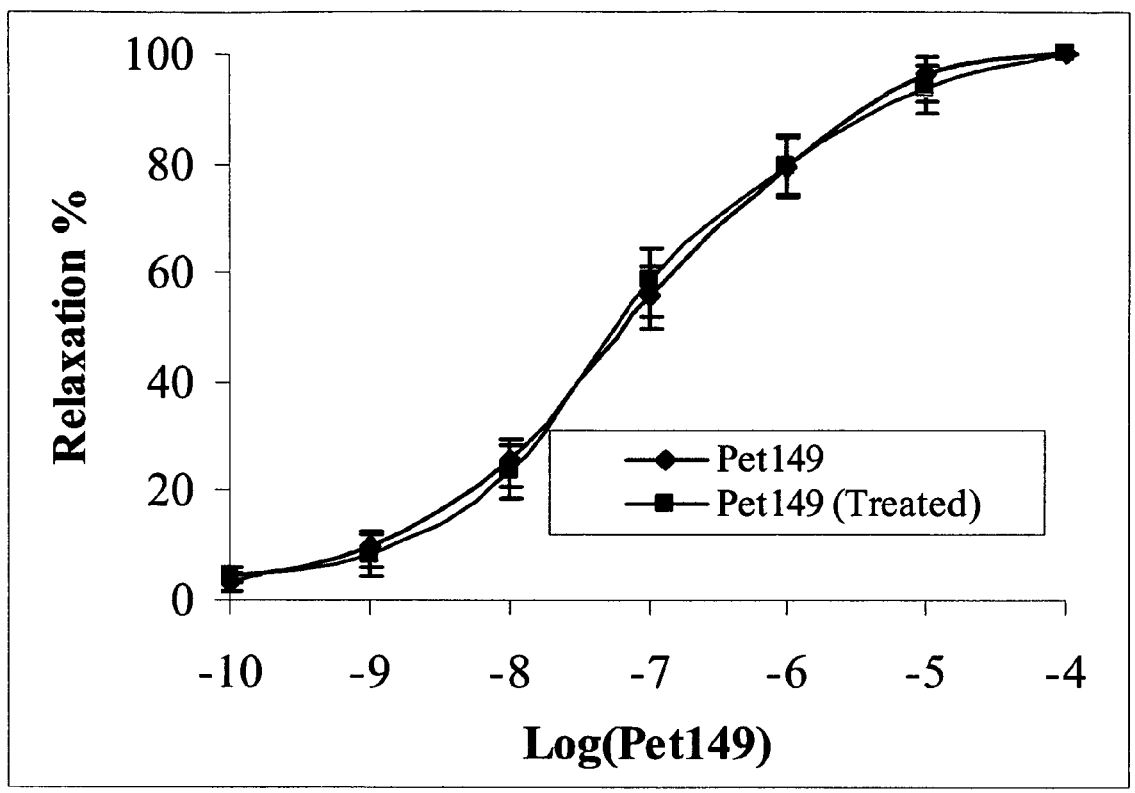
Figure 24:
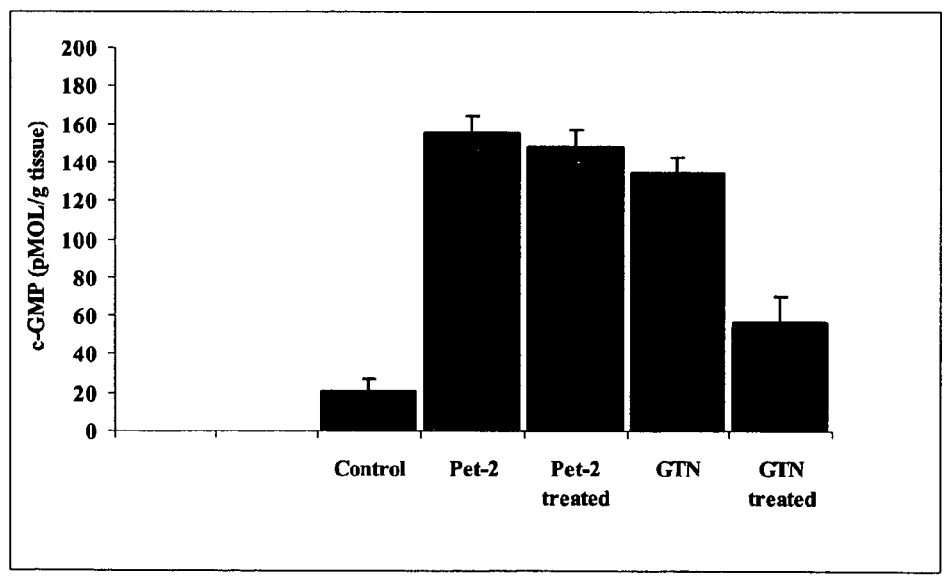
Figure 25:
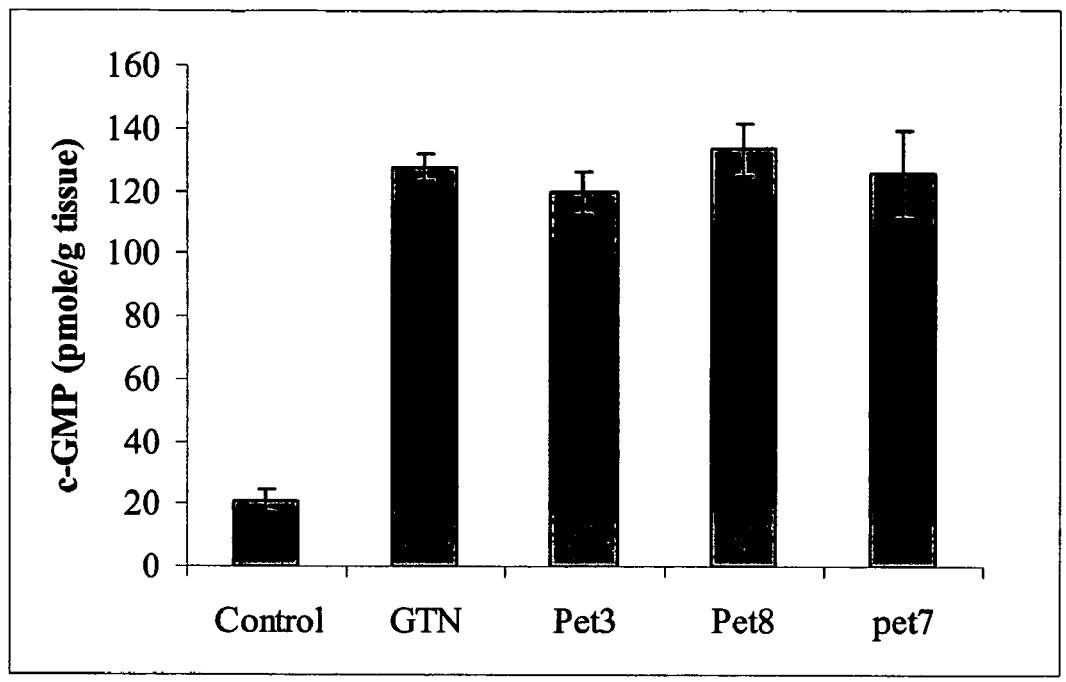
Figure 26:
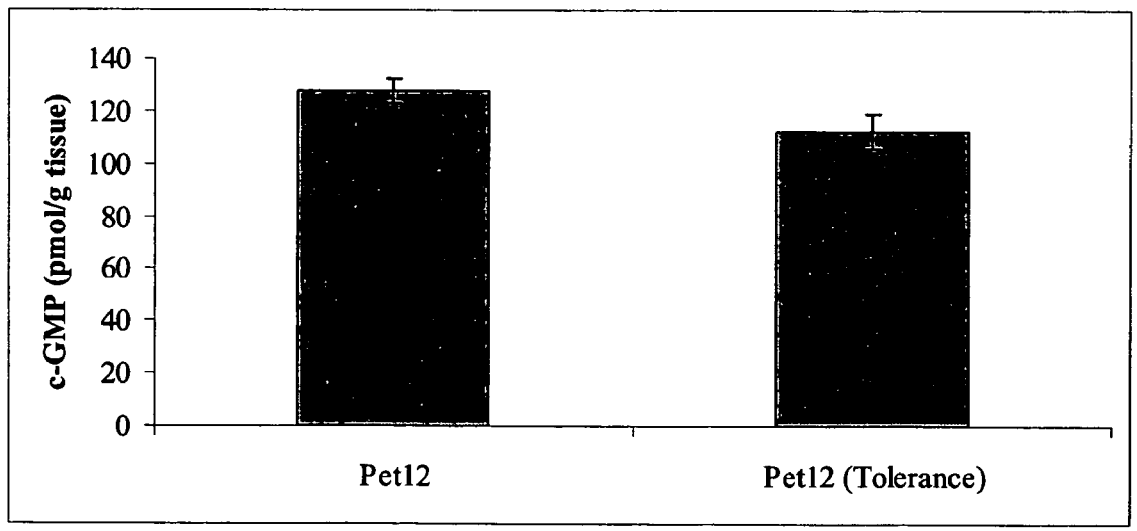
Figure 27:
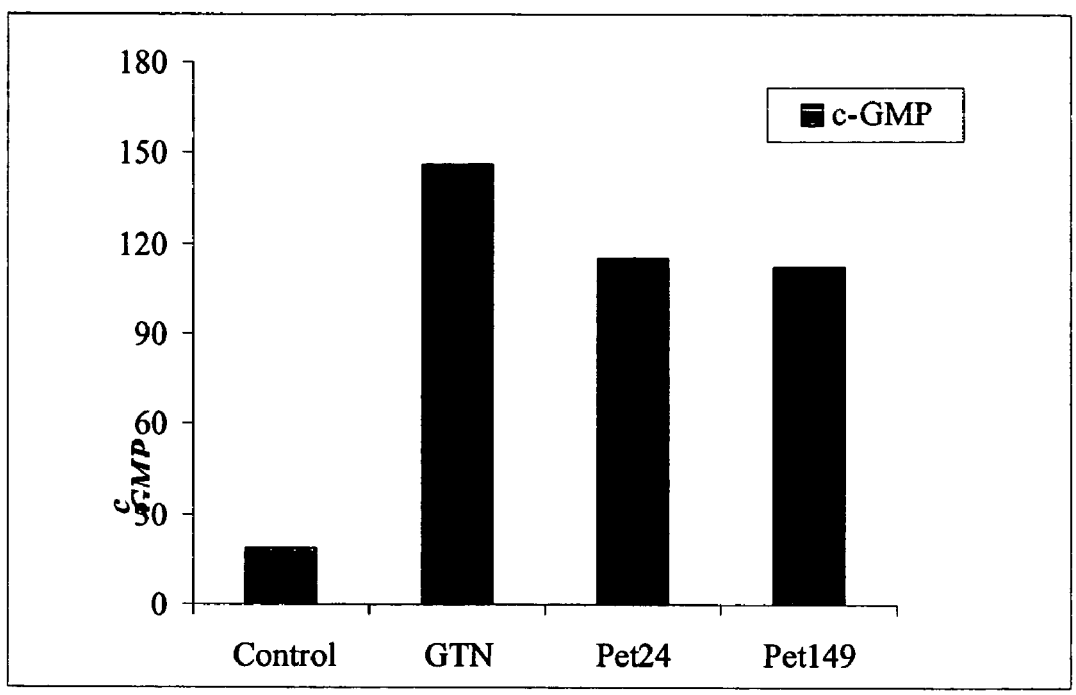
Figure 28:
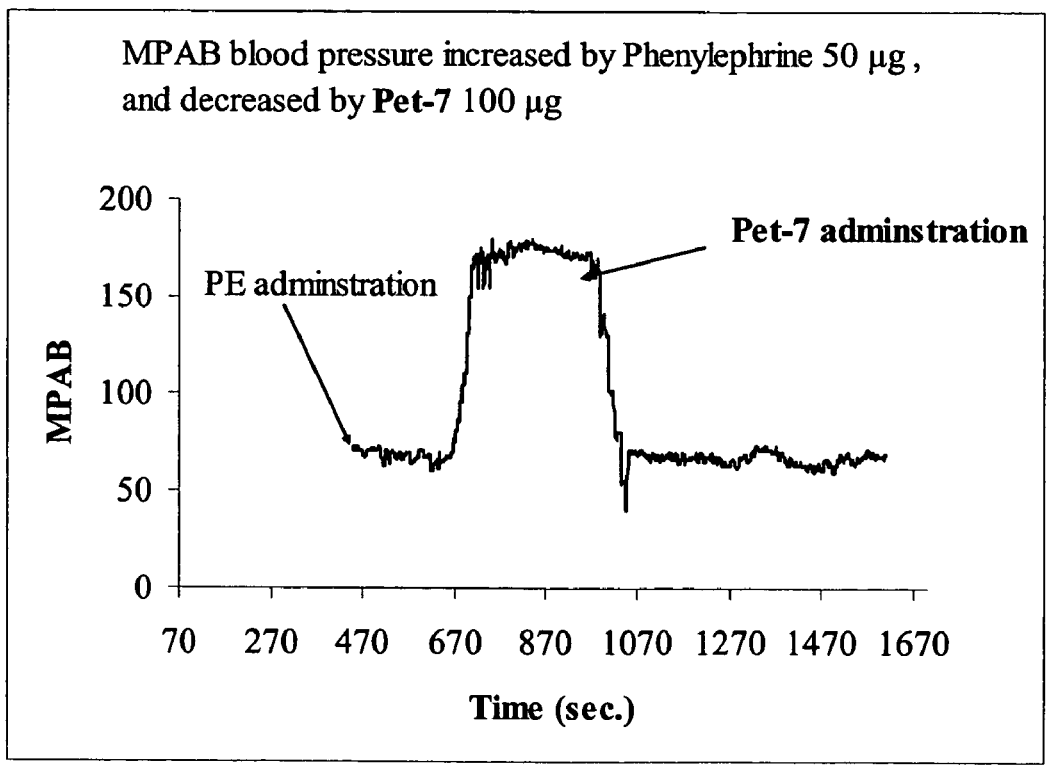
Figure 29:
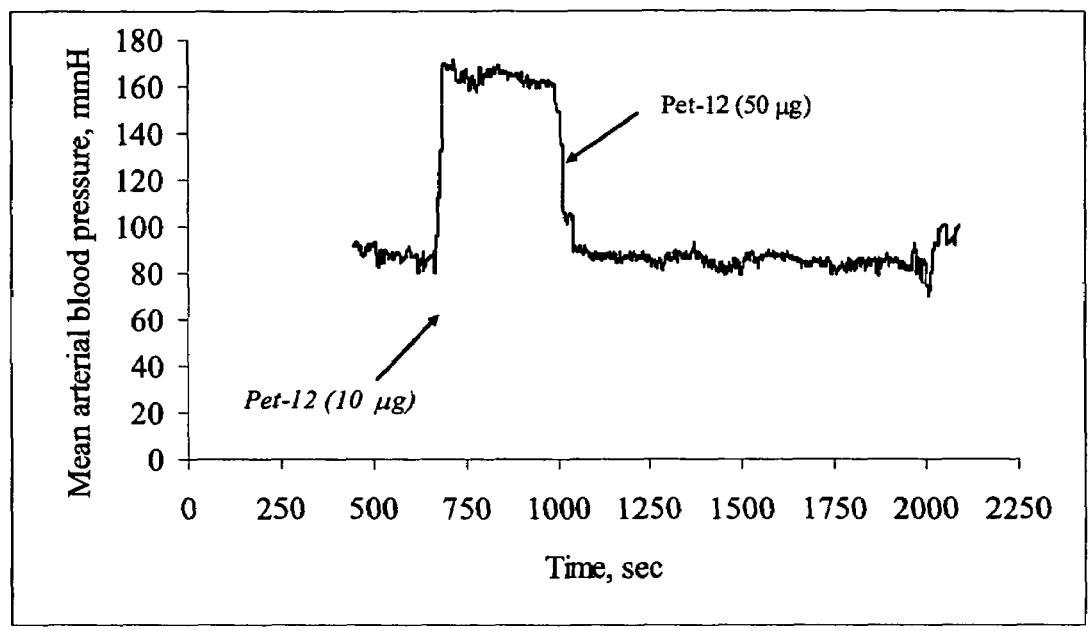
Figure 30:
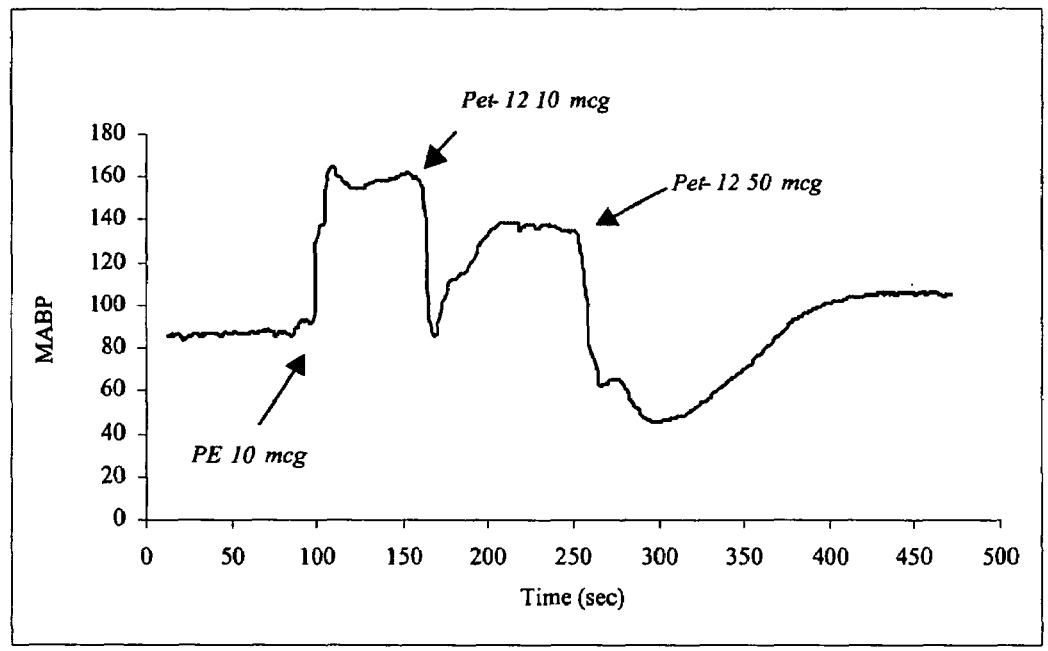
Figure 31:
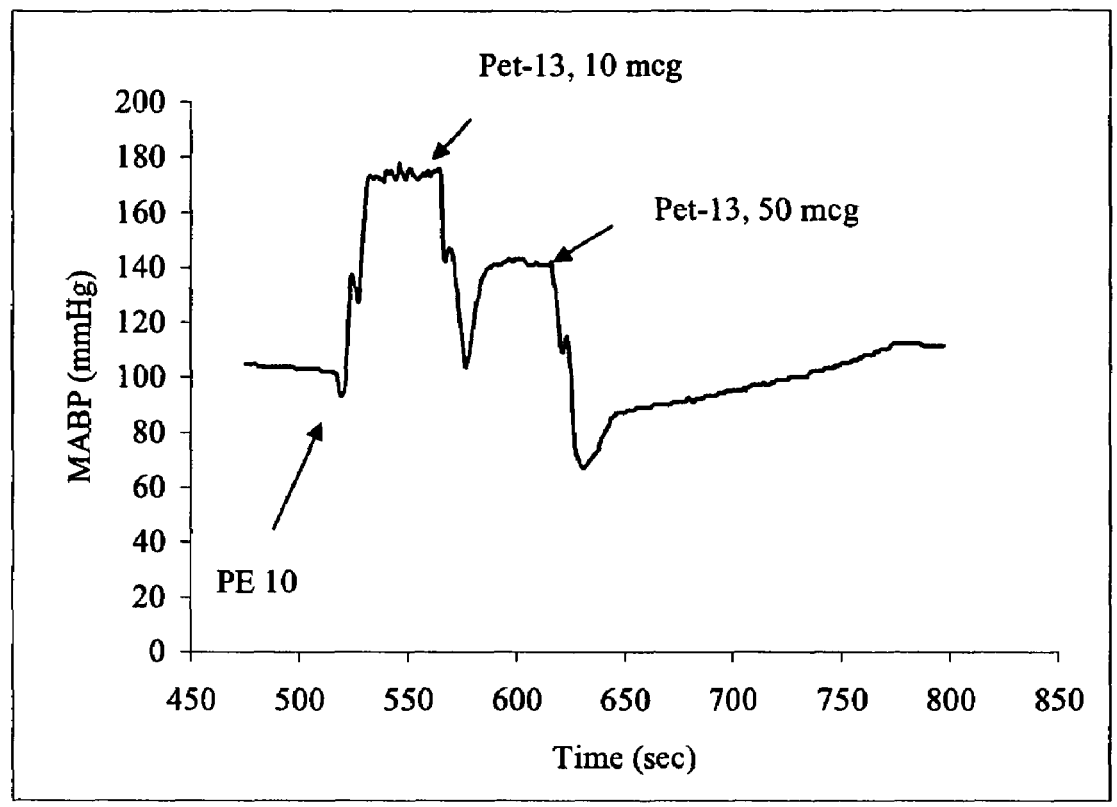
Figure 32:
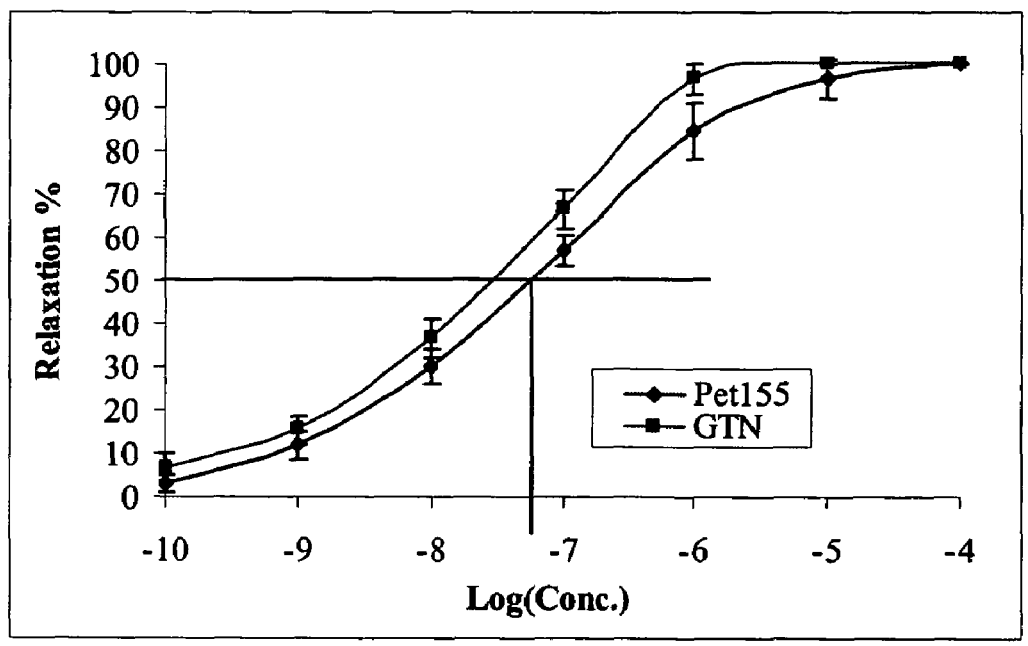
Figure 33:
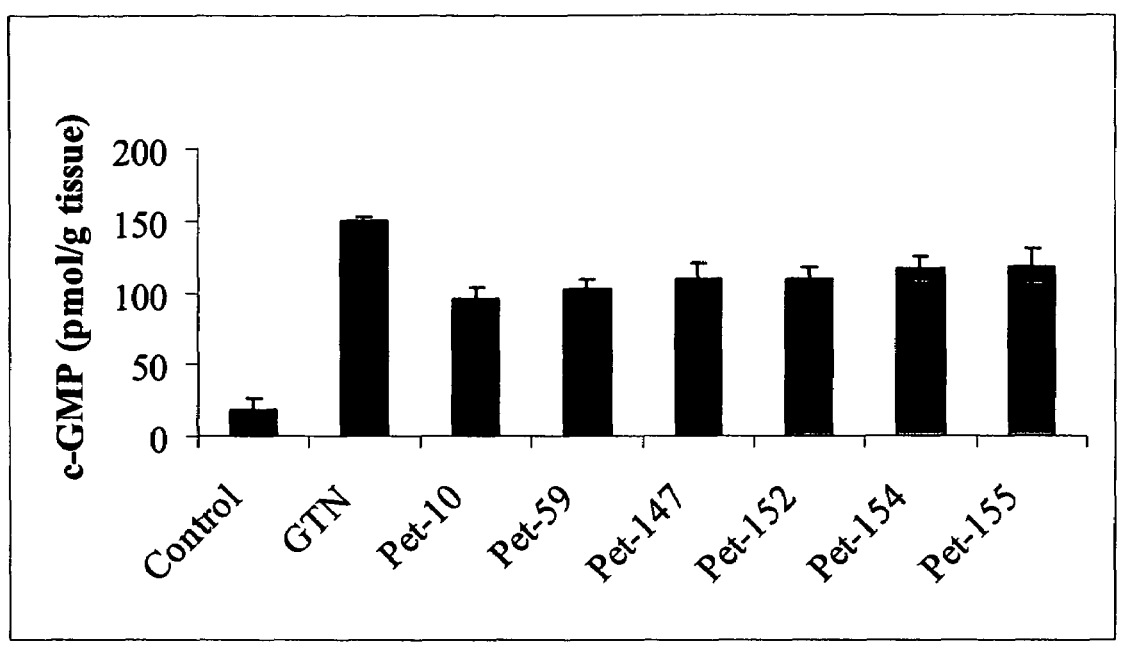
Figure 34:
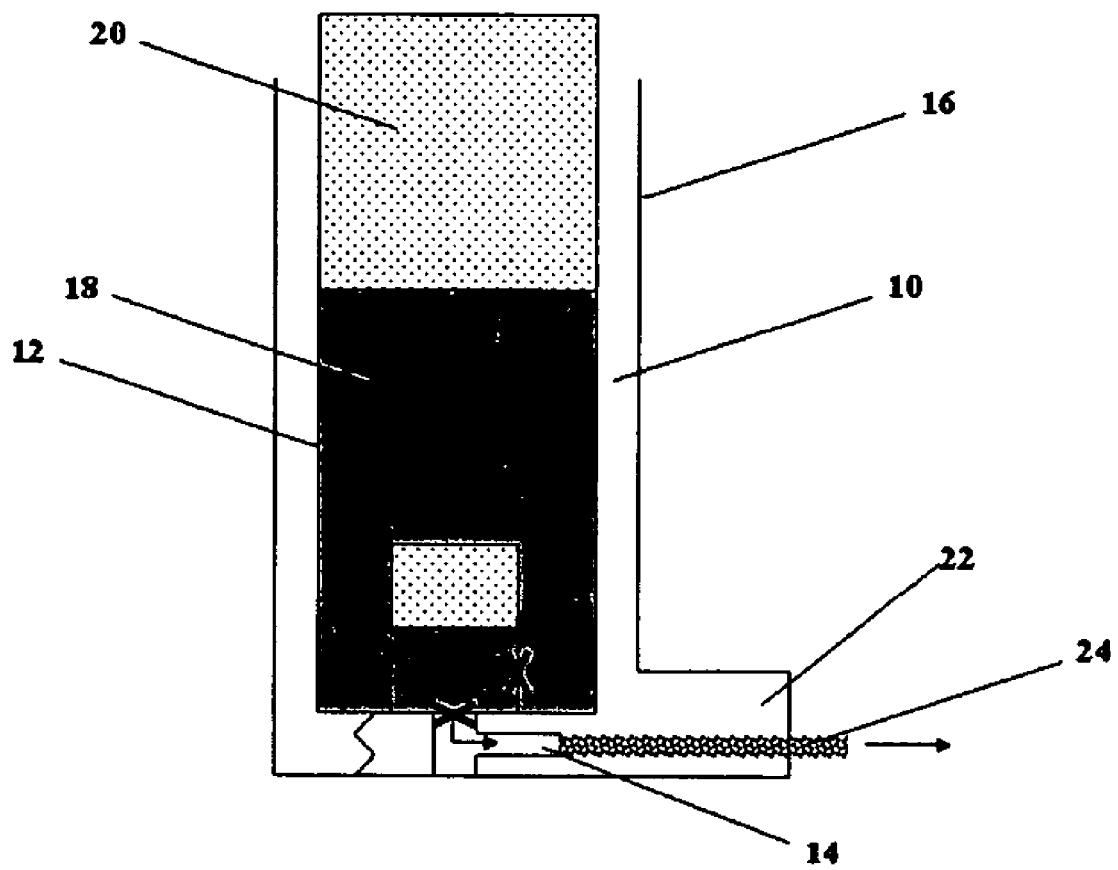
Figure 35:
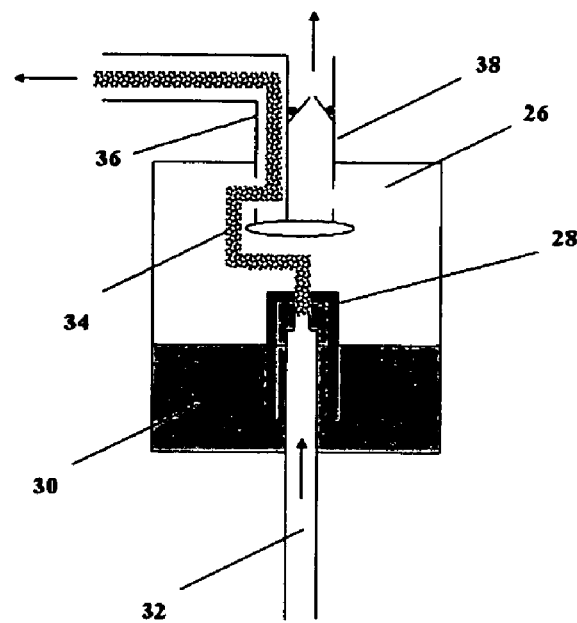
Figure 36:
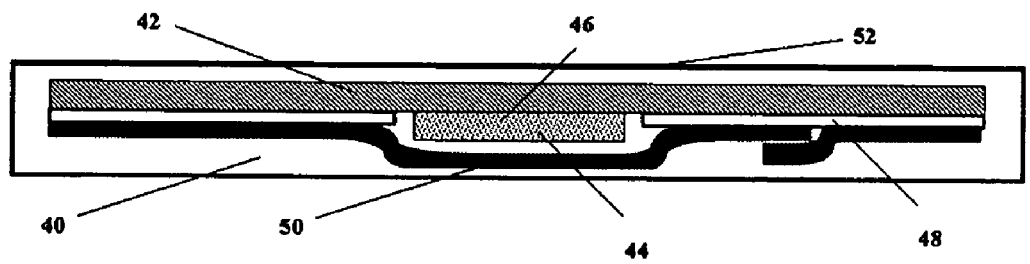
Figure 37:
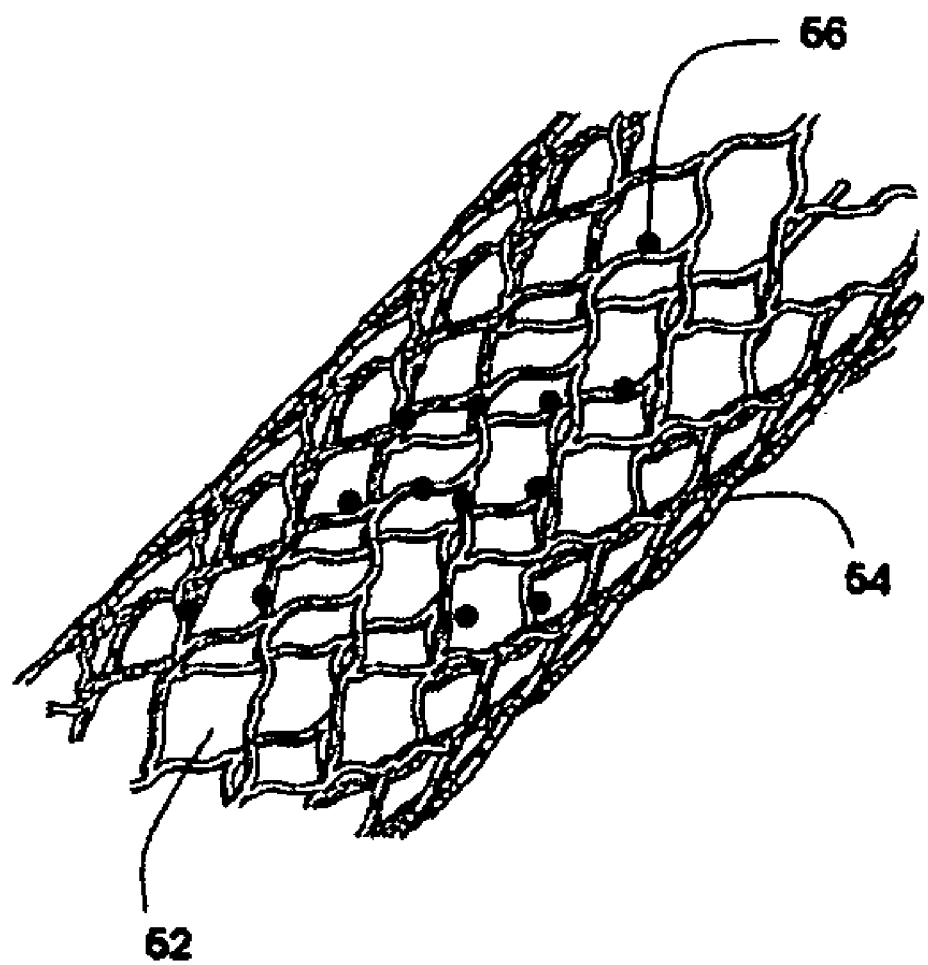

in isolated rat aorta pre-treated in vitro with 1 μM epinephrine (error bars represent the mean±standard errors);

FIG. 5 presents comparative plots demonstrating the superior (10-fold higher) vasorelaxation effect induced by of Pet-7 (n=4, diamonds), an exemplary NO-donor according to the present invention, as compared with glyceryltrinitrate (n=4, squares) in isolated rat aorta pre-treated in vitro with 1 μM epinephrine (error bars represent the mean±standard errors);

FIG. 6 presents comparative plots demonstrating the superior vasorelaxation effect induced by of Pet-8 (diamonds), an exemplary NO-donor according to the present invention, as compared with glyceryltrinitrate (squares) in isolated rat aorta pre-treated in vitro with 1 μM epinephrine (error bars represent the mean±standard errors);

FIG. 7 presents comparative plots demonstrating the vasorelaxation effect induced by of Pet-12 (Pet12-Ni, diamonds), an exemplary NO-donor according to the present invention, as compared with the corresponding pre-nitrated compound (Pet12, squares) in isolated rat aorta pre-treated in vitro with 1 μM epinephrine (error bars represent the mean±standard errors, n=6);

FIG. 8 presents comparative plots demonstrating the vasorelaxation effect induced by Pet-24 (diamonds), an exemplary NO-donor according to the present invention, as compared with glyceryltrinitrate (squares) in isolated rat aorta pre-treated in vitro with 1 μM epinephrine (error bars represent the mean±standard errors, n=4);

FIG. 9 presents comparative plots demonstrating the superior vasorelaxation effect induced by of Pet-43 (diamonds), an exemplary NO-donor according to the present invention, as compared with glyceryltrinitrate (squares) in isolated rat aorta pre-treated in vitro with 1 μM epinephrine (error bars represent the mean±standard errors, n=4);

FIG. 10 presents comparative plots demonstrating the superior vasorelaxation effect induced by of Pet-59 (diamonds), an exemplary NO-donor according to the present invention, as compared with glyceryltrinitrate (squares) in isolated rat aorta pre-treated in vitro with 1 μM epinephrine (error bars represent the mean±standard errors);

FIG. 11 presents comparative plots demonstrating the vasorelaxation effect induced by of Pet-147 (diamonds), an exemplary NO-donor according to the present invention, as compared with glyceryltrinitrate (squares) in isolated rat aorta pre-treated in vitro with 1 μM epinephrine (error bars represent the mean±standard errors);

FIG. 12 presents comparative plots demonstrating the superior vasorelaxation effect induced by of Pet-149 (diamonds), an exemplary NO-donor according to the present invention, as compared with glyceryltrinitrate (squares) in isolated rat aorta pre-treated in vitro contraction 1 μM epinephrine (error bars represent the mean±standard errors);

FIG. 13 presents comparative plots demonstrating the superior vasorelaxation effect induced by of Pet-152 (n=8, diamonds), an exemplary NO-donor according to the present invention, as compared with glyceryltrinitrate (n=4, squares) in isolated rat aorta pre-treated in vitro with 1 μM epinephrine (error bars represent the mean±standard errors);

FIG. 14 presents comparative plots demonstrating the vasorelaxation effect induced by of Pet-154 (n=8, diamonds), an exemplary NO-donor according to the present invention, as compared with glyceryltrinitrate (n=4, squares) in isolated rat aorta pre-treated in vitro with 1 μM epinephrine (error bars represent the mean±standard errors);

FIG. 15 presents comparative plots showing the vasorelaxation effect induced by GTN in isolated rat aorta pre-treated in vitro with epinephrine (control, squares) and in isolated rat aorta pre-treated in vitro with epinephrine and then with GTN (diamonds), and demonstrating the tolerance induced by treatment with GTN (error bars represent the mean±standard errors);

FIG. 16 presents comparative plots showing the vasorelaxation effect induced by Pet-3, an exemplary NO-donor according to the present invention, in isolated rat aorta pre-treated in vitro with epinephrine (control, diamonds) and in isolated rat aorta pre-treated in vitro with epinephrine and then with 0.44 mM Pet-3 (squares), and demonstrating the absence of tolerance induction following treatment with the NO-donors of the present invention, (error bars represent the mean±standard errors, n=4);

FIG. 17 presents comparative plots showing the vasorelaxation effect induced by Pet-7, an exemplary NO-donor according to the present invention, in isolated rat aorta pre-treated in vitro with epinephrine (control, diamonds) and in isolated rat aorta pre-treated in vitro with epinephrine and then with 0.44 mM Pet-7 (squares), and demonstrating the absence of tolerance induction following treatment with the NO-donors of the present invention, (error bars represent the mean±standard errors, n=4);

FIG. 18 presents comparative plots showing the vasorelaxation effect induced by Pet-12, an exemplary NO-donor according to the present invention, in isolated rat aorta pre-treated in vitro with epinephrine (control, diamonds) and in isolated rat aorta pre-treated in vitro with epinephrine and then with 0.44 mM Pet-12 (squares), and demonstrating the absence of tolerance induction following treatment with the NO-donors of the present invention (error bars represent the mean±standard errors);

FIG. 19 presents comparative plots showing the vasorelaxation effect induced by Pet-12 (diamonds), an exemplary NO-donor according to the present invention, and GTN (squares) in isolated rat aorta pre-treated in vitro with epinephrine and then with GTN, and demonstrating the absence of tolerance induction effect of the NO-donors of the present invention following treatment with GTN (error bars represent the mean±standard errors);

FIG. 20 presents comparative plots showing the vasorelaxation effect induced by Pet-12 (squares), an exemplary NO-donor according to the present invention, and GTN (squares) in isolated rat aorta pre-treated in vitro with epinephrine and then with Pet-12, and demonstrating the absence of tolerance induction effect of NO-donors of the present invention following treatment with Pet-12 (error bars represent the mean±standard errors);

FIG. 21 presents comparative plots showing the vasorelaxation effect induced by Pet-24, an exemplary NO-donor according to the present invention, in isolated rat aorta pre-treated in vitro with epinephrine (control, diamonds) and in isolated rat aorta pre-treated in vitro with epinephrine and then with 0.44 mM Pet-24 (squares), and demonstrating the absence of tolerance induction following treatment with the NO-donors of the present invention, (error bars represent the mean±standard errors);

FIG. 22 presents comparative plots showing the vasorelaxation effect induced by Pet-43, an exemplary NO-donor according to the present invention, in isolated rat aorta pre-treated in vitro with epinephrine (control, diamonds) and in isolated rat aorta pre-treated in vitro with epinephrine and then with 0.44 mM Pet-43 (squares), and demonstrating the absence of tolerance induction following treatment with the NO-donors of the present invention, (error bars represent the mean±standard errors);

FIG. 23 presents comparative plots showing the vasorelaxation effect induced by Pet-149, an exemplary NO-donor according to the present invention, in isolated rat aorta pre-treated in vitro with epinephrine (control, diamonds) and in isolated rat aorta pre-treated in vitro with epinephrine and then with 0.44 mM Pet-149 (squares), and demonstrating the absence of tolerance induction following treatment with the NO-donors of the present invention, (error bars represent the mean±standard errors);

FIG. 24 presents a bar graph showing the effect of GTN and Pet-2, an exemplary NO-donor according to the present invention, on the accumulation of cyclic-GMP (determined by radioimmunoassay) in isolated aorta of rats pre-treated in vivo with GTN and Pet-2 respectively, demonstrating the tolerance inducing effect of GTN and the absence of tolerance induction following administration of the NO-donors of the present invention (error bars represent the mean±standard errors, n=8);

FIG. 25 presents a bar graph showing the effect of GTN, Pet-3, Pet-7 and Pet-8, exemplary NO-donors according to the present invention, on the accumulation of cyclic-GMP (determined by radioimmunoassay) in isolated rat aorta, demonstrating the vasorelaxation effect of the NO-donors of the present invention (error bars represent the mean±standard errors, n=8);

FIG. 26 presents a bar graph showing the effect of Pet-12, an exemplary NO-donor according to the present invention, on the accumulation of cyclic-GMP (determined by radioimmunoassay) in isolated aorta of rats treated in vivo with Pet-12, demonstrating the absence of tolerance induction following administration of the NO-donors of the present invention (error bars represent the mean±standard errors, n=8);

FIG. 27 presents a bar graph showing the effect of GTN, Pet-24 and Pet-149, exemplary NO-donors according to the present invention, on the accumulation of cyclic-GMP (determined by radioimmunoassay) in isolated rat aorta, demonstrating the vasorelaxation effect of the NO-donors of the present invention (error bars represent the mean±standard errors, n=8);

FIG. 28 presents a graph demonstrating the vasorelaxation effect induced by 100 micrograms Pet-7, an exemplary NO-donor according to the present invention, on the heightened mean arterial blood pressure of rats pre-treated in vivo with 50 micrograms phenylephrine;

FIG. 29 presents a graph demonstrating the vasorelaxation effect induced by 50 micrograms Pet-12, an exemplary NO-donor according to the present invention, on the heightened mean arterial blood pressure of rats pre-treated in vivo with 50 micrograms phenylephrine;

FIG. 30 presents a graph demonstrating the vasorelaxation effect induced by 10 micrograms and thereafter by 50 micrograms Pet-12, an exemplary NO-donor according to the present invention, on the heightened mean arterial blood pressure of rats pre-treated in vivo with 10 micrograms phenylephrine;

FIG. 31 presents a graph demonstrating the vasorelaxation effect induced by 10 micrograms and thereafter by 50 micrograms Pet-13, an exemplary NO-donor according to the present invention, on the heightened mean arterial blood pressure of rats pre-treated in vivo with 10 micrograms phenylephrine;

FIG. 32 presents comparative plots demonstrating the superior vasorelaxation effect induced by of Pet-155 (n=8, diamonds), an exemplary NO-donor according to the present invention, as compared with glyceryltrinitrate (n=4, squares) in isolated rat aorta pre-treated in vitro with 1 μM epinephrine (error bars represent the mean±standard errors);

FIG. 33 presents a bar graph showing the effect of GTN, Pet-10, Pet-147, Pet-Pet-152, Pet-154 and Pet-155, exemplary NO-donors according to the present invention, on the accumulation of cyclic-GMP (determined by radioimmunoassay) in isolated rat aorta, demonstrating the vasorelaxation effect of the NO-donors of the present invention (error bars represent the mean±standard errors, n=8);

FIG. 34 presents a schematic illustration of a metered dose inhalator, an exemplary medical device according to the present invention;

FIG. 35 presents a schematic illustration of a nebulizer, an exemplary medical device according to the present invention;

FIG. 36 presents a schematic illustration of a skin patch, an exemplary medical device according to the present invention; and FIG. 37 presents a schematic illustration of a stent, an exemplary medical device according to the present invention.

DESCRIPTION OF THE PREFERRED EMBODIMENTS

The present invention is of a novel family of NO-donating compounds (NO-donors), which comprise one or more NO-releasing group(s) covalently attached to a chemical moiety, and which are designed such that when NO is released from the compound, a residue which is a naturally occurring metabolite is formed. The novel NO-donors of the present invention are highly efficacious and non-tolerance inducing and can therefore be beneficially used in the treatment of a variety of medical conditions such as, but not limited to, ischemic heart disease, heart failure, hypertension and other cardiovascular diseases and serve as bioregulators in physiological processes such as neurotransmission, blood clotting, blood pressure, and the destruction of cancerous tumor cells. The novel NO-donors of the present invention may further include a bioactive moiety (e.g., a drug) and thus may exert a dual therapeutic activity. The present invention is further of methods of preparing the novel NO-donors, pharmaceutical compositions including the NO-donors, medical devices designed for various modes of delivery the NO-donors and methods of using the NO-donors in the treatment of a variety of medical conditions.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is discussed hereinabove, organic nitrate and nitrite esters represent a time-honored class of NO-donating agents used in cardiovascular therapeutics since the nineteenth century. These agents have direct vasoactive effects and have therefore been used to treat ischemic heart disease, heart failure, and hypertension for many years. Growing evidence suggests that the cytochrome P-450 system, in conjunction with NADPH and glutathione-S-transferase activities, is required for the linked metabolic processes of denitration and reduction of organic nitrate esters to authentic NO [Kurz (1993) and McGuire (1998)].

However, as is further discussed hereinabove, treatment methods utilizing these compounds are severely limited by their therapeutic half-life, systemic absorption that is oftentimes accompanied by adverse hemodynamic effects, and, above all, critical drug tolerance. This phenomenon of tolerance (the loss of therapeutic efficacy upon repetitive administration) is by far the most predominant drawback of nitrate therapy, which limits their medicinal application.

In view of these limitations, substantial efforts have been made to develop and study novel NO-Donating agents. Unfortunately, most of these agents were characterized as tolerance-inducing following prolonged administration.

While conceiving the present invention, it was envisioned that overcoming the limitations associated with the presently known NO-donors could be achieved by the design and preparation of a novel class of NO-donors in which upon releasing a bioactive NO a residue of a naturally occurring metabolite is formed. It was further envisioned that such NO donors, when entering a biological system, would be subjected to enzymatic reactions that would result in the release of a bioactive NO and the formation of a residue of a metabolite, whereby this residue, by being derived from a naturally occurring metabolite, would be characterized by inherent biocompatibility, non-toxicity, and efficient absorption, distribution, excretion, metabolism and other biocompatibility related advantages. Above all, it was envisioned that the cleavage of such compounds into a residue that is characterized by such an inherent biocompatibility would prevent or decrease the development of tolerance to these compounds.

While further conceiving the present invention, it was envisioned that by conjugating a bioactive compound to the thiazole-derived NO-donors, combined and possibly synergistic therapeutic effects could be achieved, resulting from the dual therapeutic effect of the bioactive agent and the NO-releasing group.

While reducing the present invention to practice, a plurality of NO-donating compounds was designed according to the underlying principles outlined above and were readily synthesized. As is demonstrated in the Examples section that follows, these compounds were found highly efficacious in inducing vasorelaxation and reducing hypotension and were further found to be non-tolerance inducing in both in vitro and in vivo assays.

As used herein, the phrase "non-tolerance inducing compound(s)" is meant to describe compounds which upon repetitive administration thereof do not induce tolerance thereto.

The present invention therefore provides a novel class of NO-donating compounds, which are also referred to herein interchangeably as NO-donors. Each of the compounds of the present invention comprises an NO-releasing group, as is detailed hereinunder and a chemical moiety being covalently attached to the NO-releasing group.

As used herein, the phrase "chemical moiety" describes a residue, as this term is defined hereinbelow, of an organic substance.

The chemical moiety and the NO-releasing group are selected and attached one to the other such that upon release of NO from the compound, a residue of a naturally occurring metabolite is formed. As is discussed hereinabove, due to the formation of such a residue, the development of tolerance to the compounds of the present invention upon repetitive administration thereof is prevented or at least substantially decreased and hence the NO-donors of the present invention are highly advantageous and superior to the presently known NO-donors.

As used herein, the term "metabolite" describes a substance that is typically associated with one or more metabolic processes, that is, a substance produced by a metabolic process, required for a metabolic process and/or participating in a metabolic process.

As is further detailed hereinbelow, the NO-donating compounds according to the present invention optionally and preferably further comprise a bioactive agent residue. The bioactive residue is preferably attached, either directly or indirectly, preferably via a biocleavable moiety, to the chemical moiety in the compound.

While further conceiving the present invention, it was envisioned that exemplary NO-donating compounds as described above, which are designed to form a residue of vitamin B (thiamine) upon releasing NO, could be readily tailored and synthesized.

Vitamin $B_1$, a water soluble vitamin having the chemical name 3-[(4-amino-2-methyl-5-pyrimidinyl)methyl]-5-(2-hydroxyethyl)-4-methylthiazolium, is also known as thiamin, thiamine and aneurin. Thiamine is required by every cell of the body to process carbohydrates, fat, and protein and to form the fuel compound adenosine triphosphate (ATP).

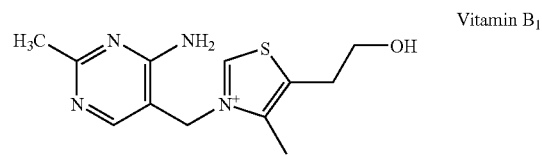

Vitamin $B_1$

Thiamin consists of a pyrimidine ring and a thiazole ring connected by a single-carbon bridging moiety, whereby the nitrogen in the thiazole ring being positively charged. It serves as a coenzyme for the decarboxylation of pyruvate and the oxidation of alpha keto-glutamic acid.

The enzyme thiamin pyrophosphatekinase and adenosine triphosphate (ATP) convert thiamin into its metabolically active coenzyme form, thiamin pyrophosphate (TPP), which is also referred to in the art as thiamine diphosphate (TDP) and cocarboxylase. The reaction center of TPP is the relatively acidic proton on carbon 2 of the thiazole ring, which has the capacity to form a carbanion, whereby the latter readily undergoes nucleophilic addition to carbonyl groups. In the form of TPP, thiamin functions in the oxidative decarboxylation of alpha-keto acids, such as pyruvate and alpha-ketoglutarate, as a coenzyme for alpha-ketoacid dehydrogenases. In addition TPP functions in the transketolase reaction of the pentose phosphate pathway as a coenzyme for transketolases. Both types of enzymes, alpha-ketoacid dehydrogenases and transketolases, cleave a carbon-carbon bond adjacent to a carbonyl group, releasing either carbon dioxide or an aldehyde. In the case of alpha-ketoacid dehydrogenases, the decarboxylation product is transferred to coenzyme A (CoA). Transketolases cleaves the carbon-carbon bond adjacent to the carbonyl group of an alpha-ketosugar to give an activated glycoaldehyde. The glycoaldehyde is then combined with an aldose molecule to yield a new ketose. All known TPP dependent enzymes also require a divalent cation, commonly $Mg^{2+}$.

Thiamine thus plays an important role in glucose metabolism and further appears to be involved in nerve transmission and/or excitation.

As thiamine is involved in numerous biological pathways, it was assumed that any residue thereof would be characterized by the inherent biocompatibility described above. It was further assumed that the metabolic pathways of vitamin B, described hereinabove could participate in releasing a bioactive NO from an NO-releasing group that is attached to a thiamine residue, similarly to the release of a phosphate group of TPP.

In view of the above, a representative model of NO-donating compounds according to the present invention, in which each of the compounds of the present invention comprises an NO-releasing group that is covalently attached to a thiamine-derived thiazole ring, has been designed.

Derivatives of thiazole are well-known in the art and are readily synthesized by well-established procedures. As is exemplified in the Examples section that follows, by selecting a suitable synthesis of a thiamine-derived thiazole, a variety of chemical parameters can be easily tailored, thus enabling the design and preparation of versatile thiazole-derived NO-donating compounds.

Hence, according to a preferred embodiment of the present invention, each of the NO-donating compounds described herein is designed such that upon release of NO, a residue of thiamine is formed. Each of the NO-donating compounds according to this embodiment of the present invention therefore include an NO-releasing group, as is detailed hereinunder, being covalently attached to a thiamine-derived thiazole ring.

Thiazole derivatives that include an NO-releasing group have only been reported hitherto in U.S. Pat. No. 6,677,374, which teaches nitrate ester-containing compounds for use as neuroprotective therapeutic agents. Two of the compounds disclosed in this patent include a thiazole ring: 1-(4-methylthiazol-5-yl)ethane-1,2-diyl dinitrate and 2-(4-methylthiazol-5-yl)ethyl nitrate. These compounds were prepared by nitrating two commercially available, arbitrarily selected, thiazoles, 5-(1,2-dihydroxyethyl)-4-methylthiazole and 4-methyl-5-(2-hydroxyethyl)thiazole. Nevertheless, this patent, by not being directed to NO-donating thiazole derivatives, fails to teach the design and preparation of various modifications of such derivatives, and particularly fails to address the beneficial effects of such derivatives in various applications and particularly the design and use of such thiazole derivatives as NO-donating compounds which prevent or decrease tolerance, due to the formation of a residue of a thiamine metabolite.

The NO-donating compounds according to this embodiment of the present invention include, for example, a thiamine nitrated derivative, in which the hydroxyl end group at position 5 has been replaced by a —$ONO_2$ group (see, for example, Pet-68 in Tables 1 and 2 below), and/or a pharmaceutically acceptable salt thereof.

Alternatively, the NO-donating compounds according to this embodiment of the present invention, include a thiamine analog, which has a thiamine-derived thiazole ring as its basic structural unit and/or a pharmaceutically acceptable salt thereof. Such NO-donating compounds according to the present invention are referred to herein interchangeably as thiazole-derived or thiazole-based compounds and are collectively represented by the general formula I:

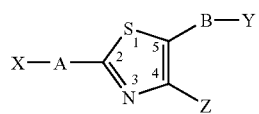

Formula I wherein:

A is selected from the group consisting of alkenyl, alkoxy, alkyl, alkynyl, amine, amine-oxide, aryl, aryloxy, azo, borate, C-amide, carbonyl, C-carboxylate, C-thiocarboxylate, cycloalkyl, diazo, disulfide, guanidine, guanyl, haloalkyl, heteroalicyclic, heteroaryl, hydrazine, N-amide, N-carbamate, N-dithiocarbamate, nitro, N-sulfonamide, N-thiocarbamate, O-carbamate, O-carboxylate, O-thiocarbamate, O-thiocarboxylate, oxime, oxygen, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, sulfur, thioalkoxy, thioaryloxy, thiocarbonyl, thiophosphate, thiosulfate, thiosulfite, thiourea, triphosphate, urea, a biocleavable moiety and any combination thereof, or absent;

X is selected from the group consisting of acyl halide, alkenyl, alkoxy, alkyl, alkynyl, amine, amine-oxide, aryl, aryloxy, azo, borate, C-amide, carbonyl, C-carboxylate, C-thiocarboxylate, cyano, cycloalkyl, diazo, disulfide, guanidine, guanyl, halide, haloalkyl, heteroalicyclic, heteroaryl, hydrazine, hydrogen, hydroxy, N-amide, N-carbamate, N-dithiocarbamate, nitro, N-sulfonamide, N-thiocarbamate, O-carbamate, O-carboxylate, O-thiocarbamate, O-thiocarboxylate, oxime, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, thioalkoxy, thioaryloxy, thiocarbonyl, thiohydroxy, thiophosphate, thiosulfate, thiosulfite, thiourea, triphosphate, urea, a bioactive agent residue, a moiety containing at least one NO-releasing group, a substituted or unsubstituted thiazole and any combination thereof;

B is selected from the group consisting of a saturated or unsaturated, substituted or unsubstituted alkylene chain having 1-20 carbon atoms, and a saturated or unsaturated, substituted or unsubstituted alkylene chain having 1-20 carbon atoms interrupted by at least one heteroatom, whereby the at least one heteroatom comprises oxygen, sulfur, nitrogen, phosphor, silicon and any combination thereof;

Y is an NO-releasing group; and

Z is selected from the group consisting of hydrogen, alkyl, alkenyl, alkynyl, amine, cycloalkyl, heteroalicyclic, aryl, heteroaryl, halide, haloalkyl, hydroxy, thiohydroxy, alkoxy, thioalkoxy, aryloxy and thioaryloxy.

It will be appreciated by one of skills in the art that the feasibility of each of the variables (denoted as A, B, X, Y and Z) to be located at the indicated positions depends on the valency and chemical compatibility of the substituent, the substituted position and other substituents. Hence, the present invention is aimed at encompassing all the feasible substituents for any position.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)$_2$—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR')R"— linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" describes a —O—Si(OR')(OR")(OR'") end group or a —O—Si(OR')(OR")— linking group, as these phrases are defined hereinabove, with R', R" and R'" as defined herein.

The term "boryl" describes a —BR'R" end group or a —BR'— linking group, as these phrases are defined hereinabove, with R' and R" are as defined herein.

The term "borate" describes a —O—B(OR')(OR") end group or a —O—B(OR')(O—) linking group, as these phrases are defined hereinabove, with R' and R" are as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

As used herein, the phrase "NO-releasing group" describes a chemical moiety, which is capable of generating NO either spontaneously or by means of chemical or enzymatic reactions. Representative examples of suitable NO-releasing groups according to the present invention include, without limitation, nitrate esters such as, for example, —$ONO_2$, S-nitrosothiol such as, for example, —SNO, diazeniumdiolates, also known as "NONOates" such as, for example, —N(NONO$^-$)— and —N(NONOH)—, and mesoionic oxatriazoles such as for example, 5-amino-[1,2,3,4]oxatriazol-2-ium and ,2,3,4-oxatriazolium-5-amino-3-(3,4-dichlorophenyl)-chloride. Preferably, the NO-releasing group in the compounds of the present invention, denoted as Y in the general Formula I above, is —$ONO_2$.

Thus, each of the compounds according to this embodiment of the present invention has a thiazole ring, to which an NO-releasing group is attached, preferably at position 5 of the ring. The NO-releasing group can be attached directly to the thiazole ring, or, preferably via a spacer.

The spacer, denoted as B in the general Formula I above, can be a saturated or unsaturated, substituted or unsubstituted hydrocarbon chain, and may optionally be interrupted by one or more heteroatom(s) such as oxygen, sulfur, nitrogen, phosphor, silicon and any combination thereof. When the heteroatom is nitrogen, phosphor or silicon, the heteroatom is preferably substituted by e.g., hydrogen, alkyl, halide, cycloalkyl or aryl, as these terms are defined hereinabove.

The chemical structure and length of the spacer may affect the biocompatibility, bioavailability, target specificity, and NO-releasing sensitivity of the compound.

According to preferred embodiments of this embodiment of the present invention, B is a non-substituted, saturated alkylene chain. Thus, B is preferably a non-substituted alkylene chain and, more preferably, a short alkylene chain such as, for example, methylene, ethylene and propylene. Since in the thiazole ring of Thiamine position 5 is substituted by a hydroxyethlene, more preferably, B is ethylene.

Alternatively, B can be a non-substituted, saturated alkylene chain interrupted by one heteroatom and can therefore be, for example, —$CH_2$—$CH_2$—O—$CH_2$— (methoxy ethylene), —$CH_2$—$CH_2$—NH—$CH_2$— (ethyl-methyl-amine) and —$CH_2$—$CH_2$—S—$CH_2$— (ethyl-methylsulfanyl).

The thiazole ring may be further substituted at position 4, by variable substituents, denoted as Z in the general Formula I above, which may also be selected so as to affect the compound's pharmacokinetic properties such as biocompatibility, bioavailability, solubility and target specificity.

Since in the thiazole ring of thiamine position 4 is substituted by a methyl, preferably Z is an alkyl, more preferably a lower alkyl such as methyl, ethyl and propyl, and more preferably, Z is methyl.

Each of the compounds according to this embodiment of the present invention further includes a moiety that is covalently attached to position 2 thereof. This moiety, denoted as X in the general Formula I above, can be a chemical moiety such as, for example, acyl-halide, alkenyl, alkoxy, alkyl, alkynyl, amine, amine-oxide, aryl, aryloxy, azo, borate, C-amide, carbonyl, C-carboxylate, C-thiocarboxylate, cyano, cycloalkyl, diazo, disulfide, guanidine, guanyl, halide, haloalkyl, heteroalicyclic, heteroaryl, hydrazine, hydrogen, hydroxy, N-amide, N-carbamate, N-dithiocarbamate, nitro, N-sulfonamide, N-thiocarbamate, O-carbamate, O-carboxylate, O-thiocarbamate, O-thiocarboxylate, oxime, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, thioalkoxy, thioaryloxy, thiocarbonyl, thiohydroxy, thiophosphate, thiosulfate, thiosulfite, thiourea, triphosphate, urea and any combination thereof. The attachment of such moieties may further affect the pharmacokinetic profile of the compound, as described hereinabove.

Optionally, X can be a moiety containing one or more NO-releasing group(s). Compounds in which X contains one or more NO-releasing group, in addition to the NO-releasing group in B (see, Formula I above), may exert enhanced capacity to elevate bioactive NO levels. Furthermore, the presence of more than one NO-releasing group in the same compound enables to incorporate therein different NO-releasing groups, which may be susceptible to more than one NO-releasing bio- and/or chemo-mechanism and thus further enhance the capacity of the compound to elevate NO levels.

As is detailed in the Examples section that follows, representative examples of compounds in which X is a moiety containing an NO-releasing group have been successfully prepared. These include 1,4-bis-[4-methyl-5-(2-nitrooxy)-ethyl)-thiazol-2-yl]-butane (Pet-13), bis-[4-methyl-5-(2-nitrooxy-ethyl)-thiazole-2-yl]-diazene (Pet-102) and 4,4'-dimethyl-5,5'-bis-(2-nitrooxy-ethyl)-[2,2']bithiazolyl (Pet-118) (see, Table 1).

Further optionally, X can be a thiazole, such that the compound contains two thiazole moieties attached therebetween. Such compounds may provide for additive advantageous effects of the thiazole residue, discussed hereinabove.

When X is a thiazole ring, the thiazole can be substituted or non-substituted. When substituted, each substituent can be, for example, alkyl, haloalkyl, alkenyl, alkynyl, cycloalkyl, heteroalicyclic, aryl, heteroaryl, amine, C-amide, N-amide, halide, acyl-halide, haloalkyl, sulfonate, sulfoxide, phosphonate, hydroxy, alkoxy, aryloxy, thiohydroxy, thioalkoxy, thioaryloxy, cyano, nitro, azo, N-sulfonamide, S-sulfonamide, C-carboxylate, O-carboxylate, C-thiocarboxylate, O-thiocarboxylate, N-carbamate, O-carbamate, N-thiocarbamate, O-thiocarbamate, S-dithiocarbamate, N-dithiocarbamate, urea, thiourea, guanyl, guanidine and hydrazine, as these terms are defined hereinabove.

Alternatively, one or more substituents can be a moiety containing an NO-releasing group, as described hereinabove. Such compounds may provide for additive advantageous effects of both the thiazole residues and the NO-releasing groups.

Further optionally and preferably, X is a bioactive agent residue.

The phrase "bioactive agent" is used herein to describe an agent capable of exerting a beneficial activity in a biological system (e.g., a living tissue or organ) of a subject. The beneficial activity includes, for example, a therapeutic activity per se, reduction of adverse side effects induced by another moiety or agent, and/or targeting and/or transportation of another moiety and/or agent towards a desired biological target.

The term "residue", as used in this context of the present invention, refers herein to a major portion of a molecule, which is covalently linked to another molecule, herein the chemical moiety (e.g., a thiamine-derived thiazole), or alternatively, is formed upon cleavage of another molecule.

Representative examples of bioactive agents that can be beneficially incorporated in the NO-donating compounds of the present invention include, without limitation, drugs, inhibitors, co-factors, co-enzymes, amino acids, peptides, proteins, hydroxamic acid, nicotinic acid, nicotinamide, carnitine, beta carotene, bromelain, non-steroidal anti-inflammatory drugs (NSAIDs), anti-psychotic agents, anti-thrombogenic agents, anti-platelet agents, anti-coagulants, anti-diabetics, growth factors, statins, toxins, antimicrobial agents, analgesics, metabolite agents, anti-metabolic agents, vasoactive agents, vasodilator agents, prostaglandins, hormones, thrombin inhibitors, enzymes, oligonucleotides, nucleic acids, antisenses, antibodies, antigens, vitamins, immunoglobulins, cytokines, cardiovascular agents, chemotherapeutic agents, antioxidants, phospholipids, anti-proliferative agents and heparins.

Non-limiting examples of non-steroidal anti-inflammatory drugs that can be beneficially incorporated in the NO-donors of the present invention include aspirin, celecoxib, diclofenac, diflunisal, etodolac, fenoprofen, flurbiprofen, ibuprofen, indomethacin, ketoprofen, ketorolac, meclofenamate, mefenamic acid, nabumetone, naproxen, oxaprozin, oxyphenbutazone, phenylbutazone, piroxicam, rofecoxib sulindac and tolmetin.

Non-limiting examples of anti-psychotic agents that can be beneficially incorporated in the NO-donors of the present invention include alprazolam, amantadine, amitriptyline, amoxapine, benztropine, bupropion, buspirone, calcium carbimide, carbamazepine, chlordiazepoxide, chlorpromazine, citalopram, clomipramine, clonazepam, clozapine, desipramine, dextroamphetamine, diazapam, diphenhydramine, disulfiram, divalproex, doxepin, edronax, ethosuximide, fluoxetine, flupenthixol, fluphenazine, flurazepam, fluvoxamine, haloperidol, imipramine, lamotrigine, lithium, lorazepam, loxapine, maprotiline, mesoridazine, methylphenidate, moclobemide, nefazodone, nortriptyline, olanzapine, oxazepam, paroxetine, pemoline, perphenazine, phenelzine, phenytoin, pipotiazine, primidone, propranolol, protriptyline, quetiapine, reboxetine, risperidone, sabril, sertraline, temazepam, thioridazine, tranylcypromine, trazodone, triazolam, trifluoperazine, trihexyphenidyl, trimipramine, valproate, venlafaxine, verapamil, vigabatrin, zopiclone and zuclopenthixol.

Non-limiting examples of cardiovascular agents that can be beneficially incorporated in the NO-donors of the present invention include adenosinea, alteplase, amiodarone, anagrelide, argatroban, atenolol, atorvastatin, benazepril, captopril, carvedilol, cerivastatin, clonidine, clopidrogel, diltiazem, enalapril, fluvastatin, fosinopril, gemfibrozil, hydrochlorothiazide, irbesartan, lisinopril, lovastatin, mibefradil, oprelvekin, pravastatin, prazosin, quinapril, ramipril, simvastatin, terazosin, valsartan and verapamil.

Non-limiting examples of metabolites that can be beneficially incorporated in the NO-donors of the present invention include glucose, urea, ammonia, tartarate, salicylate, succinate, citrate, nicotinate etc.

Non-limiting examples of anti-thrombogenic agents that can be beneficially incorporated in the NO-donors of the present invention include dipyridamole, tirofiban, aspirin, heparin, heparin derivatives, urokinase, rapamycin, PPACK (dextrophenylalanine proline arginine chloromethylketone), probucol, and verapamil.

Non-limiting examples of chemotherapeutic agents that can be beneficially incorporated in the NO-donors of the present invention include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine and vinblastine, and derivatives thereof; sulfhydryl containing chemotherapeutic agents and carboxyl containing chemotherapeutic agents.

Non-limiting examples of antimicrobial agents that can be beneficially incorporated in the NO-donors of the present invention include iodine, chlorhexidene, bronopol and triclosan.

Non-limiting examples of vitamins that can be beneficially incorporated in the NO-donors of the present invention include vitamin A, thiamin, vitamin $B_6$, vitamin $B_{12}$, vitamin C, vitamin D, vitamin E, vitamin K, riboflavin, niacin, folate, biotin and pantothenic acid.

Non-limiting examples of anti-diabitics that can be beneficially incorporated in the NO-donors of the present invention include lipoic acid, acarbose, acetohexamide, chlorpropamide, glimepiride, glipizide, glyburide, meglitol, metformin, miglitol, nateglinide, pioglitazone, repaglinide, rosiglitazone, tolazamide, tolbutamide and troglitazone.

The conjugation of a bioactive agent to a group having an NO-releasing group attached thereto is highly beneficial since it may provide for combined and even synergistic therapeutic effects of both the NO-releasing group and the bioactive agent.

These combined therapeutic effects are particularly advantageous when the bioactive agent is associated with NO-deficiency related impairment, namely, an administration of the bioactive agent to a subject, which adversely causes NO-deficiency. Examples of such bioactive agents which adversely cause NO-deficiency include, without limitation, anti-psychotic agents, cardiovascular agents and particularly non-steroidal anti-inflammatory agents (NSAIDs).

Thus, according to a preferred embodiment of the present invention, the bioactive agent residue (X on Formula I above) is a non-steroidal anti-inflammatory drug residue.

Non-steroidal anti-inflammatory drugs (NSAIDs) are widely used as anti-inflammatory, analgesic and antipyretic for the treatment of pain, fever, and inflammation. Chronic NSAID therapy effectively reduces the symptoms of many painful arthritic syndromes, but is oftentimes associated with adverse gastrointestinal (GI) complications [Cash, J. M.; Klippel, J. H. *New Engl. J. Med,* 1994, 330, 1368; Davies, N. M., Wallace, J. L. *J. Gastroenterol.*, 1997, 32, 127; Wallace, *J. Gastroenterol.*, 1997, 112, 1000], as well as high blood pressure and heart diseases. At the tissue level, the most common clinical manifestation of NSAID-related GI damage is a combination of gastroduodenal erosions and ulcerations often called NSAID-induced gastropathy, affecting at least 25% of chronic NSAID patients. NSAID-induced gastropathy may limit long-term NSAID therapy and cause a significant financial burden to the healthcare system.

In vivo NO generation has become the prime therapeutic target for reducing NSAID induced gastropathy associated with chronic NSAID use. A recently published data have shown that NO-donors effectively reduce gastric mucosal damage and may facilitate GI healing following chemical insult [Ko, J. K.; Cho, C. H. *Inflamm. Res.*, 1999, 48, 471]. As first conceptualized by Wallace and colleagues [Reuter, B., Wallace, J. L. A therapeutic application of nitric oxide: GI-sparing NSAIDs. In: Nitric Oxide: A Modulator of Cell-Cell Interactions in the Microcirculation. (P. Kubes, ed.) R.G. Landes Company, 1995, pp. 157-168], modern drug discovery has focused on one general approach in an attempt to utilize the therapeutic potential of NO against NSAID-induced gastric damage: covalent modification of NSAIDs with NO-releasing moieties [Brzozowski T., et al., *Dig Liver Dis.* 2000 32(7), pp 583-94].

Due to the beneficial effect of compounds that can act as both NO-donors and anti-inflammatory agents, delineated above, the present inventors have designed and successfully prepared representative thiazole-based compounds, according to this embodiment of the present invention, which have a NSAID residue attached thereto (for example, as X in Formula I above). These include 2-[1-(6-methoxy-naphthalen-2-yl-ethyl]-4-methyl-5-(2-nitrooxy-ethyl)-thiazole (Pet 17), wherein X is a naproxen residue, 2-[1-(4-isobutyl-phenyl)-ethyl]-4-methyl-5-(2-nitrooxy-ethyl)-thiazole (Pet-66) wherein X is an ibuprofen residue and acetic acid 2-[4-methyl-5-(2-nitrooxy-ethyl)-thiazol-2-yl]-phenyl ester (Pet-116) wherein X is an aspirin residue (see, Tables 1 and 2).

As is demonstrated in the Examples section that follows, these novel compounds exert high NO-releasing efficacy, are non-tolerance inducing and therefore further exert the protective effect required to improve the safety and pharmacokinetic profile of the NSAID agent residue attached thereto.

The combined therapeutic effects mentioned above are further advantageous when the condition that is treatable by the bioactive agent is further associated with NO-deficiency and/or may lead to clinical manifestations in which elevating the NO level is beneficial. An example of such a condition is diabetes.

Thus, according to preferred embodiments of the present invention, the bioactive agent residue (X in Formula I above) is an anti-diabetic agent residue, as is detail hereinabove.

The link between diabetes mellitus and vascular diseases has been well established in many studies, indicating that the main etiology for mortality and a great percent of morbidity in patients with diabetes mellitus is atherosclerosis (Calles-Escandon, J. and M. Cipolla (2001), *Endocr. Rev.* 22(1): 36-52). The reciprocity between insulin and NO productions, as well as blood-circulation irregularities and systemic low NO-levels that are typically associated with diabetes, accentuate the interrelationship between diabetes of all types and NO deficiency.

Thus, it was found that narrowing of blood vessels due to increased synthesis of type IV collagen by vascular cells adjacent to the membrane occurs in response to hyperglycaemia, hyperinsulinaemia, and other factors associated with diabetes (Sharma K. et al., (1996), *Diabetes,* 45: 522-30). There are also evidences that the vasodilatation activity of insulin may be partly mediated by local and systemic NO levels, and vice versa (Scherrer U. et al., (1994) *J. Clin Invest;* 94: 2511-15).

In addition, NO deficiency is prevalent in people with diabetes. Both Type I and Type II diabetic patients have a reduced ability to generate NO from L-arginine, reflected in part by direct measurements of plasma nitrate and nitrite levels. This is mainly attributed to the malfunctioning of NOS, which, in turn, results from reduction in the elimination of a natural inhibitor of NOS (asymmetrical dimethyl arginine, ADMA) due to reduced kidney function, impaired blood circulation and hence inadequate oxygen levels which leads to impaired NO-generation by NOS, and an acidic pH which adversely affect NOS activity, all are observed in patients having diabetes.

Hence, since it is well established that elevating the NO level while treating a patient having diabetes is known to be beneficial, the present inventors have designed and successfully prepared representative thiazole-based compounds, according to this embodiment of the present invention, which have an anti-diabetic agent residue attached thereto (for example, as X in Formula I above). These include 2-(4-[1,2]dithiolan-3-yl-butyl)-4-methyl-5-(2-nitrooxyethyl)-thiazole (Pet-67) and 5-[1,2]dithiolan-3-yl-pentanoic acid [4-methyl-5-(2-nitrooxy-ethyl)-thiazol-2-yl]-amide (Pet-151), in which X is a lipoic acid residue (see, Tables 1 and 2). As is well known in the art, lipoic acid is a therapeutically active agent that is used as a food supplement to assist in the combat against diabetes.

Each of the bioactive agent residues described above (for example, X in Formula I above) can be attached to the chemical moiety (e.g., the thiamine-derived thiazole ring) either directly or indirectly. When attached indirectly, the bioactive agent is attached to the chemical moiety (e.g., the thiazole ring) via a linking moiety, represented, for example, as A in Formula I above.

The linking moiety (e.g., A in Formula I) can be, for example, alkenyl, alkoxy, alkyl, alkynyl, amine, amine-oxide, aryl, aryloxy, azo, borate, C-amide, carbonyl, C-carboxylate, C-thiocarboxylate, cycloalkyl, diazo, disulfide, guanidine, guanyl, haloalkyl, heteroalicyclic, heteroaryl, hydrazine, N-amide, N-carbamate, N-dithiocarbamate, nitro, N-sulfonamide, N-thiocarbamate, O-carbamate, O-carboxylate, O-thiocarbamate, O-thiocarboxylate, oxime, oxygen, peroxo, phosphate, phosphine-oxide, phosphine-sulfide, phosphinyl, phosphite, phosphonate, pyrophosphate, S-dithiocarbamate, silaza, silicate, siloxy, silyl, S-sulfonamide, sulfate, sulfite, sulfonate, sulfoxide, sulfur, thioalkoxy, thioaryloxy, thiocarbonyl, thiophosphate, thiosulfate, thiosulfite, thiourea, triphosphate, urea, a biocleavable moiety and any combination thereof, or absent.

According to a preferred embodiment of the present invention, the linking moiety (e.g., A in Formula I) is a biocleavable moiety.

As used herein, the phrase "biocleavable moiety" describes a chemical moiety, which undergoes cleavage in a biological system such as, for example, the digestive system of an organism or an enzymatic system in a living cell. Representative examples of biocleavable moieties include, without limitation, amides, carboxylates, carbamates, phosphates, hydrazides, thiohydrazides, disulfides, epoxides, peroxo and methyleneamines. Such moieties are typically subjected to enzymatic cleavages in a biological system, by enzymes such as, for example, hydrolases, amidases, kinases, peptidases, phospholipases, lipases, proteases, esterases, epoxide hydrolases, nitrilases, glycosidases and the like.

As used herein, the term "hydrazide" describes a —C(=O)—NR'—NR"R''' end group or a —C(=O)—NR'—NR"— linking group, as these phrases are defined hereinabove, where R', R" and R''' are as defined herein.

As used herein, the term "thiohydrazide" describes a —C(=S)—NR'—NR"R''' end group or a —C(=S)—NR'—NR"— linking group, as these phrases are defined hereinabove, where R', R" and R''' are as defined herein.

As used herein, the term "epoxide" describes a

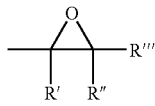

end group or a

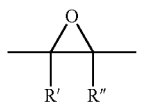

linking group, as these phrases are defined hereinabove, where R', R" and R''' are as defined herein.

As used herein, the term "methyleneamine" describes an —NR'—CH$_2$—CH=CR"R''' end group or a —NR'—CH$_2$—CH=CR"— linking group, as these phrases are defined hereinabove, where R', R" and R''' are as defined herein.

As discussed hereinabove, some preferred NO-donors according to the present invention have a bioactive agent residue attached thereto and therefore offer exceptional advantages due to the dual functionality thereof (elevating the NO level by an NO-releasing group and exerting a beneficial activity by the bioactive agent). Incorporation of a biocleavable moiety which links between the bioactive agent residue and the chemical moiety attached to the NO-releasing group (e.g., a nitrated thiamine-derived thiazole ring) in such compounds provides for a release of the bioactive agent in a biological system and thus may improve the biological activity of both the NO-releasing part of the compound and the bioactive agent.

Thus, according to another preferred embodiment of the present invention, the NO-donating compounds according to the present invention include a bioactive agent (e.g., X in Formula I), which is attached to the chemical moiety via a biocleavable moiety (e.g., A in formula I).

As is demonstrated in the Examples section that follows, representative examples of thiamine-derived thiazole-based NO-donating compounds in which A is a biocleavable moiety and X is a bioactive residue have been successfully prepared. These include, for example, 4-[1,2]dithiolan-3-yl-N-[4-methyl-5-(2-nitrooxy-ethyl)-thiazol-2-yl]-butyramide (Pet-151) wherein A is an amide and X is a residue of 5-[1,2]dithiolan-3-yl-pentanoic acid, also known as lipoic acid, and have been suggested as a therapeutic and prophylactic treatment of many age-related diseases, from heart disease and stroke to diabetes and cataracts, 4-methyl-5-(2-nitrooxy-ethyl)-thiazole-2-carboxylic acid N'-phthalazin-1-yl-hydrazide (Pet-153) wherein A is a hydrazide and X is phthalazine-1-yl, N-[4-Methyl-5-(2-nitrooxy-ethyl)-thiazol-2-yl]-nicotinamide (Pet-154) wherein A is an amide and X is a nicotinic acid residue, allyl-[4-methyl-5-(2-nitrooxy-ethyl)-thiazol-2-yl]-amine (Pet-155) wherein A is an amine and X is allyl (H$_2$C=CH—CH$_2$—), N-[4-methyl-5-(2-nitrooxy-ethyl)-thiazol-2-yl]-1-oxy-nicotinamide (Pet-156) wherein A is an amide and X is an oxidized nicotinic acid residue (pyridine 1-oxide-3-yl), hexadecanoic acid [4-methyl-5-(2-nitrooxy-ethyl)-thiazol-2-yl]-amide (Pet-158) wherein A is an amide and X is 1-pentadecanyl (fatty acid), and 10,13-dimethyl-3-oxo-2,3,6,7,8,9,10,11,12,13,14,15,16,17-tetradecahydro-1H-cyclopenta[a]phenanthren-17-yl ester (Pet-164) wherein A is an amide and X is a hormone residue.

Other exemplary thiamine-derived thiazole-based NO-donating compounds in which A is a biocleavable moiety which have been successfully prepared include 4-acetylamino-N-[4-methyl-5-(2-nitrooxy-ethyl)-thiazol-2-yl]-benzamide (Pet-157); pyrrolidine-2-carboxylic acid [4-methyl-5-(2-nitrooxy-ethyl)-thiazol-2-yl]-amide (Pet-160); 2,6-difluoro-N-[4-methyl-5-(2-nitrooxy-ethyl)-thiazol-2-yl]-benzamide (Pet-161); 2-(2,4-dichloro-phenyl)-N-[4-methyl-5-(2-nitrooxy-ethyl)-thiazol-2-yl]-acetamide (Pet-162); and 2-(2,4-dichloro-phenoxy)-N-[4-methyl-5-(2-nitrooxy-ethyl)-thiazol-2-yl]-acetamide (Pet-163).

As is further discussed hereinabove, NO-donors according to the present invention in which the bioactive agent residue is a NSAID residue are highly beneficial and hence attaching the NSAID residue to the thiazole ring that contains an NO-releasing moiety would be highly advantageous. Thus, in another preferred embodiment of the present invention, A is a biocleavable moiety and X is a NSAID residue.

As is demonstrated in the Examples section that follows, representative examples of compounds in which A is a biocleavable moiety and X is a NSAID residue have been successfully prepared. These include 2-(6-methoxy-naph-thalen-2-yl)-N-[4-methyl-5-(2-nitrooxy-ethyl)-thiazol-2-yl]-propionamide (Pet-150), where A is an amide and X is a naproxen residue, 2-(4-isobutyl-phenyl)-N-[4-methyl-5-(2-nitrooxy-ethyl)-thiazol-2-yl]-propionamide (Pet-152) where A is an amide and X is an ibuprofen residue and acetic acid 2-[4-methyl-5-(2-nitrooxy-ethyl)-thiazol-2-ylcarbamoyl]-phenyl ester (Pet-159) wherein A is an amide and X is an Aspirin residue (2-acetobenzene-1-yl).

The chemical structures of preferred compounds according to this embodiment of the present invention are set forth in Table 1 below. A list of preferred compounds according to the present invention is set forth in Table 2 below.

The present invention further encompasses any pharmaceutically acceptable salts of the NO-donating compounds described herein.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The present invention further encompasses prodrugs, solvates and hydrates of the NO-donating compounds described herein.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be the NO-donating compound, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the NO-donating compound) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Chemical Syntheses:

Further according to the present invention, there is provided a process of preparing the novel NO-donors of the present invention described hereinabove, and particularly the preferred thiazole-based NO-donors described hereinabove. The process is effected as follows:

As a starting material, a suitable thioamide, which includes the moieties A and X described hereinabove and is represented by the general Formula II below is provided.

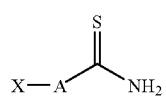

Formula II

Some suitable thioamides according to the present invention are commercially available or can be readily prepared. These include, without limitation, N,N-dimethylthiourea, thiobenzamide, thiourea, N-allylthiourea, acetylthiourea, N-ethylthiourea, N,N-dimethylthiourea, alpha-naphthylthiourea, 1-[(3,5-bis-trifluoromethyl)phenyl]thiourea and dithiooxalamide.

Other thioamides can be readily synthesized by converting a corresponding amide thereto. The selected amide preferably has the general formula V below.

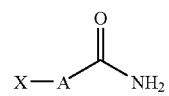

Formula V

Some suitable amides according to the present invention are commercially available or can be prepared according to procedures known in the art. These include, without limitation, propionamide, acetamide, isobutyramide, L-(−)-lactamide, trifluoroacetamide, carbamic acid methyl ester, hexanedioic acid diamide, piperidine-4-carboxylic acid amide, thionicotinamide, naproxenamide, 4-(trifluoromethyl)-thiobenzamide, azodicarbonamide, 2-(4-isobutyl-phenyl)-propionamide, isonicotinamide, 2,2,2-trifluoroacetamide, glycinamide, 4-aminobenzamide, 2,3,4,5,6-pentafluorobenzamide, 2-aminobenzamide, ethyloxamate, 2,6-difluorobenzamide, N-phenylurea, 2,4-dichlorophenylacetamide, 2,4-dichlorophenoxyacetmide, 2-phenylbutyamide, azodicarbonamide, 3,5-difluorobenzamide, DL-lipoamide, Rubeanic acid, adpamide, aalonamide, acrylamide and 2-hydroxy-benzamide.

Converting the selected amide to a thioamide is preferably effected by reacting the thioamide with a thiolating agent. The thiolating agent can be any of those known in the art. Preferably, the thiolating agent is phosphorous pentasulfide.

The thioamide is then reacted with a suitable reactive compound, to thereby form, via a typical condensation reaction, a derivatized thiazole ring.

Suitable reactive compounds for this purpose are those having the general Formula III:

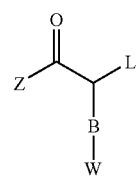

Formula III in which B and Z are as defined hereinabove, L is a leaving group and W is a pre-nitratable group.

As used herein, the phrase "leaving group" describes a labile atom, group or chemical moiety that readily undergoes detachment from an organic molecule during a chemical reaction, while the detachment is facilitated by the relative stability of the leaving atom, group or moiety thereafter. Typically, any group that is the conjugate base of a strong acid can act as a leaving group. Representative examples of suitable leaving groups according to the present invention therefore include, without limitation, acetate, tosylate, hydroxy, thiohydroxy, alkoxy, halide, amine, azide, cyanate, thiocyanate, nitro and cyano. Preferably, the leaving group L is a halide, and most preferably it is chloride.

The phrase "pre-nitratable group", as used herein, describes a chemical moiety that can be converted to a nitratable group, as this term is defined hereinbelow. The conversion can be effected either spontaneously during the condensation reaction described above, or non-spontaneously, via an additional reaction. The pre-nitratable group can be, for example, a protected nitratable group, which undergoes deprotection and thus converted to a nitratable group during a reaction. Preferably, the pre-nitratable group according to the process of the present invention is spontaneously converted into a nitratable group during the reaction of the reactive compound with the thioamide.

The reactive compound having the Formula III is therefore selected so as to have the desired B and Z moieties in the resulting NO-donating compound and a pre-determined pre-nitratable group, which is thereafter converted into the desired NO-releasing group in the resulting compound, as is detailed hereinunder.

An example of a readily synthesizable reactive compound that can be advantageously used in the process of the present invention is 5-acetoxy-3-chloro-2-pentanone.

Upon reacting the thioamide and the reactive compound having Formula III, a derivatized thiazole, having the general Formula IV below, is obtained.

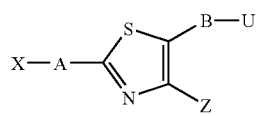

Formula IV

In general Formula IV, A, X, Z and B are as defined hereinabove and U is a nitratable group.

As used herein, the phrase "nitratable group" describes a chemical moiety, which can be readily converted to a NO-releasing group, as this phrase is defined hereinabove, preferably by reacting it with a nitrating agent.

Representative examples of nitratable groups according to the present invention are hydroxyl and thiohydroxyl. The hydroxyl or thiohydroxyl group can be reacted with nitric acid, any derivative thereof or any compound that includes a nitric acid residue, preferably under acidic conditions, to thereby produce an NO-releasing group.

In cases where the nitratable group according the present invention is hydroxy, or a thiohydroxy group the pre-nitratable group in Formula III above can be, for example, a carboxylate, as this term is defined hereinabove, such as acetate. Under suitable reaction conditions, the acetate is spontaneously converted to hydroxy during the reaction between the thioamide and the reactive compound of Formula III.

The derivatized thiazole having general Formula IV is then reacted so as to convert the nitratable group into a NO-releasing group. This conversion is preferably effected by reacting the thiazole derivative with a nitrating agent, which contains the NO-releasing group.

Suitable nitrating agents include, for example, nitric acid, which is used to provide an —ONO$_2$ NO-releasing group, and nitric oxide and oxygen, which are used to provide NONOates.

Exemplary conditions and procedures, which can be used in the process described above, are described in detail in the Examples section that follows.

As is further shown in the Examples section that follows, using the process according to this aspect of the present invention a variety of NO-donors according to the present invention have been successfully prepared and characterized. These include, for example, 2-Ethyl-4-methyl-5-(2-nitrooxy-ethyl)-thiazole (Pet-2), 2,4-Dimethyl-5-(2-nitrooxy-ethyl)-thiazole (Pet-3), 2-Isopropyl-4-methyl-5-(2-nitrooxy-ethyl)-thiazole (Pet-4), 4-Methyl-5-(-2-nitrooxy-ethyl)-2-(1-nitrooxy-ethyl-thiazole (Pet-5), 4-Methyl-5-(nitrooxy-ethyl)-2-trifluoromethyl-thiazole (Pet-6), dimethyl-[4-methyl-5-(2-nitrooxy-ethyl)-thiazol-2-yl]-amine (Pet-7), 4-methyl-5-(2-nitrooxy-ethyl)-2-phenyl-thiazole (Pet-8), 2-methoxy-4-methyl-5-(2-nitrooxy-ethyl)-thiazole (Pet-9), 4-methyl-5-(2-nitrooxy-ethyl)-thiazole-2-ylamine (Pet-10), 4-[4-methyl-5-(2-nitrooxy-ethyl)thiazole-2-yl]-piperidine (Pet-11), 3-[4-methyl-5-(2-nitrooxy-ethyl)-thiazole-2-yl]-pyridine (Pet-12), 1,4-Bis-[4-Methyl-5-(2-nitrooxy)-ethyl)-thiazol-2-yl]-Butane (Pet-13), 2-[1-(6-methoxy-naphthalen-2-yl-ethyl]-4-methyl-5-(2-nitrooxy-ethyl)-thiazole (Pet-17), 4-methyl-5-(2-nitrooxy-ethyl)-2-(4-trifluoromethyl-phenyl)-thiazole (Pet-59), 2-[1-(4-isobutyl-phenyl)-ethyl]-4-methyl-5-(2-nitrooxy-ethyl)-thiazole (Pet-66), acetic acid 2-[4-methyl-5-(2-nitrooxy-ethyl)-thiazol-2-yl]-phenyl ester (Pet-116), 4,4'-dimethyl-5,5'-bis-(2-nitrooxy-ethyl)-[2,2']bithiazolyl (Pet-118), 2-(3,5-difluoro-phenyl)-4-methyl-5-(2-nitrooxy-ethyl)-thiazole (Pet-181) 4-chloro-1-methoxy-benzen-2-yl, 2-(5-chloro-2-methoxy-phenyl)-4-methyl-5-(2-nitrooxy-ethyl)-thiazole (Pet-182), N-[4-methyl-5-(2-nitrooxy-ethyl)-thiazol-2-yl]-guanidine (Pet-183), N-(2-chloro-benzylidene)-N'-[4-methyl-5-(nitrooxy-ethyl)-thiazol-2-yl]-hydrazine (Pet-184), (4-chlorophenyl)-[4-methyl-5-(2-nitrooxy-ethyl)-thiazol-2-yl]-amine (Pet-185) and (3,5-dichloro-phenyl)-[4-methyl-5-(2-nitrooxy-ethyl)-thiazol-2-yl]-amine (Pet-186) (see, Table 1).

As is discussed in detail hereinabove, some of the presently preferred compounds according to the present invention have a biocleavable moiety (A) linking between X and the thiazole ring (see, Formula I above). Due to the cleavable nature of the biocleavable moiety, a different process has been developed and successfully used for preparing such compounds.

Hence, according to still another aspect of the present invention there is provided a process of preparing the NO-donors of the present invention described hereinabove and presented in Formula I above, in which A is a biocleavable moiety, as defined hereinabove. The process, according to this aspect of the present invention is effected as follows:

Using the synthetic strategy described above for obtaining the thiazole derivative having the general Formula IV, suitable thioamides (Formula II above) and reactive compounds having Formula III above are reacted so as to provide a derivatized thiazole having the general Formula VI:

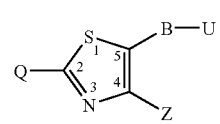

Formula VI wherein B, U and Z are as defined hereinabove, and Q is a first reactive group, as is defined and detailed hereinbelow.

Such a thiazole derivative is preferably obtained by selecting an amide or a thioamide, which has the general Formula VIII or IX, respectively:

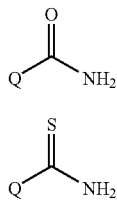

Formula VIII

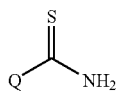

Formula IX

The first reactive group Q in the amide or thioamide starting materials is preferably protected by a suitable protecting group when the materials are reacted to form the derivatized thiazole (Formula VI) and is thereafter deprotected. Any of the commonly used protecting groups can serve as protecting groups in this embodiment of the present invention, depending on the selected reactive group and the reaction conditions.

A reactive derivative of X, which has the general Formula VII below, is further provided.

X—K    Formula VII

In Formula VII, X is as defined above and K is a second reactive group, as is defined hereinbelow.

The compound of Formula VII can be a commercially available compound or can be prepared using commonly known synthetic strategies, depending on the selected X and K.

As used herein, the phrase "reactive group", which refers to both the first and the second reactive groups, describes a chemical moiety that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, cycloaddition reactions, rearrangement reactions and any other known organic reactions that involve a reactive group.

Representative examples of suitable reactive groups according to the present invention include, without limitation, amine, halide, acyl-halide, sulfonate, sulfoxides, phosphate, hydroxy, alkoxy, aryloxy, thiohydroxy, thioalkoxy, thioaryloxy, cyano, nitro, azo, isocyanate, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine, as these terms are defined hereinabove.

The first and the second reactive groups are preferably selected as being capable to react one with the other, to thereby form the desired biocleavable moiety.

Thus, for example, amine and hydroxy are selected as the first and second reactive groups or, vice versa, as the second and first reactive groups, so as to form an amide as the biocleavable moiety; a carboxylate or acyl-halide and hydroxy are selected so as to form a carboxylate-type biocleavable moiety; two thiohydroxy groups are selected so as to form a disulfide biocleavable moiety, an isocyanate and a hydroxy are selected so as to form a carbamate-type biocleavable moiety; and a hydrazine and a carboxylic acid are selected so as to form a hydrazide-type biocleavable moiety.

The phrase "carboxylate-type biocleavable moiety" includes a carboxylate linking group, as defined hereinabove, and any derivative thereof, such as, for example, thiocarboxylate.

The phrase "carbamate-type biocleavable moiety" includes a carbamate linking group, as defined hereinabove, and any derivative thereof, such as, for example, thiocarbamate.

The phrase "hydrazide-type biocleavable moiety" includes a hydrazide linking group, as defined hereinabove, and any derivative thereof, such as, for example, thiohydrazide.

The thiazole derivative and the compound of Formula VII are then reacted, under suitable conditions which enable the formation of a bond between the first and the second reactive groups, to thereby provide a derivatized thiazole having the general Formula IV, as described hereinabove.

The nitratable group in the derivatized thiazole is then converted, as described hereinabove, to the NO-releasing group, so as to provide the desired NO-donor according to this embodiment of the present invention.

As is demonstrated in the Examples section, using the process according to this aspect of the present invention, a variety of NO-donors according to the present invention, which have a biocleavable moiety, have been successfully prepared. These include, for example, 2-(6-methoxy-naphthalen-2-yl)-N-[4-methyl-5-(2-nitrooxy-ethyl)-thiazol-2-yl]-propionamide (Pet-150), 4-[1,2]dithiolan-3-yl-N-[4-methyl-5-(2-nitrooxy-ethyl)-thiazol-2-yl]-butyramide (Pet-151), 2-(4-Isobutyl-phenyl)-N-[4-methyl-5-(2-nitrooxy-ethyl)-thiazol-2-yl]-propionamide (Pet-152), 4-methyl-5-(2-nitrooxy-ethyl)-thiazole-2-carboxylic acid N'-phthalazin-1-yl-hydrazide (Pet-153), N-[4-Methyl-5-(2-nitrooxy-ethyl)-thiazol-2-yl]-nicotinamide (Pet-154), allyl-[4-methyl-5-(2-nitrooxy-ethyl)-thiazol-2-yl]-amine (Pet-155), N-[4-methyl-5-(2-nitrooxy-ethyl)-thiazol-2-yl]-1-oxy-nicotinamide (Pet-156), 4-acetylamino-N-[4-methyl-5-(2-nitrooxy-ethyl)-thiazol-2-yl]-benzamide (Pet-157), hexadecanoic acid [4-methyl-5-(2-nitrooxy-ethyl)-thiazol-2-yl]-amide (Pet-158), acetic acid 2-[4-methyl-5-(2-nitrooxy-ethyl)-thiazol-2-ylcarbamoyl]-phenyl ester (Pet-159), Pyrrolidine-2-carboxylic acid [4-methyl-5-(2-nitrooxy-ethyl)-thiazol-2-yl]-amide (Pet-160), 2,6-difluoro-N-[4-methyl-5-(2-nitrooxy-ethyl)-thiazol-2-yl]-benzamide (Pet-161), 2-(2,4-dichloro-phenyl)-N-[4-methyl-5-(2-nitrooxy-ethyl)-thiazol-2-yl]-acetamide (Pet-162), 2-(2,4-dichloro-phenoxy)-N-[4-methyl-5-(2-nitrooxy-ethyl)-thiazol-2-yl]-acetamide (Pet-163) and 4-methyl-5-(2-nitrooxy-ethyl)-thiazole-2-carboxylic acid 10,13-dimethyl-3-oxo-2,3,6,7,8,9,10,11,12,13,14,15,16,17-tetradecahydro-1H-cyclopenta[a]phenanthren-17-yl ester (Pet-164) (see, Table 1).

As is demonstrated in the Examples section that follows, the compounds described above were found to be highly active NO-donating agents. In a series of both in vitro and in vivo assays, the NO-donors according to the present invention were found highly efficient in inducing vasorelaxation, while no tolerance phenomenon was observed upon repeated administration thereof.

These results indicate that the NO-donors of the present invention can be beneficially used in the treatment of medical conditions associated with NO.

Hence, further according to the present invention there is provided a method of treating or preventing a medical condition in which modulating an NO level is beneficial. The method, according to this aspect of the present invention, is effected by administering to a subject in need thereof a therapeutically effective amount of one or more of the NO-donating compounds described above.

As used herein, the phrase "therapeutically effective amount" describes an amount of the compound being administered which will relieve to some extent one or more of the symptoms of the disorder being treated, as is further detailed hereinunder.

An exemplary therapeutically effective amount of an NO-donor of the present invention ranges between about 0.01 mg/kg body and about 5 mg/kg body. It should be noted herein that GTN is presently marketed as unit dosage forms of 5 mg, which is equivalent to about 0.07 mg/kg body, assuming an average human body weight of about 70 kg. As is demonstrated in the Example section that follows, the NO-donors of the present invention are at least as effective as GTN in treating hypertension in animals, and in most cases show superior efficacy as compared with GTN. A typical unit dosage from of the NO-donating compounds of the present invention can therefore be equal to or lower than 0.07 mg/kg body.

As used herein the term "about" refers to ±10%.

As is delineated hereinabove, inadequate somatic NO levels are associated with various biological dysfunctions, which typically result from or lead to adverse decrease in the somatic NO levels. Administering an NO-donating compound to subjects that suffer from such inadequate somatic NO levels therefore ameliorate the biological dysfunction itself or its symptoms. Thus, preferably, medical conditions, which are beneficially treatable by the method according to this aspect of the present invention, are those in which elevating the NO-level in a subject is beneficial.

Non-limiting examples of medical conditions in which modulating, and preferably elevating, the NO level is beneficial include cardiovascular diseases or disorders, gastrointestinal diseases or disorders, inflammatory diseases or disorders, respiratory diseases or disorders, central nervous system diseases or disorders, neurodegenerative diseases or disorders, psychiatric diseases or disorders, blood pressure-associated diseases or disorders, coronary artery diseases or disorders, atherosclerosis, cholesterol level-associated diseases or disorders, arterial thrombotic diseases or disorders, a heart failure, a stroke, a septic shock, NSAID-induced gastric diseases or disorders, inflammatory bowel diseases or disorders, ischemic renal diseases or disorders, peptic ulcer, diabetes, pulmonary hypertension, sickle cell anemia, an asthma, chronic obstructive pulmonary disease, dementia, epilepsy, neuroinflammatory diseases or disorders, trauma, multiple sclerosis, erectile dysfunction, other male and female sexual dysfunctions and age-related diseases or disorders.

As is discussed hereinabove, NO-donating compounds according to the present invention, and particularly those that include a NSAID residue, are highly beneficial in treating inflammation. These compounds can thus be efficiently utilized to treat a variety of diseases and disorders associated with inflammation, such as, for example, reperfusion injury of an ischemic organ, e.g., reperfusion injury of the ischemic, myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, diabetes type II, disseminated intravascular coagulation, fatty embolism, Alzheimer's disease, Parkinson's disease, multiple sclerosis, neonate-, infantile- and adult-respiratory diseases, carcinogenesis, hemorrhages in neonates, cerebral vascular disorders and other pathological conditions.

As is further discussed hereinabove, NO-donating compounds according to the present invention, and particularly those that include an anti-diabetic agent residue, are highly beneficial in treating diabetes of all types. These compounds can thus be efficiently utilized to treat for, example, diabetes mellitus, diabetes Type I (juvenile) and non-insulin dependent diabetes Type II.

The NO-donors according to the present invention can be administered orally, rectally, intravenously, intraventricularly, topically, intranasally, intraperitoneally, intestinally, parenterally, intraocularly, intradermally, transdermally, subcutaneously, intramuscularly, transmucosally, by inhalation and/or by intrathecal catheter. Preferably, the NO-donors, according to the present invention, are administered orally or intravenously, and optionally topically, transdermally or by inhalation, depending on the condition and the subject being treated.

The method, according to this aspect of the present invention, can optionally be effected by co-administering to the subject an additional active agent for treating the medical condition. The additional active agent can be co-administered prior to, concomitantly or subsequent to administering the compound of the present invention.

The additional active agent can be, for example, any of the agents known for treating the medical conditions described above such as, but not limited to, cardiovascular agents, NSAIDs, anti-psychotic agents, anti-thrombogenic agents, anti-platelet agents, anti-coagulants, antimicrobial agents, analgesics, metabolite agents, anti-metabolic agents, vasoactive agents, vasodilator agents, chemotherapeutic agents, antioxidants, phospholipids, anti-proliferative agents, anti-diabetics, heparins and the like.

The NO-donors of the present invention, alone or in combination with any other active agents, according to this aspect of the present invention, can be administered either per se, or as a part of a pharmaceutical composition.

Hence, according to still another aspect of the present invention, there are provided pharmaceutical compositions, which comprise one or more of the NO-donors described above and a pharmaceutically acceptable carrier.

As used herein a "pharmaceutical composition" refers to a preparation of one or more of the NO-donors described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the NO-donors into preparations which, can be used pharmaceutically. Proper formulation is dependent upon the route of administration chosen.

For injection, the NO-donors of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the NO-donors of the invention can be formulated readily by combining the NO-donors with pharmaceutically acceptable carriers well known in the art. Such carriers enable the NO-donors of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active NO-donors doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the NO-donors may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the NO-donors for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the NO-donors and a suitable powder base such as, but not limited to, lactose or starch.

The NO-donors described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the NO-donors preparation in water-soluble form. Additionally, suspensions of the NO-donors may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the NO-donors to allow for the preparation of highly concentrated solutions.

Alternatively, the NO-donors may be in powder form for constitution with a suitable vehicle, e.g., sterile, pyrogen-free water, before use.

The NO-donors of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of NO-donors effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any NO-donors used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test NO-donors, which achieves a half-maximal reduction of the mean arterial blood pressure). Such information can be used to more accurately determine useful doses in humans.

As is demonstrated in the Examples section that follows, a therapeutically effective amount for the NO-donors of the present invention may range between about 0.05 mg/kg body and about 5 mg/kg body.

Toxicity and therapeutic efficacy of the NO-donors described herein can be determined by standard pharmaceutical procedures in experimental animals, e.g., by determining the $EC_{50}$, the $IC_{50}$ and the $LD_{50}$ (lethal dose causing death in 50% of the tested animals) for a subject NO-donor. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% vasorelaxation of contracted arteries. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a NO-donors of the invention formulated in a compatible pharmaceutical carrier may also be prepared, placed in an appropriate container, and labeled for treatment of an indicated condition or diagnosis, as is detailed hereinabove.

Thus, according to an embodiment of the present invention, depending on the selected components of the NO-donors, the pharmaceutical compositions of the present invention are packaged in a packaging material and identified in print, in or on the packaging material, for use in the treatment of a condition in which modulating an NO level is beneficial, as described hereinabove.

The NO-donors of the present invention can be further beneficially utilized as active substances in various medical devices.

Hence, according to an additional aspect of the present invention there is provided a medical device which includes one or more of the NO-donating compounds of the present invention, described hereinabove, and a delivery system configured for delivering the NO-donating compound(s) to a bodily site of a subject.

The medical devices according to the present invention are therefore used for delivering to or applying on a desired bodily site the NO-donating compounds of the present invention. The NO-donating compounds can be incorporated in the medical devices either per se or as a part of a pharmaceutical composition, as described hereinabove.

As used herein, the phrase "bodily site" includes any organ, tissue, membrane, cavity, blood vessel, tract, biological surface or muscle, which delivering thereto or applying thereon the compounds of the present invention is beneficial.

Exemplary bodily sites include, but are not limited to, the skin, a dermal layer, the scalp, an eye, an ear, a mouth, a throat, a stomach, a small intestines tissue, a large intestines tissue, a kidney, a pancreas, a liver, the digestive system, the respiratory tract, a bone marrow tissue, a mucosal membrane, a nasal membrane, the blood system, a blood vessel, a muscle, a pulmonary cavity, an artery, a vein, a capillary, a heart, a heart cavity, a male or female reproductive organ and any visceral organ or cavity.

The medical devices according to this aspect of the present invention can be any medical device known in the art, including those defined and classified, for example, by the FDA and specified in http://www.fda.gov/cdrh/devadvice/313.html (e.g., Class I, II and III), depending e.g., on the condition and bodily site being treated.

Thus, for example, in one embodiment of this aspect of the present invention, the medical device comprises a delivery system that is configured to deliver the compound by inhalation. Such inhalation devices are useful for delivering the NO-donating compounds of the present invention to, e.g., the respiratory tract.

The delivery system in such medical devices may be based on any of various suitable types of respiratory delivery systems which are suitable for administering a therapeutically effective dose of the compound of the present invention to a subject. The inhalation device may be configured to deliver to the respiratory tract of the subject, preferably via the oral and/or nasal route, the compound in the form of an aerosol/spray, a vapor and/or a dry powder mist. Numerous respiratory systems and methods of incorporating therapeutic agents therein, such as the NO-donating compounds of the present invention, suitable for assembly of a suitable inhalation device are widely employed by the ordinarily skilled artisan and are extensively described in the literature of the art (see, for example to U.S. Pat. Nos. 6,566,324, 6,571,790, 6,637,430, and 6,652,323; U.S. Food & Drug Administration (USFDA) Center For Drug Evaluation and Research (CDER); http://www.mece.ualberta.ca/arla/tutorial.htm).

The respiratory delivery system may thus be, for example, an atomizer or aerosol generator such as a nebulizer inhaler, a dry powder inhaler (DPI) and a metered dose inhaler (MDI), an evaporator such as an electric warmer and a vaporizer, and a respirator such as a breathing machine, a body respirator (e.g., cuirass), a lung ventilator and a resuscitator.

An exemplary medical device according to this embodiment of the present invention is a metered-dose inhaler (MDI). An MDI typically discharge a measured amount of a therapeutic agent from a pressurized canister (for example, Serevent® Inhalational Aerosol) using a compressed propellant gas. Typically, a human individual self-administers a therapeutic agent via an MDI by applying pressure to a trigger on the MDI so as to deliver a "burst" of a mixture of propellant and medicament into the mouth during an inhalation, the propelling "burst" being provided by the pressure within the canister. Suitable formulations for MDI administration of a therapeutic agent include a solution or suspension of the therapeutic agent in a liquefied propellant (e.g., chlorofluorocarbons and hydrofluoroalkanes). A suitable formulation for MDI administration can include, for example, from about 0.01% to about 5% by weight of the NO-donating compound, from about 0% to about 20% by weight ethanol, and from about 0% to about 5% by weight surfactant, with the remainder being the propellant. For examples of processes of preparing respirable particles, and formulations and devices suitable for inhalation-dosing see, for example, U.S. Pat. Nos. 6,268,533, 5,983,956, 5,874,063, and 6,221,398; and PCT Publication Nos. WO 99/55319 and WO 00/30614. MDIs are advantageous in cases where an easily portable hand-held device is desired. Conventional MDIs can be modified so as to increase the ability to obtain repeatable dosing by utilizing technology which measures the inspiratory volume and flow rate of a subject (refer, for example, to U.S. Pat. Nos. 5,404,871 and 5,542,410). Other types of MDI may deliver the therapeutic agent in a solid state, i.e., as a fine powder of respirable particle size combined with a gaseous propellant.

An example of a typical hand-held MDI is shown in FIG. 34. Metered-dose inhaler 10 is composed of a pressurized cartridge 12 connected to a spray-nozzle 14 via housing 16. Pressurized cartridge 12 contains the liquid formulation 18, which includes a mixture of powdered or liquefied propellant and the NO-donating compound according to the present invention; and a pressurized propellant vapor 20. For administration of the metered dose, the mouth of the subject is sealed around a mouthpiece 22, and pressurized cartridge 12 and housing 16 are squeezed together manually by the subject concomitantly with inhalation by the subject. The squeezing allows pressurized vapors 20 to drive formulation 18 through spray-nozzle 14, thereby forming aerosol 24. The metered dose, contained in aerosol 24, is delivered via the inhaled air-stream to the respiratory tract of the subject via mouthpiece 22.

Another exemplary medical device for delivering an NO-donating compound according to the present invention is a nebulizer inhaler. Nebulizer inhalers produce a stream of high velocity gas, typically from a pressurized external source, which causes a therapeutic agent to spray as a mist which is carried into the respiratory tract of a subject. The therapeutic agent is formulated in a liquid form, such as a solution or a suspension of micronized particles of respirable size, where a suspension of micronized particles is defined as being composed of at least 90% of particles with a diameter of about 10 microns or less. Nebulizer inhalers are most adapted for use in a clinic or hospital setting. Nebulizer inhalers are advantageous for achieving substantially continuous administration of therapeutic agent on a time-scale of minutes, or longer. Typically a nebulizable therapeutic agent solution is packaged in the form of single-dose vials, or in the form of a multi-dose bottle having a calibrated dropper.

Ample guidance for obtaining and utilizing a suitable nebulizer inhaler is provided in the literature of the art [refer, for example to O'Callaghan and Barry, 1997. Thorax 52(Suppl 2):S31-S44 S31].

An example of a nebulizer inhaler which is suitable for use as a medical device according to the present invention (Venturi-type) is shown in FIG. 35. Nebulizer inhaler 26 includes: a nebulization chamber 28, a fluid formulation 30, which comprises an NO-donating compound according to the present invention; a pressurized air delivery conduit 32, including pressurized air, an aerosol 34, an aerosol delivery conduit 36, and an expiration conduit 38. For administration of the NO-donating compound via the nebulizer inhaler, pressurized air is delivered, via air delivery conduit 32, to nebulization chamber 28. Upon exit from nebulization chamber 28, the rapid flow of the exiting pressurized air causes a negative pressure which sucks fluid formulation 30 up nebulization chamber 28 where it encounters exiting pressurized air and becomes aerosol 34. Generated aerosol 34, containing the NO-donating compound, is delivered, via aerosol delivery conduit 36, to a subject, for example via a respiration mask. Upon expiration by the subject, nebulizer inhaler 26 continues to generate aerosol 34, but the expired air and concomitantly generated aerosol 34 are wasted via expiration conduit 38 which allows one-way flow of the wasted gas from nebulization chamber 28.

Another exemplary medical device for delivering an NO-donating compound by inhalation, according to the present invention, is a vaporizer. A vaporizer consists of a hot air supply with temperature controls, a vaporization chamber through which the hot air passes; a cooling chamber and an exhaust or mouthpiece. The compound or composition desired for vaporization, such as the NO-donating compound according to the present invention, is placed in the vaporization chamber, and the hot air brings the substance to the vapor phase by heat, and delivers it to the cooling chamber, typically a water reservoir through which the hot air and the vaporized substances are bubbled through and where the temperature is adjusted for the particular use, such as free release to an open space or direct inhalation mouthpiece.

Another exemplary medical device for delivering an NO-donating compound by inhalation, according to the present invention, is an electric warmer. An electric warmer typically consists of an electric heating element, and an open crucible, or other heat resistant container, in which volatile or volatilizable compositions or compounds are placed. An electric warmer according to this embodiment of the present invention therefore includes a volatile or volatilizable NO-donating compound of the present invention or a composition containing same, which is placed, directly or indirectly in the heat resistant container of the warmer. Another exemplary device for delivering an NO-donating compound by inhalation, according to the present invention, is a warmer, as described above, in which the heating element is non-electric (e.g., a candle).

Exemplary respirators, according to an embodiment of this aspect of the present invention, can be breathing machines, body respirators (e.g., cuirass), lung ventilators and resuscitators. These devices typically include a mask, a tube or a tent, connected to the respirator, through which the active compound (the NO-donating compounds according to the present invention) is delivered. The active compound is introduced into the airflow of the respirator by means of one of the techniques described hereinabove, e.g., by aerosolization via, for example a nebulizer, or by evaporation via, for example, a vaporizer.

According to another embodiment of this aspect of the present invention, the medical device is such that delivering the NO-donating compound is effected by topically applying the medical device on a biological surface of a subject. The biological surface can be, for example, a skin, scalp, an eye, an ear and a nail. Such medical devices can be used in the treatment of various skin conditions and injuries, eye and ear infections and the like.

Exemplary medical devices for topical application include, without limitation, an adhesive strip, a bandage, an adhesive plaster, a wound dressing and a skin patch.

Thus, in an embodiment of this aspect of the present invention, the medical device is a wound dressing, which can be utilized for topical application of the NO-donors of the present invention. Wound dressings containing a therapeutically active agent are typically used for treating cutaneous injuries.

Typically, a wound dressing medical device has a flat structure consisting of an occlusive or semi-occlusive backing layer, non-adherent and absorbent layers, an active agent layer and a securing adhesive tape around the perimeter of the device.

Exemplary commercial wound dressings include hydrocolloids such as, Comfeel®, Granuflex® and Tegasorb®. These dressings absorb water and swell to form a hydrogel. Hydrogels form a moist environment under the dressing and thus promotes wound healing. Hydrogel-based wound dressings typically lose or absorb water depending on the state of hydration of the wound. Exemplary commercial hydrogels include Intrasite Gel®, Nu-Gel® Purilon Gel® and Sterigel®.

Other known wound dressings are based on foam. Exemplary commercial foamable wound dressings include Lyofoam®, Allevyn®, Spyrosorb® and Tielle®.

In another embodiment of this aspect of the present invention, the medical device is an adhesive plaster, which can be utilized for topical application of the NO-donors of the present invention. Adhesive plasters can be used for treating small and superficial cutaneous injuries as a first-aid measure and/or longer treatment of minor injuries.

An adhesive plaster typically has a flat structure consisting of an occlusive or semi-occlusive backing layer and a non-adherent and partially absorbent pad. The pad-side of the backing layer has adhesive margins at both sides of the pad, or all around the pad. The pad is impregnated or otherwise contains a layer of the active agent (herein, an NO-donating compound according to the present invention or a pharmaceutical composition containing same).

Adhesive strips and bandages may also be used as medical devices for topical delivery of one or more of the NO-donating compounds of the present invention.

In still another embodiment of this aspect of the present invention, the medical device is such that delivering the NO-donating compound is effected transdermally. In this embodiment, the medical device is applied on the skin of a subject, so as to transdermally deliver the NO-donating compound to the blood system.

Exemplary medical devices for trandermally delivering an NO-donor according to the present invention include, without limitation, an adhesive plaster and a skin patch. Medical devices for transdermal or transcutaneous delivery of the NO-donating compound typically further include one or more penetration enhancers, for facilitating their penetration through the epidermis and into the system.

A schematic illustration of a typical skin patch, an exemplary medical device according to this aspect of the present invention, which can be utilized for transdermal and/or topical delivery of the NO-donors of the present invention, is presented in FIG. 36. Thus, a skin patch 40 comprises a backing 42, to which a reservoir 44 is attached. Reservoir 44 contains a formulation 46 of the NO-donating compound according to the present invention, optionally as a part of a pharmaceutical composition. The reservoir can be, for example, a pad in which the NO-donating compound is dispersed or soaked, or a liquid reservoir. The device can further include a frontal water or water vapor permeable adhesive 48, which adheres and secures the device to the treated region. Silicone rubbers with self-adhesiveness can alternatively be used. In both cases, a protective permeable layer 50 can be used to protect the adhesive side of the device prior to its use. Skin patch 40 may further comprise a removable cover 52, which serves for protecting the device upon storage.

In another embodiment of this aspect of the present invention, the medical device is such that delivering the NO-donating compound is effected by implanting the medical device in a bodily organ. As used herein, the term "organ" further encompasses a bodily cavity.

The organ can be, for example, a pulmonary cavity, a heart or heart cavity, a bodily cavity, an organ cavity, a blood vessel, an artery, a vein, a muscle, a bone, a kidney, a capillary, the space between dermal layers, an organ of the female or male reproductive system, an organ of the digestive tract and any other visceral organ.

The medical device according to this embodiment of the present invention, typically includes a device structure in which an NO-donor according to the present invention is incorporated. The NO-donating agents can thus be, for example, applied on, entrapped in or attached to (chemically, electrostatically or otherwise) the device structure.

The device structure can be, for example, metallic structure and thus may be comprised of a biocompatible metal or mixture of metals (e.g., gold, platinum).

Alternatively, the device structure may be comprised of other biocompatible matrices. These can include, for example, plastics, silicon, polymers, resins, and may include at least one component such as, for example, polyurethane, cellulose ester, polyethylene glycol, polyvinyl acetate, dextran, gelatin, collagen, elastin, laminin, fibronectin, vitronectin, heparin, segmented polyurethane-urea/heparin, poly-L-lactic acid, fibrin, cellulose and amorphous or structured carbon such as in fullerenes, and any combination thereof.

In cases where a biodegradable implantable device is desired, the device structure can be comprised of a biocompatible matrix that is biodegradable. Biodegradable matrices can include, for example, biodegradable polymers such as poly-L-lactic acid.

Optionally, the device structure may be comprised of biocompatible metal(s) coated with other biocompatible matrix.

Further optionally, in cases where a device which releases the NO-donating compounds of the present invention in a controlled manner is desired, the device structure can be comprised of or coated with a biocompatible matrix that function as or comprises a slow release carrier. The biocompatible matrix can therefore be a slow release carrier which is dissolved, melted or liquefied upon implantation in the desired site or organ. Alternatively, the biocompatible matrix can be a pre-determined porous material which entraps the NO-donating compounds in the pores. When implanted in a desired site, the NO-donating compounds diffuse out of the pores, whereby the diffusion rate is determined by the pores size and chemical nature. Further alternatively, the biocompatible matrix can comprise a biodegradable matrix, which upon degradation releases the NO-donating compounds of the present invention.

The NO-donating compounds of the present invention can be incorporated in the device structure by any methodology known in the art, depending on the selected nature of the device structure. For example, the NO-donating compounds can be entrapped within a porous matrix, swelled or soaked within a matrix, or being adhered to a matrix.

Exemplary medical devices for delivering the NO-donating compounds of the resent invention by implanting include, without limitation, an aortic aneurysm graft device, an atrioventricular shunt, a catheter, a defibrilator, a heart valve, a hemodialysis catheter, a hemodialysis graft, an indwelling arterial catheter, an indwelling venous catheter, a needle, a pacemaker, a pacemaker lead, a patent foramen ovale septal closure device, a stent, a stent graft, a suture, a synthetic vascular graft, a thread, a tube, a vascular anastomosis clip, a vascular aneurysm occluder, a vascular clip, a vascular prosthetic filter, a vascular sheath and a drug delivery port, a venous valve and a wire.

A preferred medical device according to this embodiment of the present invention is a stent. Stents, after insertion into blood vessels, oftentimes cause restenosis (the re-narrowing of a blood vessel). One of the most common complications after stent insertion is platelet adhesion and aggregation resulting in thrombus formation and lumen occlusion. Since NO is an antiplatelet agent and an anti-smooth muscle cell proliferation agent, it can consequently be used to reduce the risk of thrombus formation associated with the use of stents, incorporating NO-donors in stents is highly advantageous in this respect, especially if the bioactive residue conjugated to the NO-donor, according to the present invention, is an anti-inflammatory agent.

A schematic illustration of an exemplary implantable device according to this embodiment of the present invention is presented in FIG. 37. FIG. 37 presents stent 52, which is comprised of an expandable supporting element 54 and further incorporates an active substance 56. The active substance can be either the NO-donating compounds according to the present invention per se, or, preferably, can be a biocompatible matrix, as described hereinabove, which comprises the NO-donating compounds of the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Chemical Syntheses

Materials and Methods:
Proton NMR spectra were recorded using Varian 300 MHz and Brucker 200 MHz spectrometer. Spectra were obtained in deutro-chloroform ($CDCl_3$), unless indicated otherwise. Chemical shifts ($\delta$) are reported in parts per million (ppm) downfield from tetramethylsilane.

Gas chromatography was carried out on a Hewelett-Packard (HP-6890) gas chromatograph having a 5% phenylsiloxan column and a FID detector.

Ultraviolet (UV) spectra were run as solutions in ethanol on a Beckman MV1 spectrophotometer.

4-Methyl-5-thiazoleethanol and propionamide were purchased from Aldrich chemical Company, USA.

Phosphorus pentasulfide was purchased from Merck, Darmstadt, Germany.

Tetrahydrofuran (THF) was dried and was freshly distilled over sodium/benzophenone ketyl prior to use.

Other reagents were purchased from different suppliers and were used without purification, unless otherwise indicated.

5-Acetoxy-3-chloro-2-pentanone (ACP) was prepared according to the synthetic pathway described in Scheme 1 below and the corresponding procedure published by Buchman [*J. Am. Chem. Soc.* 58, 1803, 1936].

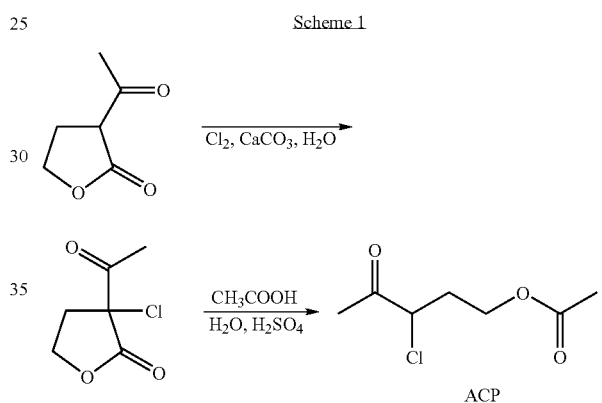

Syntheses of 2-substituted-4-methyl-5-(2-nitrooxy-ethyl)-thiazole derivatives —General Procedure The general synthetic pathway for preparing 2-substituted-4-methyl-5-(2-nitrooxy-ethyl)-thiazole derivatives, which serve as thiazole-based NO-donor compounds according to a preferred embodiment of the present invention, is presented in Schemes 2-4 below. In general, a desired thioamide is first prepared from a corresponding amide (Scheme 2), and is thereafter reacted, via a condensation reaction, with an alpha-chloroketone such as ACP, so as to form a 4-substituted-5-thiazoleethanol derivative (a 4-methyl-5-thiazoleethanol derivative in case of ACP) (Scheme 3). The alcohol moiety of the latter is then reacted with nitric acid, so as to produce the desired NO-donor according to this preferred embodiment of the present invention (Scheme 4).

Thus, according to a representative synthetic pathway, a desired thioamide (general Compound II) is typically prepared according to the present invention by placing a corresponding amide (general Compound I) in a dry solvent such as THF or toluene, slowly adding thereto phosphorus pentasulfide ($P_2S_5$), while stirring, for a time period of 20-30 minutes under controlled temperature, and heating the resulting mixture at reflux temperature for additional 2-3 hours.

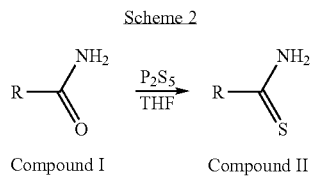

Scheme 2

Compound I → Compound II

The respective 4-methyl-5-thiazoleethanol (general Compound III) is prepared from the thioamide (Compound II) according to the Hantzsch procedure [Hantzsch and Trauman, 1888, Ber 21, 938], as is shown in Scheme 3 below, by adding to the thioamide reaction mixture 5-acetoxy-3-chloro-2-pentanone (ACP), over a time period of 15-20 minutes. The reaction mixture is then heated at reflux temperature for about 20 hours, and the solvent is thereafter removed by distillation at atmospheric pressure. The reaction mixture is then cooled to 25° C., hydrochloric acid (10%) is added, and the mixture is heated at reflux temperature for one additional hour. Extraction of the reaction mixture with dichloromethane, drying over sodium sulfate, and evaporation to dryness, results in the desired 4-methyl-5-thiazoleethanol derivative.

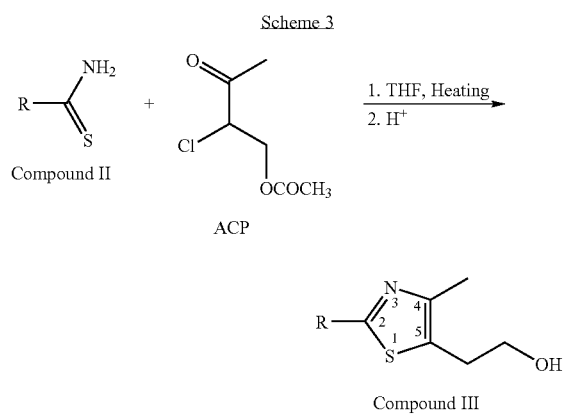

Scheme 3

Compound II + ACP → Compound III

Nitration of the 4-methyl-5-thiazoleethanol derivative (Compound III) is then carried out as is illustrated in Scheme 4 below, by drop wise addition of nitric acid (85-90%) to sulfuric acid (95-98%) over a time period of 20 minutes while keeping the temperature at 0-5° C., followed by addition of the 4-methyl-5-thiazoleethanol derivative. After stirring the reaction mixture for additional 2-3 hours at 0-5° C., it is poured carefully onto cold water, washed with sodium hydroxide 20%, and extracted with dichloromethane. The extracts are combined, dried and evaporated to dryness, to thereby produce the respective 2-substituted-4-methyl-5-(2-nitrooxy-ethyl)-thiazole (general Compound IV, also denoted as Pet, whereby each specific derivative is identified by a numeral).

Scheme 4

Compound III → Compound IV

Using the general procedure described above, a variety of NO-donor compounds according to a preferred embodiment of the present invention were prepared, as is detailed hereinbelow.

Preparation of 2-Ethyl-4-methyl-5-(2-nitrooxy-ethyl)-thiazole (Pet-2): Synthesis of 2-(2-ethyl-4-methyl-thiazol-5-yl)-ethanol

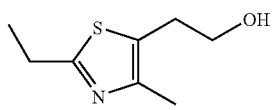

Propionamide (20 grams, 0.27 moles) and dried THF (150 grams) were added to a 500 ml three-neck flask equipped with a mechanical stirrer, a condenser and a thermometer. The mixture was stirred and 18 grams of phosphorus pentasulfide (0.08 moles) were added over a time period of 30 minutes while keeping the temperature between 20-25° C. The reaction mixture was then refluxed for 2 hours and was thereafter cooled to room temperature. 57.8 grams of 5-acetoxy-3-chloro-2-pentanone were then added, over a time period of 15 minutes, and the reaction mixture was allowed to reflux for 20 hours. Thereafter, the THF was removed by distillation at atmospheric pressure, the reaction mixture was cooled to 25° C., 120 grams of hydrochloric acid (10%) were added, and the mixture was brought back to reflux for 1 additional hour. After cooling to room temperature the reaction mixture was extracted with two portions of 50 grams of dichloromethane to remove excess starting materials. The acidic aqueous phase was turned basic with a 20% aqueous solution of sodium hydroxide and the resulting thiazole was extracted with three portions of 75 grams of dichloromethane. The dichloromethane extracts were combined and dried over sodium sulfate, filtered and evaporated to dryness. The residue was distilled under vacuum at 0.5 mmHg to yield 20 grams of pale yellow oil (43.3% yield) having a purity of 98.9%, as determined by gas chromatography.

$^1$H-NMR (CDCl$_3$): δ=3.75 (t, 2H, CH$_2$OH, J=6.6 Hz), 2.84 (t and q overlapping, 5H, J=6.6 Hz and 7.5 Hz respectively), 2.26 (S, 3H, CH$_3$, benzylic), 1.29 (t, 3H, J=7.5 Hz) ppm; UV(ethanol): λmax=252 nm (ϵ=56004). MS: m/e (relative intensity)=171[M$^+$(27)], 140(100), 99(5), 85(12), 45(20).

Synthesis of
2-Ethyl-4-methyl-5-(2-nitrooxy-ethyl)-thiazole

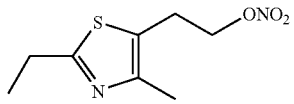

Fifteen (15) ml of nitric acid of (85-90%) were added dropwise to 15 ml of sulfuric acid (95-98%) over a time period of 20 minutes while keeping the temperature at 0-5° C. After 2 hours, 14.3 grams (83.60 mmole) of 2-ethyl-4-methyl-5-thiazoleethanol, prepared as described above, were added, while the temperature was still maintained at 0-5° C., the reaction mixture was stirred for 2 hours at the same temperature, and was then poured carefully onto 125 ml of cold water. The water solution was made basic with a 20% aqueous solution of sodium hydroxide and the aqueous phase was extracted with three portions of 75 grams of dichloromethane. The extracts were combined and dried over sodium sulfate, filtered and evaporated to dryness. Chromatography of the crude product on silica gel (using a mixture of 75:25 ethyl acetate:hexane as an eluent) yielded 10.5 grams (58% yield) of colorless liquid having a purity of 98%, as determined by gas chromatography.

$^1$H-NMR (CDCl$_3$): δ=1.23 (t, 3H, J=11.4 Hz), 2.22 (s, 3H, benzylic), 2.79 (q, 2H, CH$_2$ benzylic, J=11.4 Hz), 3.05 (t, 2H, CH$_2$ benzylic, J=10.2 Hz), 4.46 (t, 2H, CH$_2$ONO$_2$, J=10.2 Hz) ppm. UV(ethanol): λmax=250 nm (ε=53070). MS: m/e (relative intensity)=189(30), 140(100), 99(9), 85(10).

Preparation of 2,4-Dimethyl-5-(2-nitrooxy-ethyl)-thiazole (Pet-3)

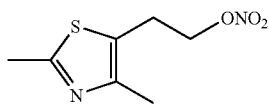

The respective ethanol derivative of Pet-3, 2-(2,4-Dimethyl-thiazol-2-yl)-ethanol, was prepared according to the general procedure described above for general Compound III and the procedure described above for Pet-2, by reacting 10 grams (0.27 moles) of acetamide, 150 grams dried toluene and 18 grams (0.08 moles) phosphorus pentasulfide, and thereafter adding 48.20 grams of 5-acetoxy-3-chloro-2-pentanone to the reaction mixture and refluxing the resulting mixture for 20 hours, after which the toluene was removed by distillation at atmospheric pressure. The residue was then cooled to 25° C. and 120 grams of hydrochloric acid (10%) were added. The reaction mixture was allowed to reflux for 1 additional hour and, after cooling, was extracted with two portions of 50 grams of dichloromethane to remove excess starting materials. The acidic water phase was turned basic with 20% sodium hydroxide and the obtained thiazole was extracted with three portions of 75 grams of dichloromethane. The dichloromethane extracts were combined and dried over sodium sulfate, filtered and evaporated to dryness. The residue was distilled under vacuum at 2 mmHg to provide 20 grams (43.3% yield) of colorless oil having a purity of 98.9% as determined by gas chromatography.

Nitration of 2-(2,4-Dimethyl-thiazol-2-yl)-ethanol, was carried out as described above, to give 9.5 grams (48% yield) of 2,4-dimethyl-5-(2-nitrooxy-ethyl)-thiazole (Pet-3) as pale yellow liquid having a purity of 99.5% as determined by gas chromatography.

$^1$H-NMR (CDCl$_3$): δ=2.45 (s, 3H, CH$_3$), 2.72 (s, 3H, CH$_3$), 2.79 (q, 2H, CH$_2$ benzylic, J=11.3 Hz), 3.05 (t, 2H, CH$_2$, J=10.1 Hz), 4.46 (t, 2H, CH$_2$ONO$_2$, J=10.2 Hz) ppm.

Preparation of 2-Isopropyl-4-methyl-5-(2-nitrooxy-ethyl)-thiazole (Pet-4)

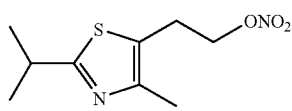

Based on the general procedure presented hereinabove, dry toluene (200 ml) was placed in a 500 ml round-bottomed flask fitted with a reflux condenser. A mixture of 30 grams (0.34 moles) finely grinded isobutyramide (prepared according to Kent R. E. and McElvain S. M., *Organic Syntheses, CV* 3, 490) and 15.2 grams (0.07 moles) of powdered phosphorus pentasulfide was prepared and immediately transferred to the flask. In a separate vial a solution of 27 ml (0.34 moles) of 5-acetoxy-3-chloro-2-pentanone (ACP) and 50 ml of dry toluene was prepared, and 5 ml of this solution were added to the reaction mixture. The exothermic reaction was initiated by gradual heating in an oil bath, the oil bath was then removed and the remainder of the ACP-toluene solution was added gradually through the reflux condenser. Upon completing the addition of ACP and once the reaction appeared to be ceased, the mixture was heated at 75° C. for 24 hours. The reaction mixture was thereafter cooled to 25° C., 120 grams of hydrochloric acid (10%) were added and the mixture was refluxed for an additional one hour. After cooling to room temperature, the reaction mixture was extracted with two portions of 50 grams of dichloromethane to remove excess starting materials. 250 ml of water were added to the toluene phase while shaking for 30 minutes, the bi-phasic mixture was poured into a separation funnel, and the reddish organic layer was discarded. The aqueous layer was turned basic with 5 N sodium hydroxide or potassium hydroxide, the crude thiazole, which separates as a black organic layer, was extracted with ether, and the aqueous lower layer was washed with five 120 ml portions of ethyl acetate. The combined ethyl acetate extracts were dried over anhydrous sodium sulfate and filtered through glass wool. The ethyl acetate was removed by steam bath distillation, to give 21 grams (21% yield based on isobutyramide) of residual oil having a purity of 98% as determined by gas chromatography.

$^1$H-NMR (CDCl$_3$): δ=2.45 (s, 3H,), 2.22 (s, 3H, benzylic), 2.79 (q, 2H, CH$_2$ benzylic, J=11.4 Hz), 3.05 (t, 2H, CH$_2$ benzylic, J=10.2 Hz), 4.46 (t, 2H, CH$_2$ONO$_2$, J=10.2 Hz) ppm. UV(ethanol): λmax=250 nm (ε=53070). MS: m/e (relative intensity)=189(30), 140(100), 99(9), 85(10).

Nitration of 2-(2-isopropyl-4-methyl-thiazol-2-yl)-ethanol, was carried out as described above, to give 1.5 grams (50% yield) of 2-isopropyl-4-methyl-5-(2-nitrooxy-ethyl)-thiazole (Pet-4) having a purity of 98% as determined by gas chromatography.

Preparation of 4-Methyl-5-(-2-nitrooxy-ethyl)-2-(1-nitrooxy-ethyl-thiazole (Pet-5)

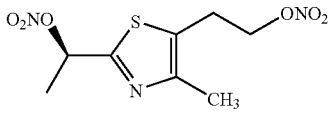

Pet-5 was prepared according to the general procedure presented hereinabove and the procedure described above for the preparation of Pet-2, using L-(−)-lactamide as the starting material and dry THF as a solvent, to give the product as brown oil (56% yield) having a purity of 98% as determined by thin-layer chromatography.

$^1$H-NMR (CDCl$_3$): δ=1.51 (s, 3H, CH$_3$), 2.49 (s, 3H, CH$_3$, Aromatic), 2.79 (t, 2H, CH$_2$ benzylic), 3.85 (t, 2H, CH$_2$), 4.69 (q, 1H, CHONO$_2$) ppm.

Preparation of 4-Methyl-5-(nitrooxy-ethyl)-2-trifluoromethyl-thiazole (Pet-6)

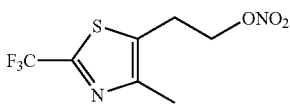

Pet-6 was prepared according to general procedure presented hereinabove and the procedure described above for the preparation of Pet-2, using trifluoroacetamide as the starting material and dry toluene as a solvent, to give the product as pale yellow oil (35% yield) having a purity of 96% as determined by thin-layer chromatography.

$^1$H-NMR (CDCl$_3$): δ=2.45 (s, 3H, CH$_3$), 2.74 (q, 2H, CH$_2$, J=11.2 Hz), 3.10 (t, 2H, CH$_2$, J=10.2 Hz), 3.89 (t, 2H, CH$_2$ONO$_2$, J=10.3 Hz) ppm.

Preparation of dimethyl-[4-methyl-5-(2-nitrooxy-ethyl)-thiazol-2-yl]-amine (Pet-7)

The synthesis of Pet-7 is illustrated in Scheme 5 below.

Scheme 5

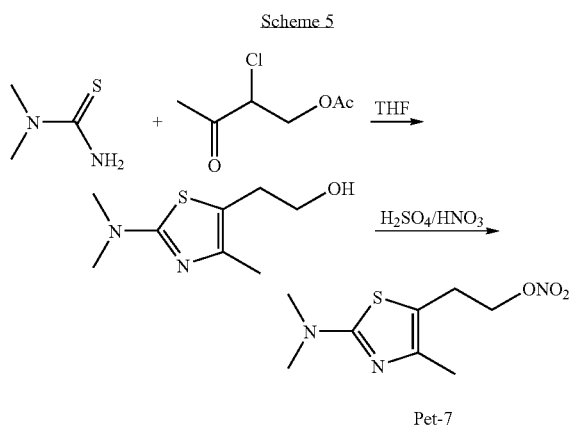

Pet-7

According to the general procedure presented hereinabove, 200 ml of dry toluene and 10 grams (0.095 moles) of N,N-dimethylthiourea (obtained from Merck, Germany) were placed in a 500 ml round-bottomed flask fitted with a reflux condenser. 17.5 grams (0.1 moles) of 5-acetoxy-3-chloro-2-pentanone (ACP) were added to the solution over a time period of 20 minutes. The reaction mixture was refluxed at 80° C. for 24 hours, after which the toluene was removed by evaporation. 100 ml of water and 15 ml of HCl solution (32%) were added and the resulting mixture was refluxed for 1 hour at 90° C. After cooling, the mixture was washed with two portions of 100 ml of dichloromethane to remove excess of starting materials. The aqueous phase was turned basic (pH 8-9) using 5 N solution of sodium hydroxide. The 2-(2-dimethylamino-4-methyl-thiazol-5-yl)-ethanol was extracted with three portions of 100 ml of dichloromethane and the combined extracts were dried over sodium sulfate. The dichloromethane was removed under vacuum to yield 8 grams (45%) of white crystalline powder, which was used in the subsequent nitration step without further purification.

Figure 1:
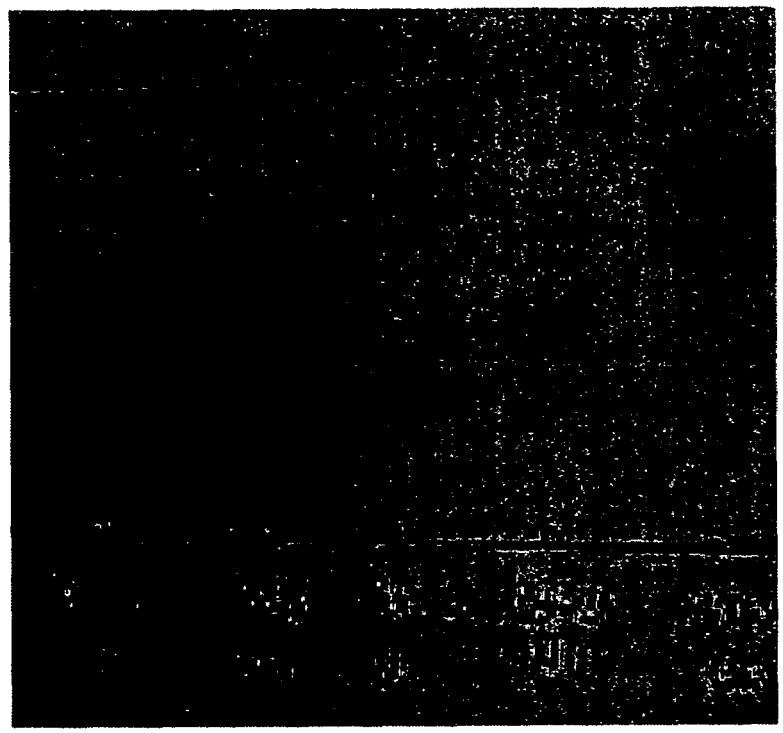
FIG. 1 presents a thin-layer chromatogram showing the retention times (obtained using ethyl acetate as eluent) and the presence of a nitrate ester moiety (demonstrated by staining with diphenylamine) of glyceryltrinitrate and exemplary NO-donor compounds according to the present invention, Pet-7 Pet-8, Pet-12, Pet-13.
Figure 2:
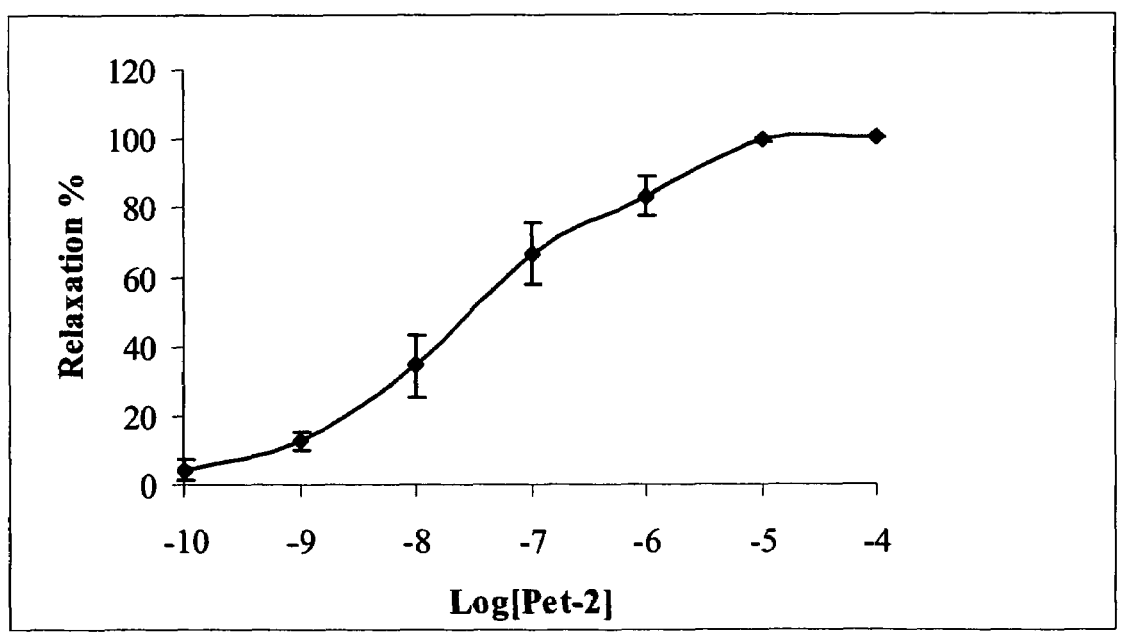
FIG. 2 presents a plot demonstrating the vasorelaxation effect induced by Pet-2, an exemplary NO-donor according to the present invention, in isolated rat aorta pre-treated in vitro with 1 μM epinephrine (error bars represent the mean±standard errors, n=5-8)
Figure 3:
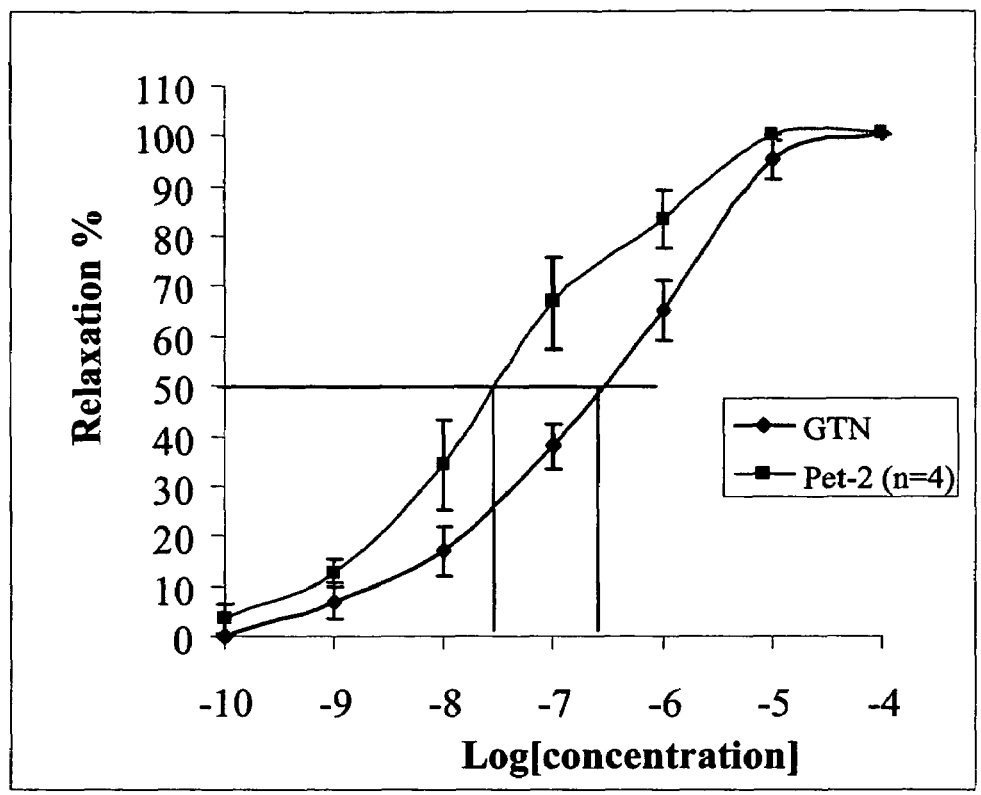
FIG. 3 presents comparative plots demonstrating the superior vasorelaxation effect induced by Pet-2, an exemplary NO-donor according to the present invention (squares), as compared with glyceryltrinitrate (diamonds) in isolated rat aorta pre-treated in vitro with 1 μM epinephrine (error bars represent the mean±standard errors, n=4)
Figure 4:
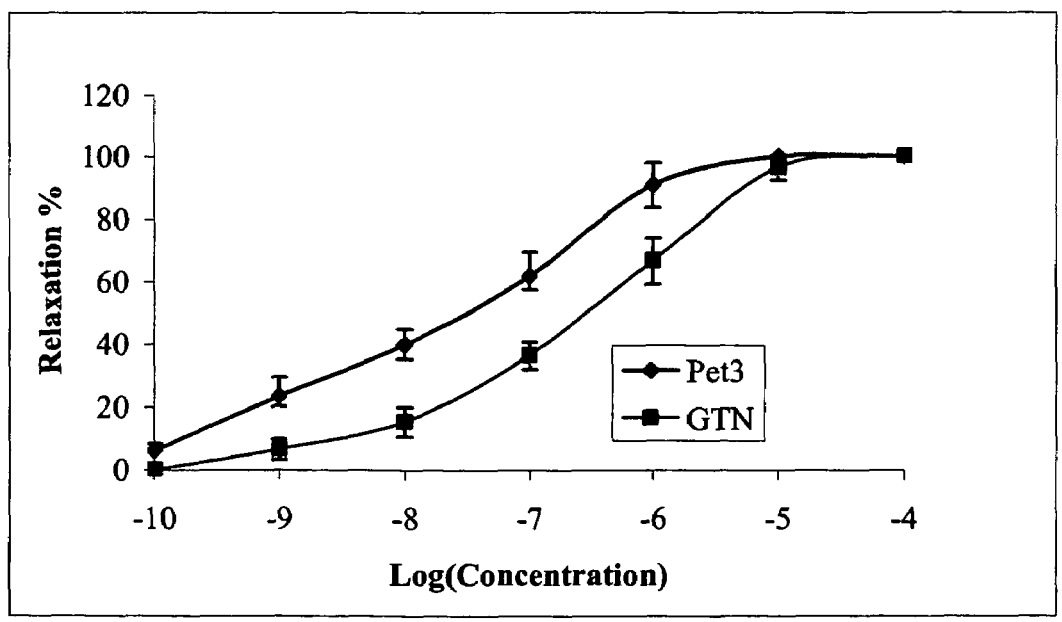
FIG. 4 presents comparative plots demonstrating the superior vasorelaxation effect induced by of Pet-3 (n=8, diamonds), an exemplary NO-donor according to the present invention, as compared with glyceryltrinitrate (n=4, squares)

Nitration of 2-(2-dimethylamino-4-methyl-thiazol-5-yl)-ethanol was carried out by cooling 1.58 grams (0.016 moles) of sulfuric acid (95-98%) to 0-5° C. and addition thereto of 1.016 grams (0.016 moles) nitric acid (70%) drop-wise over a time period of 20 minutes while keeping the temperature between 0-5° C. Following, 3 grams of 2-(2-dimethylamino-4-methyl-thiazol-5-yl)-ethanol (16.10 mmoles) were added over a time period of 30 minutes at 0-5° C. After the addition was completed, the reaction mixture was stirred for 30 minutes at 0-5° C. The reaction mixture was then added carefully to 25 ml of cold water. The water solution was turned basic with a 20 5 aqueous solution of sodium hydroxide and the aqueous phase was extracted with three 75 grams portions of a mixture of 1:1 ethyl acetate:ether. The organic extracts were combined, dried over sodium sulfate, filtered and evaporated to dryness. The nitration step was confirmed initially by thin-layer chromatography stained with diphenylamine as a marker for the nitrate ester moiety (FIG. 1). Chromatography of the crude product on silica gel (using a mixture of 2:1 ethyl acetate:hexane as eluent) gave 2 grams (54% yield) of the product as white crystalline needles having a purity of 99% as determined by gas chromatography.

$^1$H-NMR (CDCl$_3$): δ=2.45 (s, 6H, N—CH$_3$), 2.54 (s, 3H, CH$_3$), 2.75 (q, 2H, CH$_2$), 3.12 (t, 2H, CH$_2$), 4.01 (t, 2H, CH$_2$ONO$_2$) ppm.

Preparation of 4-methyl-5-(2-nitrooxy-ethyl)-2-phenyl-thiazole (Pet-8)

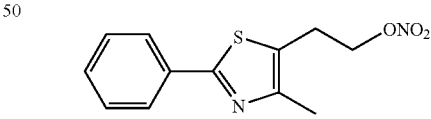

2-(4-Methyl-2-phenyl-thiazol-5-yl)-ethanol was prepared, according to general procedures presented hereinabove, by adding 7.3 grams (0.053 moles) of thiobenzamide (obtained from Merck, Germany) to 200 ml dry THF, followed by addition of 9.5 grams (0.053 moles) 5-acetoxy-3-chloro-2-pentanone over a time period of 20 minutes. The reaction mixture was then refluxed at 80° C. for 24 hours, after which the THF was removed by evaporation. 100 ml of water and 15 ml of HCl solution (32%) were added and the reaction mixture was refluxed for 1 hour at 90° C. After cooling, the mixture was washed with two portions of 100 ml of dichloromethane to remove excess starting materials.

The aqueous phase was turned basic (pH 8-9) using an aqueous solution of 5 N sodium hydroxide. The 2-(4-methyl-2-phenyl-thiazol-5-yl)-ethanol was extracted with three portions of 100 ml of dichloromethane and the combined extracts were dried over sodium sulfate. After removal of the dichloromethane 8 grams (45% yield) of the 2-(4-methyl-2-phenyl-thiazol-5-yl)-ethanol product were obtained as a reddish-brown liquid.

The nitration of 2-(4-methyl-2-phenyl-thiazol-5-yl)-ethanol was carried out subsequently according to the procedure described hereinabove, to give 4-methyl-5-(2-nitrooxy-ethyl)-2-phenyl-thiazole) in 40% yield. The product was purified by column chromatography using a mixture of 1:1:1 ethyl acetate:hexane:dichloromethane as eluent, to purity of 99.5% as determined by HPLC and by thin-layer chromatography stained with diphenylamine as a marker for the nitrate ester moiety (FIG. 1).

NMR (CDCl$_3$): δ=2.37 (s, 3H, CH$_3$), 3.18 (t, 3H, CH$_2$), 4.57 (t, 2H, CH$_2$ONO$_2$), 7.32-8.19 (m, 5H, Aromatic) ppm.

Preparation of 2-methoxy-4-methyl-5-(2-nitrooxy-ethyl)-thiazole (Pet-9)

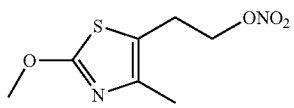

Pet-9 was prepared according to general procedure presented hereinabove and the procedure described above for the preparation of Pet-2, using the respective amide as the starting material and dry THF as a solvent, to give the product as brown oil (51% yield) having a purity of 97% as determined by thin-layer chromatography.

The product was further purified by column chromatography using a mixture of 1:1 ethyl acetate:hexane as eluent, to purity of 99.5% as determined by gas chromatography.

$^1$H-NMR (CDCl$_3$): δ=2.45 (s, 3H, CH$_3$, benzylic), 3.72 (s, 3H, OCH$_3$), 4.46 (t, 2H, CH$_2$ONO$_2$, J=10.2 Hz) ppm.

Preparation of 4-methyl-5-(2-nitrooxy-ethyl)-thiazole-2-ylamine (Pet-10)

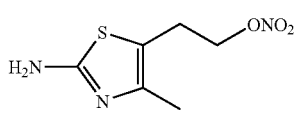

2-(2-Amino-4-methyl-thiazol-5-yl)-ethanol was prepared according to general procedures presented hereinabove, by adding 20 grams (0.263 moles) of thiourea to 200 ml of dry toluene, followed by addition of 47 grams (0.263 moles) of 5-acetoxy-3-chloro-2-pentanone over a time period of 20 minutes. The reaction mixture was heated at 80° C. for 24 hours and thereafter approximately 180 ml of toluene were removed by evaporation. 180 ml of water and 20 ml of HCL solution (32%) were then added and the reaction mixture was refluxed for 1 hour at 90° C. The organic phase was then removed by washing with chloroform, and the aqueous phase was turned basic (pH 8-9) using a 5 N solution of sodium hydroxide. The product was extracted once with 70 ml chloroform and once with 70 ml ethyl acetate. The combined organic extracts were dried over sodium sulfate and the solvents were removed by evaporation to give 30 grams (72% yield) of violet-brown crystals.

Subsequently, 4-methyl-5-(2-nitrooxy-ethyl)-thiazole-2-ylamine was prepared by drop-wise addition of 1.59 grams of nitric acid (70%) to 2.48 grams of cooled sulfuric acid (95-98%) at 0-5° C. over a time period of 20 minutes. Following, 4 grams (0.025 moles) of 2-(2-Amino-4-methyl-thiazol-5-yl)-ethanol were added over a time period of 45 minutes at 0-5° C. After the addition was completed, the reaction mixture was stirred for 3 hours at 25° C., and was then added carefully to 50 ml of cold water. The water solution was turned basic with an aqueous solution of 20% sodium hydroxide and the aqueous phase was extracted with three portions of 75 grams of ethyl acetate. The organic extracts were combined, dried over sodium sulfate, filtered and evaporated to dryness under vacuum. Chromatography of the crude product on silica gel (using a mixture of 8:2 ethyl acetate:hexane as eluent) gave 1.8 grams (35% yield) of the product as orange oil having a purity of 98.5% as determined by gas chromatography.

$^1$H-NMR (CDCl$_3$): δ=2.10 (s, 3H, CH$_3$), 2.79 (t, 2H, CH$_2$), 3.37 (t, 2H, CH$_2$OH,), 4.87 (s, breit, NH$_2$) ppm.

Preparation of 4-[4-methyl-5-(2-nitrooxy-ethyl)thiazole-2-yl]-piperidine (Pet-11)

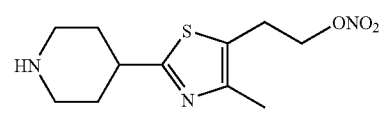

Pet-11 was prepared according to general procedure presented hereinabove and the procedure described above for the preparation of Pet-2, using the respective amide as the starting material and dry THF as a solvent, to give the product as red oil (56% yield) having a purity of 95% as determined by thin-layer chromatography.

$^1$H-NMR (CDCl$_3$): δ=1.77 (t, 2H, CH$_2$,-piperidine), 2.45 (t, CH$_3$-benzylic), 2.77 (t, 2H, CH$_2$,-piperidine), 2.73 (t, 2H, CH$_2$-benzylic) 2.78 (t, H, CH,-piperidine), 4.45 (t, 2H, CH$_2$—ONO$_2$) ppm.

Preparation of 3-[4-methyl-5-(2-nitrooxy-ethyl)-thiazole-2-yl]-pyridine (Pet-12)

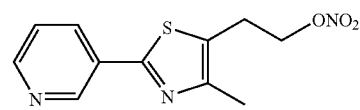

2-(4-Methyl-2-pyridin-3-yl-thiazole-5-yl)-ethanol was prepared according to the general procedure presented hereinabove, by adding 20 grams (0.145 moles) of thionicotinamide (purchased from Acros, Belgium) to 200 ml of dry toluene, followed by addition of 26 grams (0.145 moles) of ACP over a time period of 20 minutes. The reaction mixture heated for 24 hours at 80° C. and thereafter about 180 ml of toluene were removed by evaporation. 100 ml of water and 20 ml of HCl solution (32%) were added and reflux was continued for 1 hour at 90° C. The organic phase was then removed by washing with chloroform and the aqueous phase was turned basic (pH 8-9) using a 5 N solution of NaOH. The 2-(4-methyl-2-pyridin-3-yl-thiazol-5-yl)-ethanol was extracted with three portions of 100 ml of chloroform and the combined extracts were dried over sodium sulfate. The chloroform was thereafter removed and the residue was purified by liquid chromatography, using a mixture of 9:1 ethyl acetate:methanol as eluent, to give 10 grams (31% yield) of the 2-(4-methyl-2-pyridin-3-yl-thiazol-5-yl)-ethanol product as a violet-brown powder.

3-[4-Methyl-5-(2-nitrooxy-ethyl)-thiazol-2-yl]-pyridine was prepared by drop-wise addition of 1.145 gr. of nitric acid (70%) to 1.78 grams of cooled sulfuric acid (95-98%) at 0-5° C., followed by addition of 4 grams (0.0181 moles) 2-(4-methyl-2-pyridin-3-yl-thiazol-5-yl)-ethanol over a time period of 30 minutes at 0-5° C. After the addition was completed the reaction mixture was stirred for 30 minutes at 0-5° C., and for one additional hour at room temperature. The reaction mixture was then added carefully to 25 ml of cold water. The water solution was turned basic with an aqueous 20% solution of sodium hydroxide and the aqueous phase was extracted with three portions of 75 grams of dichloromethane. The extracts were combined, dried over sodium sulfate, filtered and evaporated to dryness under vacuum. The nitration step was confirmed initially by thin-layer chromatography stained with diphenylamine as a marker for the nitrate ester moiety (FIG. 1). Chromatography of the crude product on silica gel (using ethyl acetate as eluent) gave 1.5 grams (41% yield) of Pet-12 as a pale yellow liquid having a purity of 99% as determined by HPLC.

$^1$H-NMR (CDCl$_3$): δ=2.47 (s, 3H, CH$_3$), 2.77 (t, 2H, CH$_2$, benzylic), 3.88 (t, 2H, CH$_2$ONO$_2$), 7.44-8.56 (m, 4H, Aromatic) ppm.

Preparation of 1,4-Bis-[4-Methyl-5-(2-nitrooxy)-ethyl)-thiazol-2-yl]-Butane (Pet-13)

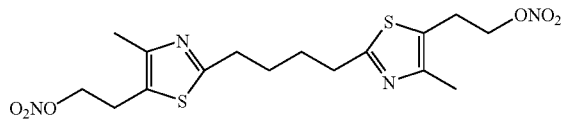

Pet-13 was prepared according to general procedure presented hereinabove and the procedure described above for the preparation of Pet-2, using the respective hexane diamide as the starting material and dry THF as a solvent, to give the product as red oil (52% yield) having a purity of 98% as determined by thin-layer chromatography stained with diphenylamine as a marker for the nitrate ester moiety (FIG. 1).

Preparation of 2-[1-(6-methoxy-naphthalen-2-yl-ethyl]-4-methyl-5-(2-nitrooxy-ethyl)-thiazole (Pet-17)

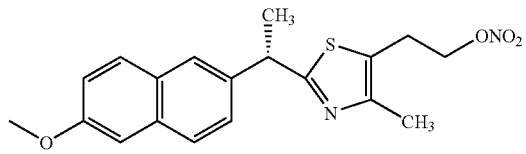

The starting material naproxenamide was prepared as described in Scheme 6 below.

Scheme 6

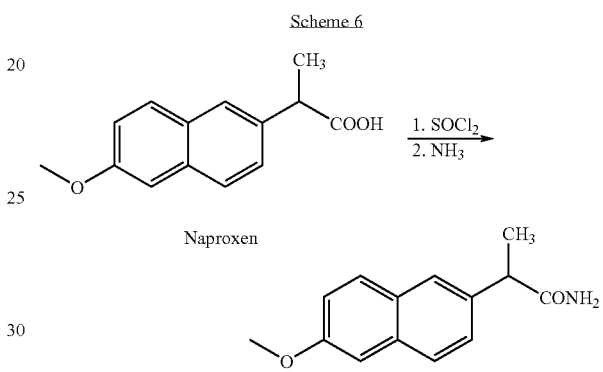

Naproxyl chloride was first prepared in a 500 ml three-necked flask equipped with a 250 ml dropping funnel, an efficient mechanical stirrer, and a condenser with a gas-absorption trap attached to the top of the condenser. The water supplied to the condenser was cooled to 0° C., and the flask was cooled in a large water bath. 15.5 grams (0.13 moles) of thionyl chloride were placed in the flask, and 30 grams (0.13 moles) of naproxen were added while rapidly stirring the reaction mixture (a vigorous evolution of hydrogen chloride and sulfur dioxide was observed). After completing the acid addition, the water bath was heated at 80° C. for 30 minutes while stirring.

Naproxenamide was then prepared in a 1-liter flask surrounded by an ice-salt freezing mixture and equipped with an efficient mechanical stirrer and a 500 ml dropping funnel. 125 ml of cold concentrated aqueous ammonia (about 25%) were placed in the flask and 20 grams (0.08 moles) naproxyl chloride were added drop-wise while rapidly stirring the reaction mixture and maintaining the temperature below 15° C., and the evolution of white fumes (mostly ammonium chloride) at a controllable rate. Stirring was continued for one hour after the addition of the acid chloride was completed and thereafter the reaction mixture was evaporated to dryness under vacuum. The dry residue of ammonium chloride and naproxenamide was boiled for 10 minutes with 300 ml of dry ethyl acetate, and the boiling solution was filtered rapidly through a fluted filter paper on a large hot funnel. The residue on the filter was extracted with two portions of 100 ml of ethyl acetate, the combined ethyl acetate extracts were cooled to 0° C., and the precipitated crystalline amide was removed by filtration. The filtrate was concentrated to about 30 ml, chilled, and a second crop of amide was collected. The two crops of naproxenamide were combined and dried, first in an oven at 70° C. for 3 hours and then in a vacuum desiccator, to yield 15 grams (80% yield) of naproxen amide as glistening white needles.

Pet-17 was then prepared from naproxenamide according to the general procedure described above and the procedure for the preparation of Pet-2, as is illustrated in Scheme 7 below. Pet-17 was obtained in an overall yield of 25%.

$^1$H-NMR (CDCl$_3$): δ=1.72 (s, 3H, CH$_3$), 2.42(s, 3H, CH$_3$), 2.81 (t, 2H, CH$_2$), 3.75 (s, 3H, OCH$_3$), 3.85 (t, 2H, CH$_2$ONO$_2$), 4.33(q, 1H, CH), 7.11-7.58 (m, 6H, aromatic) ppm.

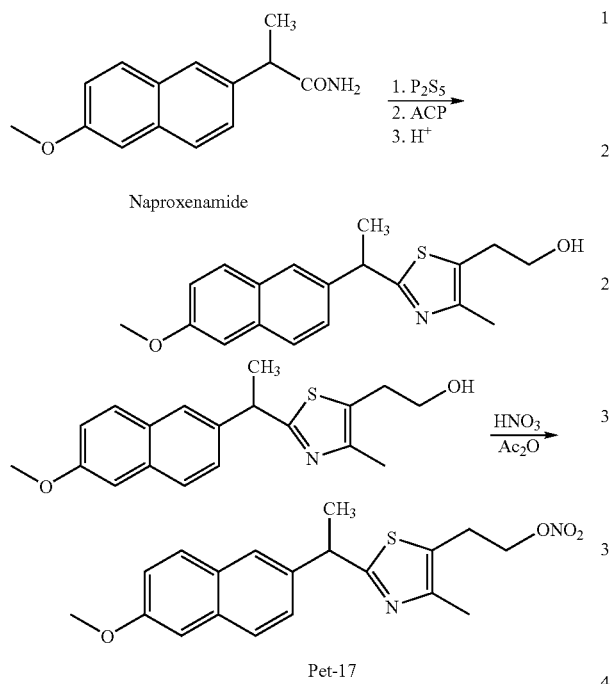

Scheme 7

Naproxenamide

Pet-17

Preparation of 4-methyl-5-(2-nitrooxy-ethyl)-2-(4-trifluoromethyl-phenyl)-thiazole (Pet-59)

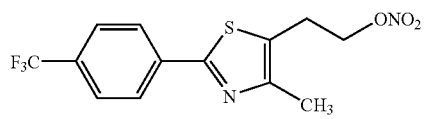

Pet-59 was prepared according to general procedure presented hereinabove and the procedure described above for the preparation of Pet-7, using 4-(trifluoromethyl)-thiobenzamide (obtained from Avocado, UK) as the starting material. The respective alcohol was obtained in 73% yield as brown crystals whereby Pet-59 was obtained as pale brown crystals (74% yield) having a purity of 99% as determined by thin-layer chromatography and gas chromatography.

$^1$H-NMR (CDCl$_3$) of the alcohol intermediate: δ=2.42 (s, 3H, CH$_3$), 3.01 (t, 2H, CH$_2$, J=6 Hz), 3.85 (t, 2H, CH$_2$OH, J=6 Hz) ppm. $^1$H-NMR of Pet-59 (CDCl$_3$): δ=2.43 (s, 3H, CH$_3$), 3.18 (t, 2H, CH$_2$, J=6.6 Hz), 4.60 (t, 2H, CH$_2$ONO$_2$, J=6.6 Hz) ppm.

Preparation of 2-[1-(4-isobutyl-phenyl)-ethyl]-4-methyl-5-(2-nitrooxy-ethyl)-thiazole (Pet-66)

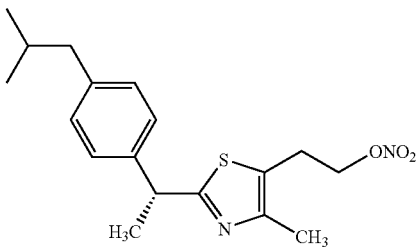

Pet-66 was prepared according to general procedure presented hereinabove and the procedure described above for the preparation of Pet-2, using the respective amide as the starting material, in an overall 35% yield.

$^1$H-NMR (CDCl$_3$): δ=2.68 (s, 3H, CH$_3$), 2.82 (q, 2H, CH$_2$ benzylic, J=11.3 Hz), 3.86 (t, 2H, CH$_2$ONO$_2$, J=10.2 Hz) ppm.

Preparation of Bis-[4-methyl-5-(2-nitrooxy-ethyl)-thiazol-2-yl]-diazene (Pet-102)

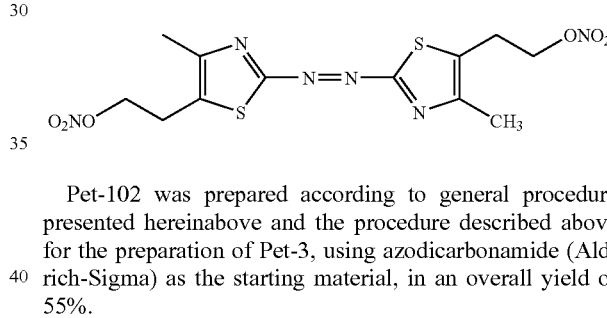

Pet-102 was prepared according to general procedure presented hereinabove and the procedure described above for the preparation of Pet-3, using azodicarbonamide (Aldrich-Sigma) as the starting material, in an overall yield of 55%.

$^1$H-NMR (CDCl$_3$): δ=2.62 (s, 6H, 2×CH$_3$), 2.82(q, 4H, 2×CH$_2$), 3.86(t, 4H, 2×CH$_2$ONO$_2$) ppm.

Preparation of acetic acid 2-[4-methyl-5-(2-nitrooxy-ethyl)-thiazol-2-yl]-phenyl ester (Pet-116)

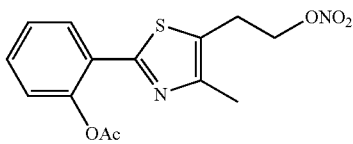

The synthesis of Pet-116 is illustrated in Scheme 8 below.

Scheme 8

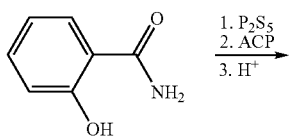

-continued

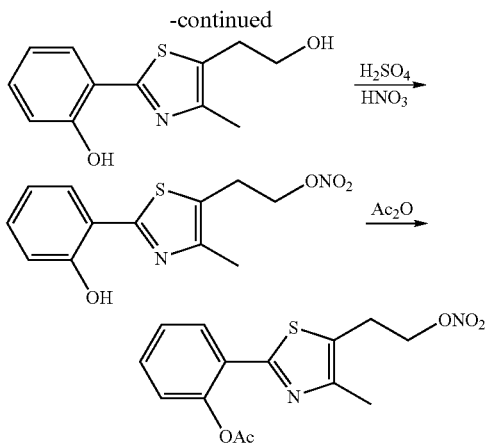

2-[5-(2-Hydroxy-ethyl)-4-methyl-thiazol-2-yl)-phenol was prepared from the respective amide, according to the general procedure described above, using toluene as the solvent, to give a pink powder (55% yield), which was purified by column chromatography on silica gel using a mixture of 3:2:2 ethyl acetat:chloroform:hexane as eluent.

Nitration of 2-[5-(2-Hydroxy-ethyl)-4-methyl-thiazol-2-yl)-phenol was carried out according to the procedures described above, to give 2-[4-Methyl-5-(2-nitrooxy-ethyl-thiazol-2-yl]-phenol as a yellow powder (63% yield).

2-[4-Methyl-5-(2-nitrooxy-ethyl-thiazol-2-yl]-phenol was then subjected to an acetylation reaction, which was carried out according to the procedure described in *Organic Syntheses*, CV3, 452, to give the final product in 70% yield.

$^1$H-NMR (CDCl$_3$): δ=2.10 (s, 3H, COCH$_3$), 2.42(s, CH$_3$, Aromatic), 3.75 (t, 2H, CH$_2$-benzylic), 3.87 (t, CH$_2$ONO$_2$), 7.13-7.47 (m, 4H, Aromatic) ppm.

Preparation of 4,4'-dimethyl-5,5'-bis-(2-nitrooxy-ethyl)-[2,2']bithiazolyl (Pet-118)

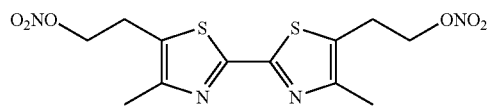

Pet-118 was prepared according to the general procedure presented hereinabove, using dithiooxalamide (obtained from Merck, Germany) as a starting material. The synthesis of the respective alcohol, 2-[5'-(2-Hydroxy-ethyl)-4,4'-dimethyl-[2,2']bithiazolyl-5-yl]-ethanol is illustrated in Scheme 9 below.

Scheme 9

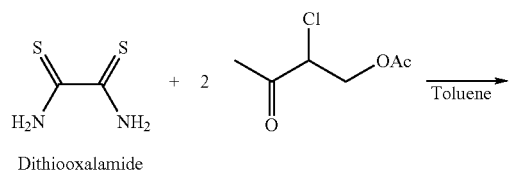

Dithiooxalamide

-continued

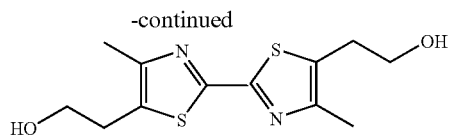

Pet-118 was obtained in 43% yield, as a yellow powder having a purity of 97%, as determined by TLC.

$^1$H-NMR (CDCl$_3$): δ=2.45 (s, 3H, CH$_3$), 2.79 (q, 2H, CH$_2$ benzylic, J=11.1 Hz), 3.05 (t, 2H, CH$_2$, J=10 Hz), 4.46 (t, 2H, CH$_2$ONO$_2$, J=10.2 Hz) ppm.

Using the general procedure and the exemplary procedures described above, Pet-2, Pet-3, Pet-4, Pet-5, Pet-6, Pet-7, Pet-9, Pet-11, Pet-13, Pet-17, Pet-44, Pet-55, Pet-66, Pet-97, Pet-116, Pet-118, Pet-181, Pet-182, Pet-183, Pet-184, Pet-185 and Pet-186 presented in Tables 1 and 2, were prepared and analyzed.

Other 2-substituted-4-methyl-5-(2-nitrooxy-ethyl)-thiazoles, as presented, for example, in Tables 1 and 2, are similarly prepared.

Preparation of NO-Donors Having a Biocleavable Moiety—General Procedure

The procedure presented hereinbelow is general procedure for the preparation of thiazole-based NO-donor according to a preferred embodiment of the present invention, having a biocleavable moiety between the thiazole residue and an additional moiety that is lined thereto. This procedure relies on the general synthetic pathway for preparing the desired 2-(2-substituted-4-methyl-thiazol-5-yl)-ethanol derivative (Compound III) as presented hereinabove and described in Schemes 2 and 3, which serve as thiazole-based NO-donor compounds according to a preferred embodiment of the present invention.

The general procedure is presented in Scheme 10 below. In general, a reactive derivative of a 2-(2-substituted-4-methyl-thiazol-5-yl)-ethanol (Compound V, Scheme 10), is first prepared, and is thereafter reacted with a desired compound having a second reactive group (K-X, Scheme 10). The first and the second reactive groups are selected capable of reacting therebetween, to thereby form a biocleavable moiety (A, Scheme 10). The resulting compound (Compound VI) thus includes a thiazole moiety and a residue of the desired compound covalently linked therebetween by a biocleavable moiety.

Scheme 10

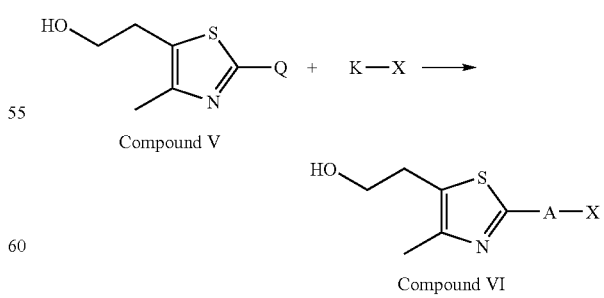

Thus, according to a representative synthetic pathway, the first reactive group on the thiazole derivative (Q in Compound V, Scheme 10) is, for example, an amine, the corresponding second reactive group on the desired compound (K) is, for example, a carboxylic acid, and the formed biocleavable moiety is, for example, an amide. The synthesis in this case is effected by adding dicyclohexylcarbodiimide (DCC) to an equal molar amount of the carboxylic acid derivative in dichloromethane. The mixture is stirred for 2 hours, followed by the addition of an equal molar amount of 4-methyl-5-(2-nitrooxy-ethyl)-thiazole-2-ylamine (Pet-10, prepared as described hereinabove). The reaction mixture is stirred for 8 hours, after which the organic layer is removed and washed with 5% NaOH solution followed by 5% HCl solution and finally with two portions of water to remove excess starting materials. The dichloromethane is dried using sodium sulfate and removed by evaporation to afford the corresponding [5-(2-hydroxy-ethyl)-4-methyl-thiazol-2-yl]-amide.

In accordance with the representative general synthetic pathway presented hereinabove, the nitration of the [5-(2-hydroxy-ethyl)-4-methyl-thiazol-2-yl]-amide is afforded by the addition of 70% nitric acid to acetic anhydride while stirring and maintaining the temperature between 20-30° C. by external cooling. The mixture is then cooled to −5° C. while stirring, followed by the addition of the [5-(2-hydroxy-ethyl)-4-methyl-thiazol-2-yl]-amide. The mixture is kept for 30 minutes at −5° C. and then heated to 10° C. and stirred for one hour. The resulting mixture is poured thereafter into ice water and stirred for 1 hour. Aliquots of NaHCO$_3$ are added until CO$_2$ evolution ceases. The aqueous phase is extracted with three portions of ethyl acetate, and the combined extracts are dried over sodium sulfate and concentrated by evaporation (Scheme 11).

Using the general procedure described hereinabove, a variety of NO-donor compounds having a biocleavable moiety according to the present invention were prepared, as is detailed hereinbelow.

Preparation of N-[4-Methyl-5-(2-nitrooxy-ethyl)-thiazol-2-yl]-nicotinamide (Pet-154)

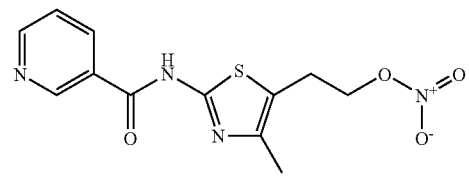

According to the general procedure presented hereinabove, 16.7 grams (0.081 mol) of dicyclohexylcarbodiimide (DCC) were added to 10 grams (0.081 mol) of nicotinic acid in dichloromethane. The mixture was stirred for 2 hour, followed by the addition of 12.8 grams (0.081 mol) of 2-(2-amino-4-methyl-thiazol-5-yl)-ethanol. The reaction mixture was stirred for additional 8 hours, after which the organic layer was removed and washed with 5% NaOH solution followed by 5% HCl solution and finally with two portions of water to remove excess starting materials. The dichloromethane was dried using sodium sulfate and removed by evaporation to afford 13 grams (61%) of pale yellow powder of N-[5-(2-hydroxy-ethyl)-4-methyl-thiazol-2-yl]-nicotinamide, as described in Scheme 12 hereinbelow.

Scheme 11

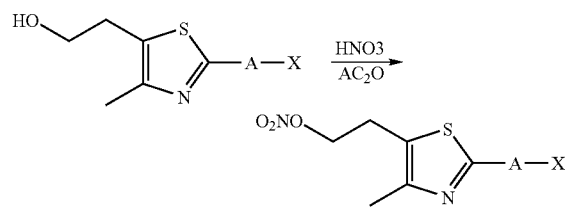

In a second example, the first reactive group on the thiazole derivative (Q in Compound V, Scheme 10) is, for example, hydroxyl, the corresponding second reactive group on the desired compound (K) is, for example, a carboxylic acid, and the formed biocleavable moiety is, for example, an ester. The synthesis in this case is executed by reacting an equal molar amount of the carboxylic acid derivative and an equal molar amount of the thiazole derivative in the presence of a catalytic amount of an acid or an equal molar amount of a base.

In another example, the first reactive group on the thiazole derivative (Q in Compound V, Scheme 10) is, for example, a carboxylic acid, and the corresponding second reactive group on the desired compound (K) is, for example, hydrazine, and the formed biocleavable moiety is, for example, hydrazide. The synthesis in this case is effected by an equal molar amount of the carboxylic acid derivative and an equal molar amount of the thiazole derivative in the presence of a catalytic amount of an acid.

The nitration step for the general examples above is carried out in accordance with the representative general synthetic pathway for the biocleavable amide described hereinabove.

Scheme 12

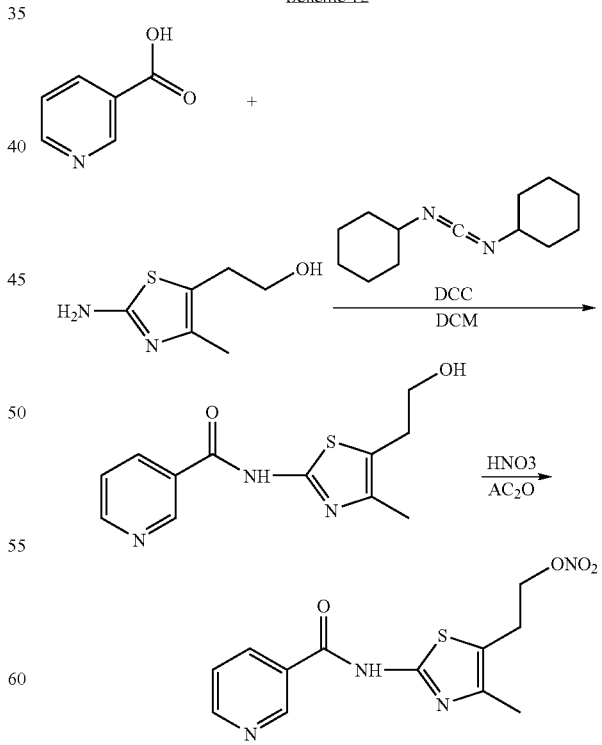

Pet-154

70% nitric acid (1.2 ml) was added to acetic anhydride (5 ml) while stirring and maintaining the temperature between 20-30° C. by external cooling. The mixture was cooled to −5° C. while stirring, followed by the addition of 1 gram of N-[5-(2-hydroxy-ethyl)-4-methyl-thiazol-2-yl]-nicotinamide. After 30 minutes at −5° C. the mixture was heated to 10° C. and stirred for one additional hour. The resulting mixture was poured into ice-water and stirred for 1 hour. Aliquots of NaHCO₃ were added until CO₂ evolution ceased. The orange-yellow water solution was extracted with three portions of 15 ml ethyl acetate. The combined extracts were dried over sodium sulfate and concentrated by evaporation.

¹H-NMR (CDCl₃): δ=2.48 (s, 3H, CH₃), 3.39 (q, 2H, CH₂ benzylic), 4.08 (t, 2H, CH₂ONO₂), 7.24-8.87 (m, 4H, Pyridinic) ppm.

Preparation of 2-(6-methoxy-naphthalen-2-yl)-N-[4-methyl-5-(2-nitrooxy-ethyl)-thiazol-2-yl]-propionamide (Pet-150)

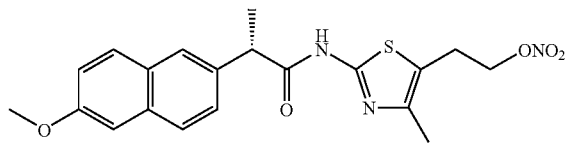

Pet-150 was prepared according to the general procedure described hereinabove and the procedure described above for the preparation of Pet-154, using 2-(5-methoxy-naphthalen-2-yl)-propionic acid (Naproxen) and 4-methyl-5-(2-nitrooxy-ethyl)-thiazol-2-ylamine (Pet-10) as the starting materials, in an overall yield of 43%.

¹H-NMR (CDCl₃): δ=1.56 (d, 1H, CH-naphtylic), 2.37 (s, 3H, CH₃), 2.49 (s, 3H, CH₃), 3.33 (q, 2H, CH₂ benzylic), 3.89 (s, 3H, O—CH₃) 4.01 (t, 2H, CH₂ONO₂), 7.04-7.67 (m, 4H, naphthylic) ppm.

Preparation of 5-[1,2]Dithiolan-3-yl-pentanoic acid [4-methyl-5-(2-nitrooxy-ethyl)-thiazol-2-yl]-amide (Pet-151)

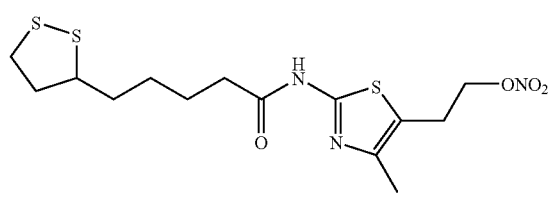

Pet-151 was prepared according to the general procedure described hereinabove and the procedure described above for the preparation of Pet-154, using 5-[1,2]Dithiolan-3-yl-pentanoic acid (DL-Lipoic acid) and 4-methyl-5-(2-nitrooxy-ethyl)-thiazol-2-ylamine (Pet-10) as the starting materials, in an overall yield of 51% as a pale yellow liquid.

¹H-NMR (CDCl₃): δ=1.61 (m, 2H, CH₂, alpha-S), 1.66 (m, 2H, CH₂, beta-S), 1.90 (m, 2H, CH₂, beta-C═(O)N), 2.25 (s, 3H, CH₃), 2.36 (m, 2H, CH₂), 2.89 (t, 2H, CH₂, 3.54 (m, 1H, CH—S—CH₂), 3.80 (t, 2H, CH₂—ONO₂), 6.91 (s, 1H, NH-amide) ppm.

Preparation of 2-(4-Isobutyl-phenyl)-N-[4-methyl-5-(2-nitrooxy-ethyl)-thiazol-2-yl]-propionamide (Pet-152)

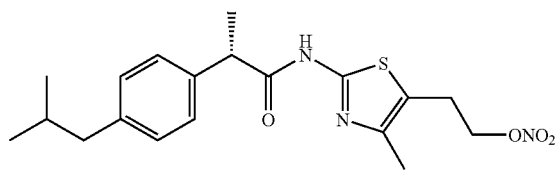

Pet-152 was prepared according to the general procedure described hereinabove and the procedure described above for the preparation of Pet-154, using 2-(4-isobutyl-phenyl)-propionic acid (Ibuprofen) and 4-methyl-5-(2-nitrooxy-ethyl)-thiazol-2-ylamine (Pet-10) as the starting materials, in an overall yield of 63%.

¹H-NMR (CDCl₃): δ=0.86 (m, 6H, CH—(CH₃)₂, 1.18 (t, 2H, CH₂), 1.57 (d, 1H, CH—CH₃), 2.21 (s, 3H, CH₃), 2.70 (m, 2H, CH₂), 3.06 (t, 2H, CH₂), 3.41 (q, 3H, CH₃—CH,), 3.81 (q, 1H, CH₃—CH), 4.52 (t, 2H, CH₂—ONO2), 7.12-7.83 (m, 4H, aromatic) ppm.

Preparation of N-[4-methyl-5-(2-nitrooxy-ethyl)-thiazol-2-yl]-1-oxy-nicotinamide (Pet-156)

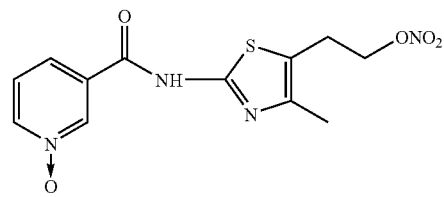

Pet-156 was prepared according to the general procedure described hereinabove and the procedure described above for the preparation of Pet-154, using 1-oxy-nicotinic acid and 4-methyl-5-(2-nitrooxy-ethyl)-thiazol-2-ylamine (Pet-10) as the starting materials, in an overall yield of 71%.

¹H-NMR (CDCl₃): δ=2.49 (s, 3H, CH₃), 3.32(q, 2H, CH₂ benzylic), 4.18 (t, 2H, CH₂ONO₂), 7.26-8.98 (m, 4H, Pyridinic) ppm Preparation of 4-acetylamino-N-[4-methyl-5-(2-nitrooxy-ethyl)-thiazol-2-yl]-benzamide (Pet-157)

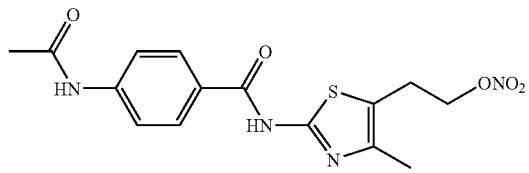

Pet-157 was prepared according to the general procedure described hereinabove and the procedure described above for the preparation of Pet-154, using 4-acetylamino-benzoic acid and 4-methyl-5-(2-nitrooxy-ethyl)-thiazol-2-ylamine (Pet-10) as the starting materials, in an overall yield of 44%.

¹H-NMR (CDCl₃): δ=2.48 (s, 3H, CH₃), 3.29 (q, 2H, CH₂ benzylic), 3.90 (s, 3H, CH₃), 4.01 (t, 2H, CH₂ONO₂), 6.66-7.87 (m, 4H, aromatic) ppm Preparation of hexadecanoic acid [4-methyl-5-(2-nitrooxy-ethyl)-thiazol-2-yl]-amide (Pet-158)

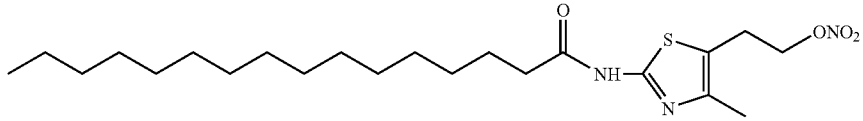

Pet-158 was prepared according to the general procedure described hereinabove and the procedure described above for the preparation of Pet-154, using hexadecanoic acid (palmitic acid) and 4-methyl-5-(2-nitrooxy-ethyl)-thiazol-2-ylamine (Pet-10) as the starting materials, in an overall yield of 62%.

Preparation of acetic acid 2-[4-methyl-5-(2-nitrooxy-ethyl)-thiazol-2-ylcarbamoyl]-phenyl ester (Pet-159)

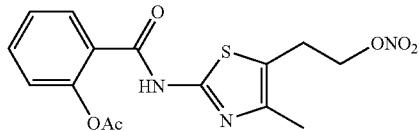

Pet-159 was prepared according to the general procedure described hereinabove and the procedure described above for the preparation of Pet-154, using 2-acetoxy-benzoic acid (Aspirin) and 4-methyl-5-(2-nitrooxy-ethyl)-thiazol-2-ylamine (Pet-10) as the starting materials, in an overall yield of 25%.

¹H-NMR (CDCl₃): δ=2.44 (s, 3H, CH₃), 3.33 (q, 2H, CH₂ benzylic), 3.85 (s, 3H, CH₃), 4.01 (t, 2H, CH₂ONO₂), 7.02-7.87 (m, 4H, aromatic) ppm Preparation of Pyrrolidine-2-carboxylic acid [4-methyl-5-(2-nitrooxy-ethyl)-thiazol-2-yl]-amide (Pet-160)

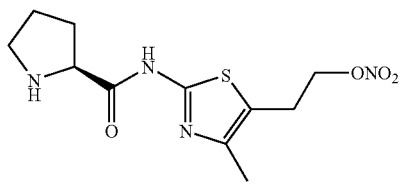

Pet-160 was prepared according to the general procedure described hereinabove and the procedure described above for the preparation of Pet-154, using pyrrolidine-2-carboxy-lic acid and 4-methyl-5-(2-nitrooxy-ethyl)-thiazol-2-ylamine (Pet-10) as the starting materials, in an overall yield of 55%.

¹H-NMR (CDCl₃): δ=1.60 (m, 2H, CH₂, Pyrolidine), 1.88 (m, 2H, CH₂, pyrolodine, 1-beta-C(=O)—N), 2.44 (s, 3H, CH₃), 2.78 (m, 2H, CH₂, pyrolodine), 3.38 (q, 2H, CH₂ benzylic), 3.88 (s, 3H, CH₃), 4.07 (t, 2H, CH₂ONO₂) ppm.

Preparation of 2,6-difluoro-N-[4-methyl-5-(2-nitrooxy-ethyl)-thiazol-2-yl]-benzamide (Pet-161)

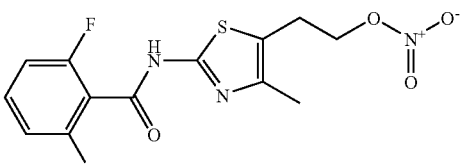

Pet-161 was prepared according to the general procedure described hereinabove and the procedure described above for the preparation of Pet-154, using 2,6-difluoro-benzoic acid and 4-methyl-5-(2-nitrooxy-ethyl)-thiazol-2-ylamine (Pet-10) as the starting materials, in an overall yield of 72%.

¹H-NMR (CDCl₃): δ=2.46 (s, 3H, CH₃), 3.34 (q, 2H, CH₂ benzylic), 4.12 (t, 2H, CH₂ONO₂), 7.24-8.88 (m, 3H, aromatic) ppm.

Preparation of 2-(2,4-dichloro-phenyl)-N-[4-methyl-5-(2-nitrooxy-ethyl)-thiazol-2-yl]-acetamide (Pet-162)

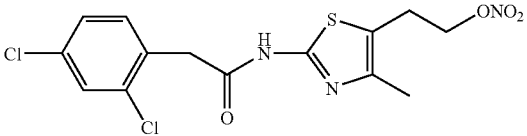

Pet-162 was prepared according to the general procedure described hereinabove and the procedure described above for the preparation of Pet-154, using (2,4-dichloro-phenyl)-acetic acid and 4-methyl-5-(2-nitrooxy-ethyl)-thiazol-2-ylamine (Pet-10) as the starting materials, in an overall yield of 69%.

¹H-NMR (CDCl₃): δ=2.47 (s, 3H, CH₃), 3.38(q, 2H, CH₂ benzylic), 4.12 (t, 2H, CH₂ONO₂), 7.24 (dd, 2H, aromatic), 8.45 (s, 1H, aromatic) ppm.

Preparation of 2-(2,4-dichloro-phenoxy)-N-[4-methyl-5-(2-nitrooxy-ethyl)-thiazol-2-yl]-acetamide (Pet-163)

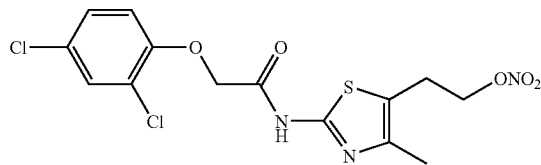

Pet-163 was prepared according to the general procedure described hereinabove and the procedure described above for the preparation of Pet-154, using (2,4-dichloro-phenoxy)-acetic acid and 4-methyl-5-(2-nitrooxy-ethyl)-thiazol-2-ylamine (Pet-10) as the starting materials, in an overall yield of 77%.

$^1$H-NMR (CDCl$_3$): δ=2.36 (s, 3H, CH$_3$), 3.30 (q, 2H, CH$_2$ benzylic), 4.05 (t, 2H, CH$_2$ONO$_2$), 4.45 (s, 2H, CH$_2$), 7.11 (dd, 2H, aromatic), 8.23 (s, 1H, aromatic) ppm.

Preparation of 4-methyl-5-(2-nitrooxy-ethyl)-thiazole-2-carboxylic acid N'-phthalazin-1-yl-hydrazide (Pet-153)

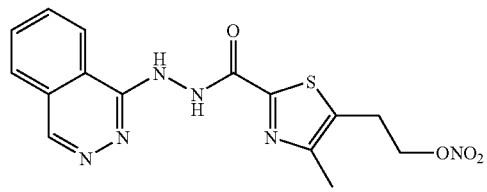

Pet-153 was prepared according to the general procedure described hereinabove and the procedure described above for the preparation of Pet-154, using phthalazin-1-yl-hydrazine and 5-(2-Hydroxyethyl)-4-methylthiazole-2-carboxylic acid as the starting materials, in an overall yield of 47%.

$^1$H-NMR (CDCl$_3$): δ=2.39 (s, 3H, CH$_3$), 3.33 (t, 2H, CH$_2$ benzylic), 3.85 (t, 2H, CH$_2$ONO$_2$), 4.45 (s, 1 H, NHaromatic C—NH), 7.66-8.87 (m, 5H, aromatic) ppm.

Preparation of allyl-[4-methyl-5-(2-nitrooxy-ethyl)-thiazol-2-yl]-amine (Pet-155)

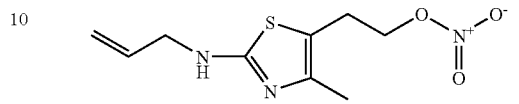

Pet-155 was prepared according to the general procedure described hereinabove and the procedure described above for the preparation of Pet-7, using allylthiourea and ACP as the starting materials, in an overall yield of 87%.

Preparation of 4-methyl-5-(2-nitrooxy-ethyl)-thiazole-2-carboxylic acid 10,13-dimethyl-3-oxo-2,3,6,7,8,9,10,11,12,13,14,15,16,17-tetradecahydro-1H-cyclopenta[a]phenanthren-17-yl ester (Pet-164)

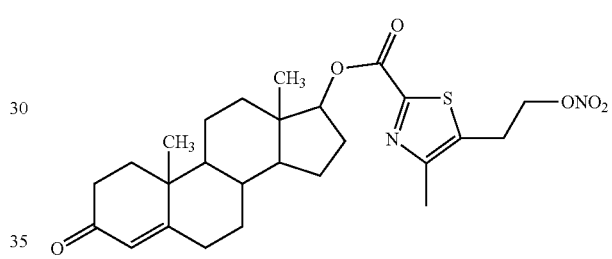

Pet-164 was prepared by a catalytic acid esterification reaction of 5-(2-Hydroxyethyl)-4-methylthiazole-2-carboxylic acid with commercial available (Sigma) testosterone to afford the title compound in an overall yield of 34%.

Other 2-substituted-4-methyl-5-(2-nitrooxy-ethyl)-thiazole derivatives having a biocleavable moiety, as shown in Tables 1 and 2, have been similarly prepared.

TABLE 1

| Compound | Chemical Structure |
| --- | --- |
| Pet-2 | 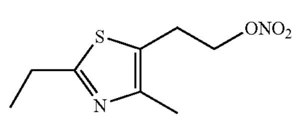 |
| Pet-3 | 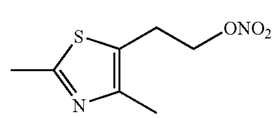 |
| Pet-4 | 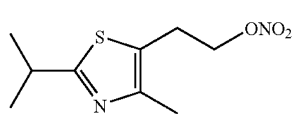 |

TABLE 1-continued

| Compound | Chemical Structure |
|---|---|
| Pet-5 | 2-[(1R)-1-(nitrooxy)ethyl]-4-methyl-5-(2-nitrooxyethyl)thiazole |
| Pet-6 | 2-(trifluoromethyl)-4-methyl-5-(2-nitrooxyethyl)thiazole |
| Pet-7 | 2-(dimethylamino)-4-methyl-5-(2-nitrooxyethyl)thiazole |
| Pet-8 | 2-phenyl-4-methyl-5-(2-nitrooxyethyl)thiazole |
| Pet-9 | 2-methoxy-4-methyl-5-(2-nitrooxyethyl)thiazole |
| Pet-10 | 2-amino-4-methyl-5-(2-nitrooxyethyl)thiazole |
| Pet-11 | 2-(piperidin-4-yl)-4-methyl-5-(2-nitrooxyethyl)thiazole |
| Pet-12 | 2-(pyridin-3-yl)-4-methyl-5-(2-nitrooxyethyl)thiazole |
| Pet-13 | bis-thiazole linked by butylene, 4-methyl-5-(2-nitrooxyethyl) on each |
| Pet-14 | 2-(benzyloxy)-4-methyl-5-(2-nitrooxyethyl)thiazole |
| Pet-15 | bis-thiazole linked by ethylene, 4-methyl-5-(2-nitrooxyethyl) on each |
| Pet-16 | bis-thiazole linked by methylene, 4-methyl-5-(2-nitrooxyethyl) on each |

TABLE 1-continued

| Compound | Chemical Structure |
|---|---|
| Pet-17 | (S)-2-(1-(6-methoxynaphthalen-2-yl)ethyl)-4-methylthiazol-5-yl ethyl nitrate derivative |
| Pet-18 | 2-(2-chloro-6-(trifluoromethyl)pyridin-3-yl)-4-methylthiazol-5-yl ethyl nitrate |
| Pet-19 | 2-(4-(diethylamino)pyridin-3-yl)-4-methylthiazol-5-yl ethyl nitrate |
| Pet-20 | 2-(6-methylpyridin-3-yl)-4-methylthiazol-5-yl ethyl nitrate |
| Pet-21 | 2-(pyridin-3-yl N-oxide)-4-methylthiazol-5-yl ethyl nitrate |
| Pet-22 | 2-(6-(trifluoromethyl)pyridin-3-yl)-4-methylthiazol-5-yl ethyl nitrate |
| Pet-23 | 2-(6-methoxypyrazin-2-yl)-4-methylthiazol-5-yl ethyl nitrate |
| Pet-24 | 2-(6-(methylamino)pyrazin-2-yl)-4-methylthiazol-5-yl ethyl nitrate |
| Pet-25 | 2-(2-ethylpyridin-4-yl N-oxide)-4-methylthiazol-5-yl ethyl nitrate |

TABLE 1-continued
| Compound | Chemical Structure |
|---|---|
| Pet-26 | 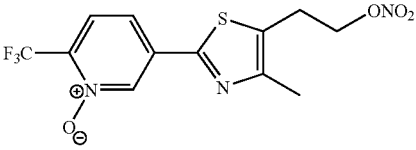 |
| Pet-27 | 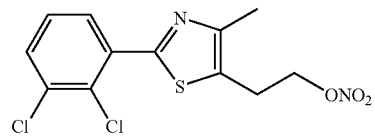 |
| Pet-28 | 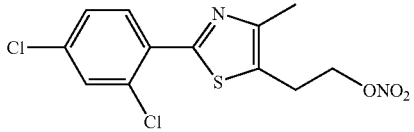 |
| Pet-29 | 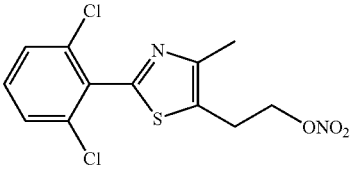 |
| Pet-30 | 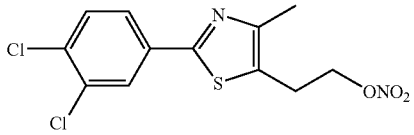 |
| Pet-31 | 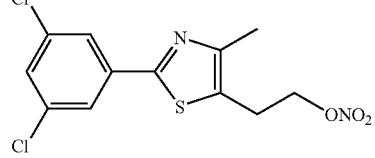 |
| Pet-32 | 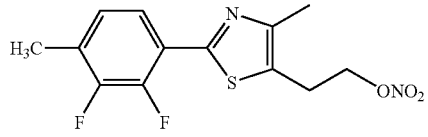 |
| Pet-33 | 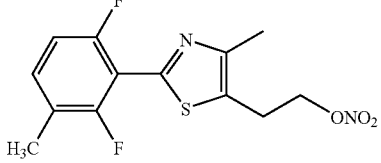 |
| Pet-34 | 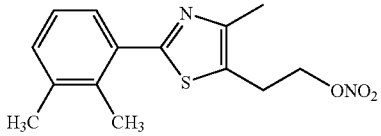 |

TABLE 1-continued

| Compound | Chemical Structure |
|---|---|
| Pet-35 | 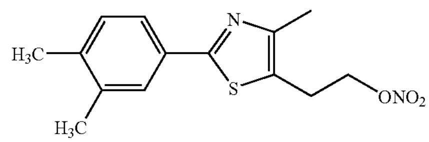 |
| Pet-36 | 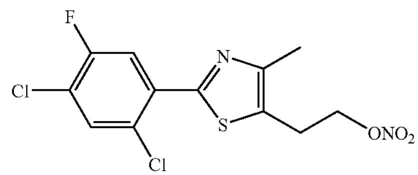 |
| Pet-37 | 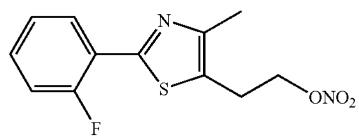 |
| Pet-38 | 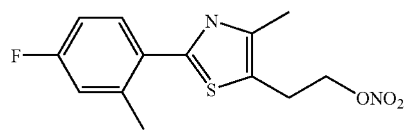 |
| Pet-39 | 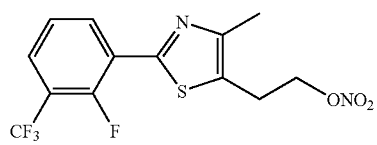 |
| Pet-40 | 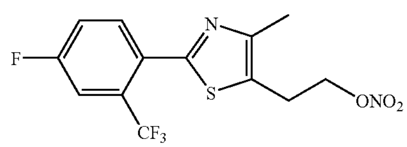 |
| Pet-41 | 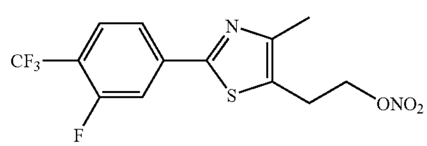 |
| Pet-42 | 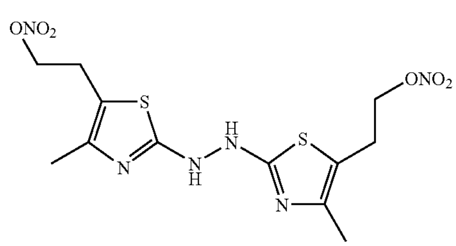 |
| Pet-43 | 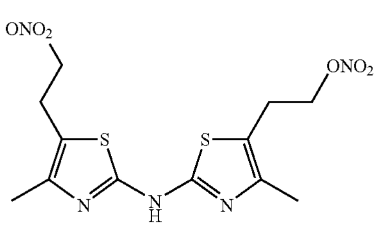 |

TABLE 1-continued

| Compound | Chemical Structure |
|---|---|
| Pet-44 | 2-(pentafluorophenyl)-4-methyl-5-(2-nitrooxyethyl)thiazole |
| Pet-45 | 2-(pentafluoroethyl)-4-methyl-5-(2-nitrooxyethyl)thiazole (CF$_3$CF$_2$-) |
| Pet-46 | 2-(1-phenylethyl)-4-methyl-5-(2-nitrooxyethyl)thiazole |
| Pet-47 | 2-(pentylamino)-4-methyl-5-(2-nitrooxyethyl)thiazole |
| Pet-48 | 2-(2-phenylhydrazinyl)-4-methyl-5-(2-nitrooxyethyl)thiazole |
| Pet-49 | 2-(1-amino-3-methylbutyl)-4-methyl-5-(2-nitrooxyethyl)thiazole |
| Pet-50 | 2-(hydroxyamino)-4-methyl-5-(2-nitrooxyethyl)thiazole |
| Pet-51 | 2-(aminomethyl)-4-methyl-5-(2-nitrooxyethyl)thiazole (NH$_2$CH$_2$-) |
| Pet-52 | N-(4-methyl-5-(2-nitrooxyethyl)thiazol-2-yl)formamide |
| Pet-53 | N'-(4-methyl-5-(2-nitrooxyethyl)thiazol-2-yl)formohydrazide |

TABLE 1-continued

| Compound | Chemical Structure |
|---|---|
| Pet-54 | 4-methyl-5-(2-nitrooxyethyl)thiazol-2-yl disulfide (bis[4-methyl-5-(2-nitrooxyethyl)thiazol-2-yl] disulfide) |
| Pet-55 | 2-(2,3,4,5-tetrafluorophenyl)-4-methyl-5-(2-nitrooxyethyl)thiazole |
| Pet-56 | 2-(4-chlorophenyl)-4-methyl-5-(2-nitrooxyethyl)thiazole |
| Pet-57 | 2-(3,4,5-trihydroxyphenyl)-4-methyl-5-(2-nitrooxyethyl)thiazole |
| Pet-58 | 2-(2-fluoro-4,6-dimethylphenyl)-4-methyl-5-(2-nitrooxyethyl)thiazole |
| Pet-59 | 2-(4-trifluoromethylphenyl)-4-methyl-5-(2-nitrooxyethyl)thiazole |
| Pet-60 | 2-(3-trifluoromethylphenyl)-4-methyl-5-(2-nitrooxyethyl)thiazole |
| Pet-61 | 2-(2-trifluoromethylphenyl)-4-methyl-5-(2-nitrooxyethyl)thiazole |
| Pet-62 | 2-(2-trifluoromethoxyphenyl)-4-methyl-5-(2-nitrooxyethyl)thiazole |
| Pet-63 | 2-(4-trifluoromethoxyphenyl)-4-methyl-5-(2-nitrooxyethyl)thiazole |

TABLE 1-continued

| Compound | Chemical Structure |
|---|---|
| Pet-64 | 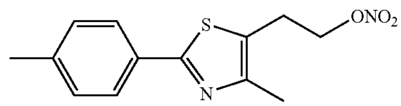 |
| Pet-65 | 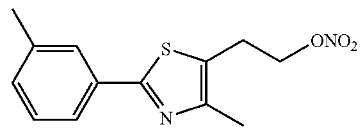 |
| Pet-66 | 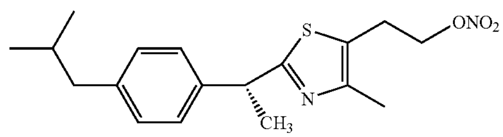 |
| Pet-67 | 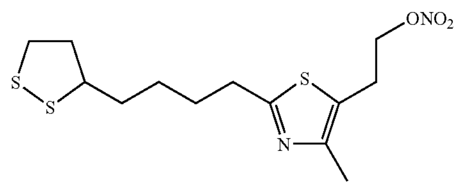 |
| Pet-68 | 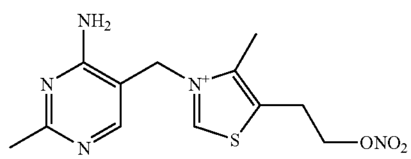 |
| Pet-69 | 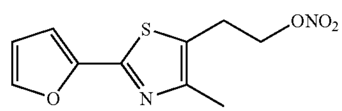 |
| Pet-70 | 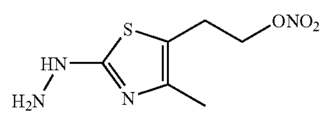 |
| Pet-71 | 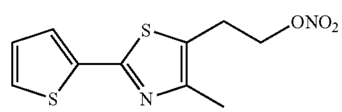 |
| Pet-72 | 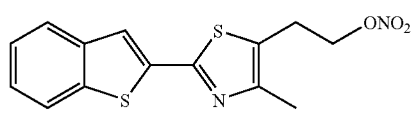 |
| Pet-73 | 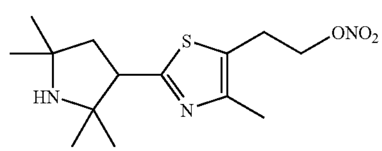 |
| Pet-74 | 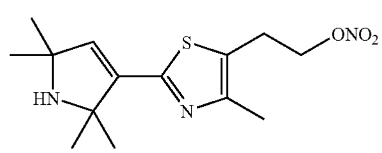 |

TABLE 1-continued

| Compound | Chemical Structure |
|---|---|
| Pet-75 | 3-(2,2,5,5-tetramethyl-1-oxyl-pyrrolidin-3-yl)-4-methyl-5-(2-nitrooxyethyl)thiazole |
| Pet-76 | 2-cyano-N-[4-methyl-5-(2-nitrooxyethyl)thiazol-2-yl]acetamide |
| Pet-77 | 2-(pyrrolidin-2-yl)-4-methyl-5-(2-nitrooxyethyl)thiazole |
| Pet-78 | N-phenyl-4-methyl-5-(2-nitrooxyethyl)thiazol-2-amine |
| Pet-79 | N-{[4-methyl-5-(2-nitrooxyethyl)thiazol-2-yl]methyl}acetamide |
| Pet-80 | N-(pyridin-3-ylmethyl)-4-methyl-5-(2-nitrooxyethyl)thiazol-2-amine |
| Pet-81 | 2-(pyridin-4-yl)-4-methyl-5-(2-nitrooxyethyl)thiazole |
| Pet-82 | 2-(piperidin-3-yl)-4-methyl-5-(2-nitrooxyethyl)thiazole |
| Pet-83 | 2-(3,5-dimethylpyrazol-1-yl)-4-methyl-5-(2-nitrooxyethyl)thiazole |
| Pet-84 | 2-(4-aminopyrimidin-5-yl)-4-methyl-5-(2-nitrooxyethyl)thiazole |
| Pet-85 | 2-vinyl-4-methyl-5-(2-nitrooxyethyl)thiazole |

TABLE 1-continued
| Compound | Chemical Structure |
|---|---|
| Pet-86 | 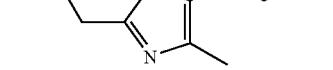 |
| Pet-87 | 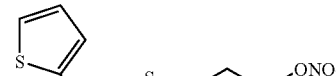 |
| Pet-88 | 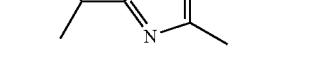 |
| Pet-89 | 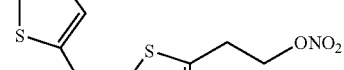 |
| Pet-90 | 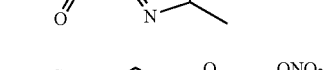 |
| Pet-91 | 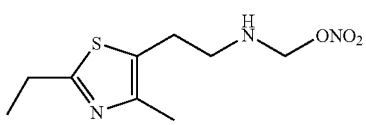 |
| Pet-92 | 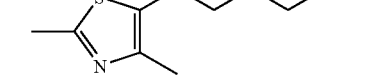 |
| Pet-93 | 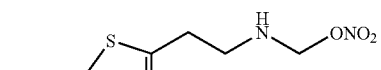 |
| Pet-94 | 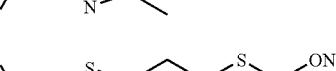 |
| Pet-95 | 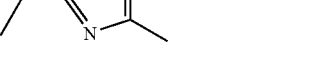 |

TABLE 1-continued

| Compound | Chemical Structure |
|---|---|
| Pet-96 | 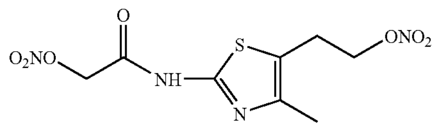 |
| Pet-97 | 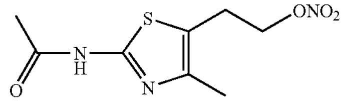 |
| Pet-98 | 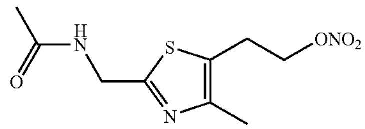 |
| Pet-99 | 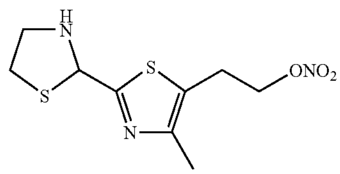 |
| Pet-100 | 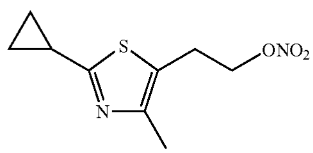 |
| Pet-101 | 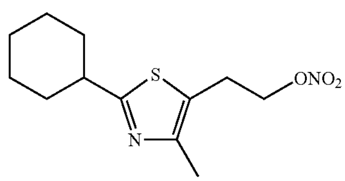 |
| Pet-102 | 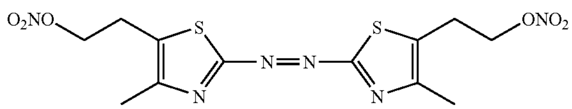 |
| Pet-103 | 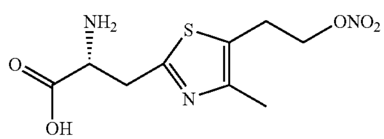 |
| Pet-104 | 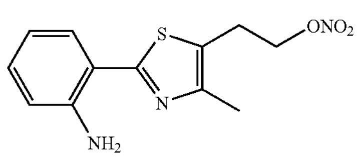 |
| Pet-105 | 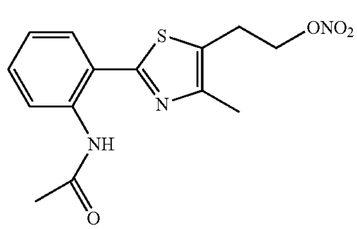 |

TABLE 1-continued
| Compound | Chemical Structure |
|---|---|
| Pet-106 | 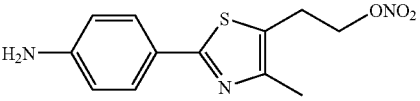 |
| Pet-107 | 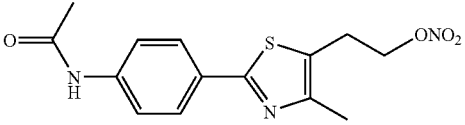 |
| Pet-108 | 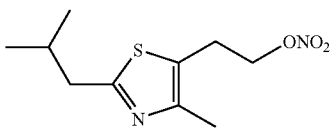 |
| Pet-109 | 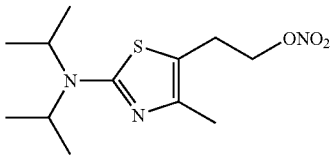 |
| Pet-110 | 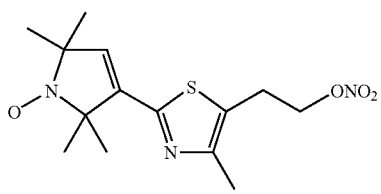 |
| Pet-111 | 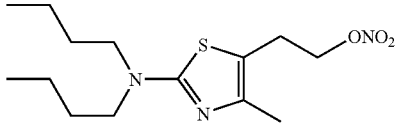 |
| Pet-112 | 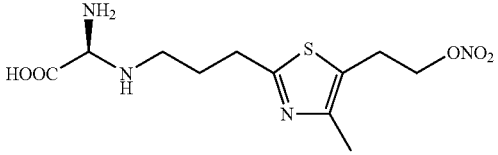 |
| Pet-113 | 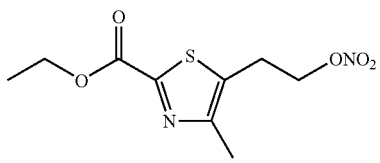 |
| Pet-114 | 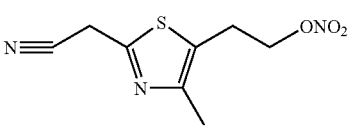 |

TABLE 1-continued

| Compound | Chemical Structure |
| --- | --- |
| Pet-115 | 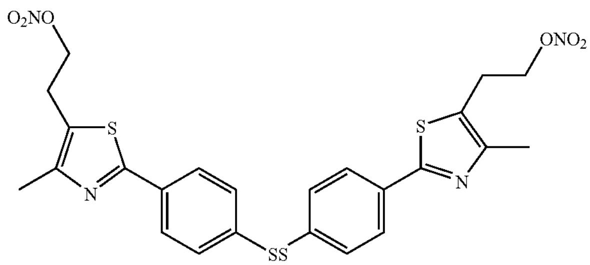 |
| Pet-116 | 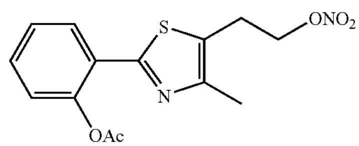 |
| Pet-117 | 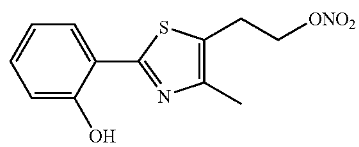 |
| Pet-118 | 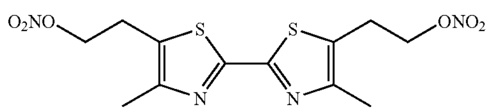 |
| Pet-119 | 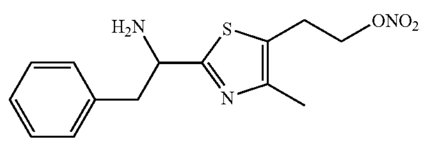 |
| Pet-120 | 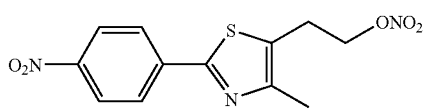 |
| Pet-121 | 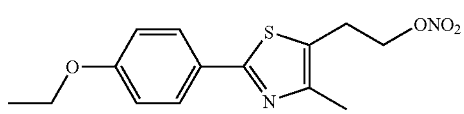 |
| Pet-122 | 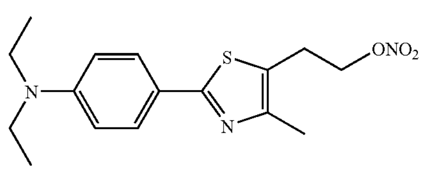 |
| Pet-123 | 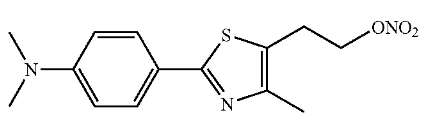 |
| Pet-124 | 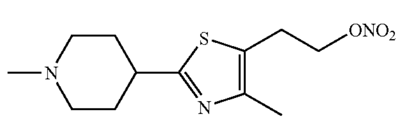 |

TABLE 1-continued

| Compound | Chemical Structure |
|---|---|
| Pet-125 | (pyrazin-2-yl)-4-methylthiazol-5-yl ethyl nitrate |
| Pet-126 | (pyrazine 1-oxide-2-yl)-4-methylthiazol-5-yl ethyl nitrate |
| Pet-127 | (pyrazine 1,4-dioxide-2-yl)-4-methylthiazol-5-yl ethyl nitrate |
| Pet-128 | (naphthalen-1-yl)-4-methylthiazol-5-yl ethyl nitrate |
| Pet-129 | (2-chloro-6-methylphenyl)-4-methylthiazol-5-yl ethyl nitrate |
| Pet-130 | (2-chloro-6-fluorophenyl)-4-methylthiazol-5-yl ethyl nitrate |
| Pet-131 | (2-chloro-4-fluorophenyl)-4-methylthiazol-5-yl ethyl nitrate |
| Pet-132 | (2-chloro-5-fluorophenyl)-4-methylthiazol-5-yl ethyl nitrate |
| Pet-133 | (4-chloro-2-fluorophenyl)-4-methylthiazol-5-yl ethyl nitrate |

TABLE 1-continued
| Compound | Chemical Structure |
|---|---|
| Pet-134 | 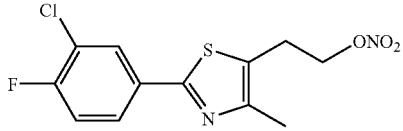 |
| Pet-135 | 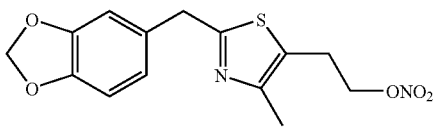 |
| Pet-136 | 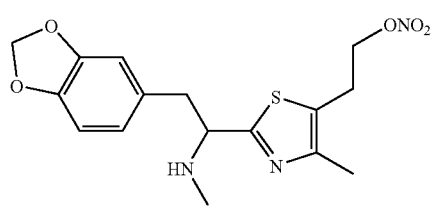 |
| Pet-137 | 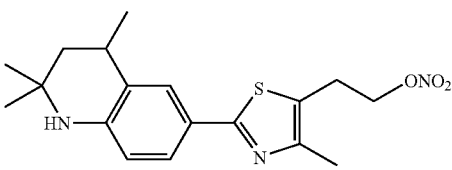 |
| Pet-138 | 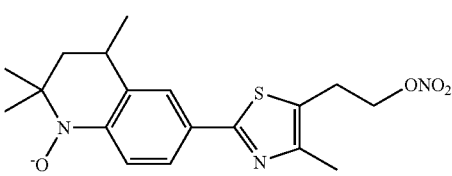 |
| Pet-139 | 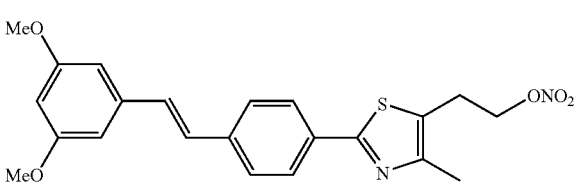 |
| Pet-140 | 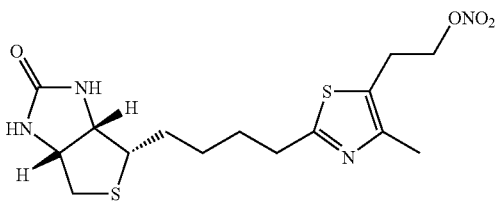 |
| Pet-141 | 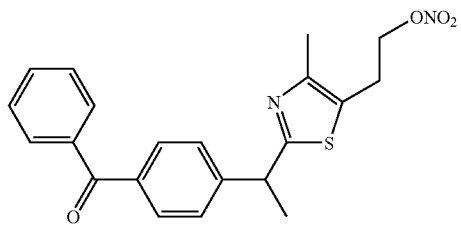 |

TABLE 1-continued
| Compound | Chemical Structure |
|---|---|
| Pet-142 | 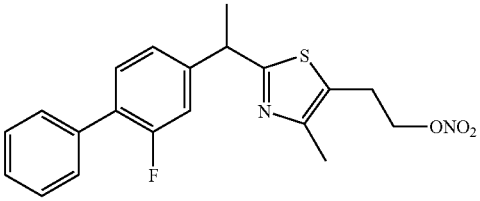 |
| Pet-143 | 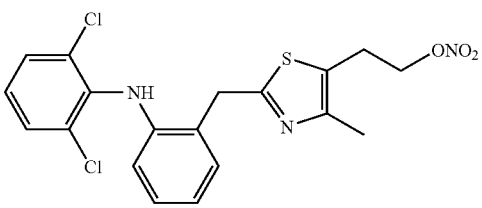 |
| Pet-144 | 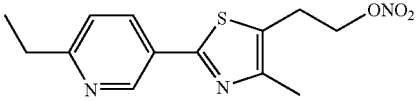 |
| Pet-145 | 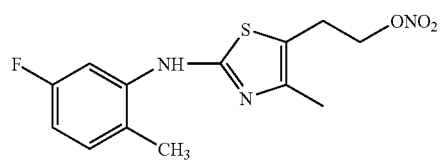 |
| Pet-146 | 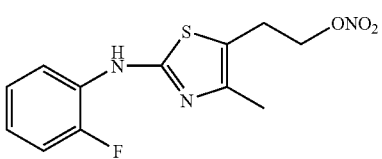 |
| Pet-147 | 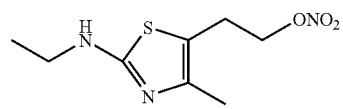 |
| Pet-148 | 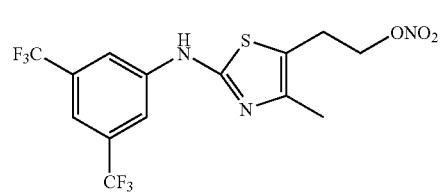 |
| Pet-149 | 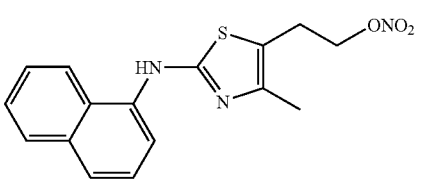 |
| Pet-150 | 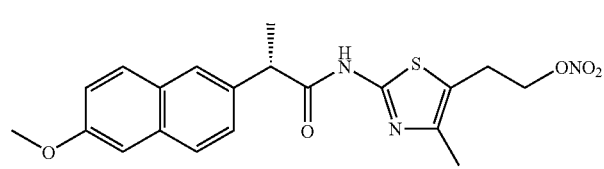 |

TABLE 1-continued

| Compound | Chemical Structure |
|---|---|
| Pet-151 | 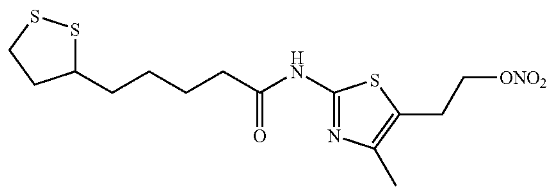 |
| Pet-152 | 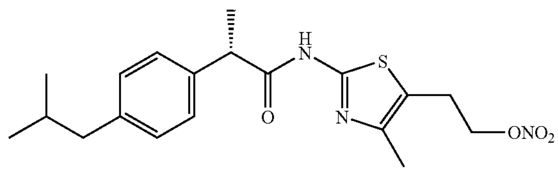 |
| Pet-153 | 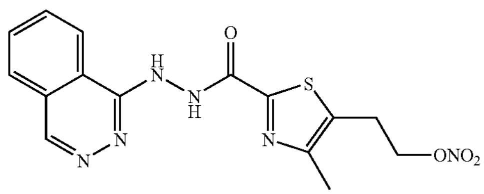 |
| Pet-154 | 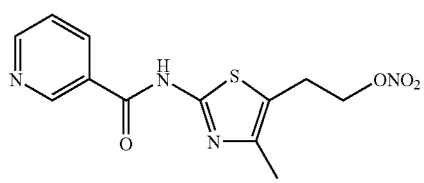 |
| Pet-155 | 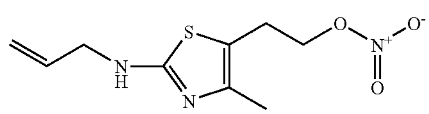 |
| Pet-156 | 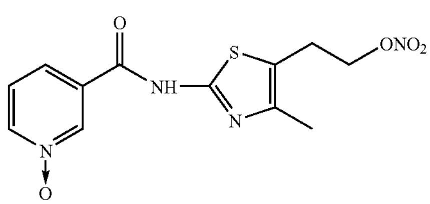 |
| Pet-157 | 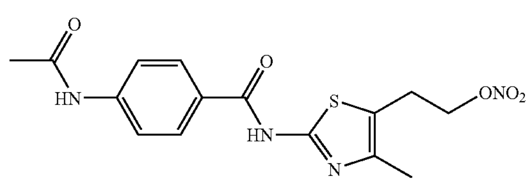 |
| Pet-158 | 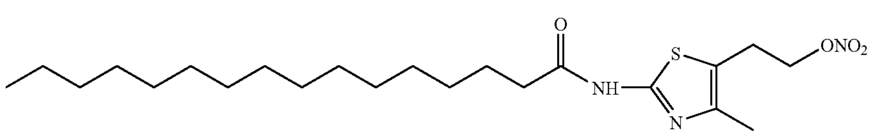 |
| Pet-159 | 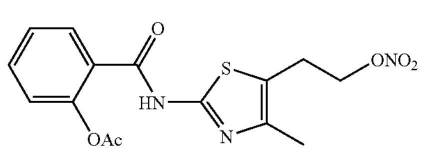 |

TABLE 1-continued

| Compound | Chemical Structure |
|----------|-------------------|
| Pet-160  | 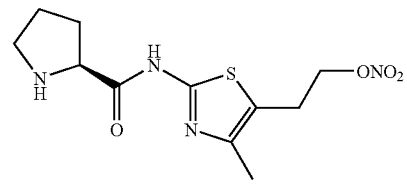 |
| Pet-161  | 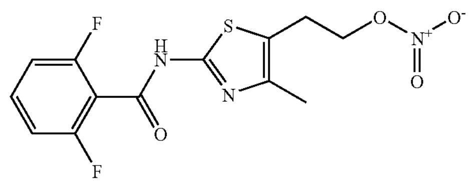 |
| Pet-162  | 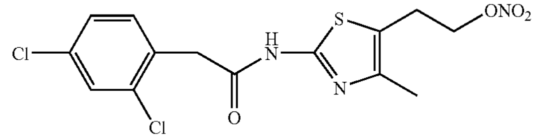 |
| Pet-163  | 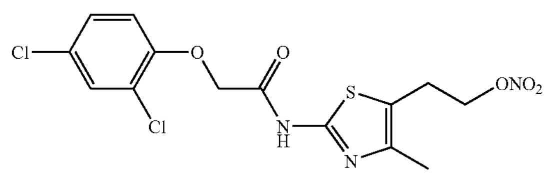 |
| Pet-164  | 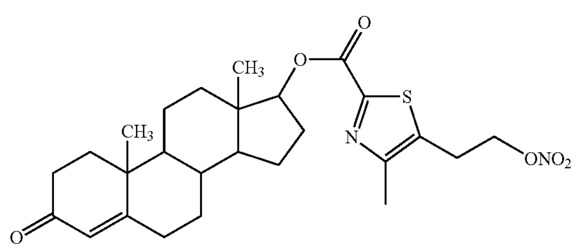 |
| Pet-167  | 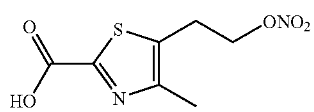 |
| Pet-168  | 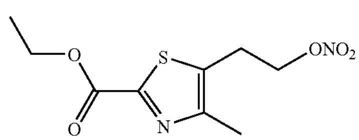 |
| Pet-169  | 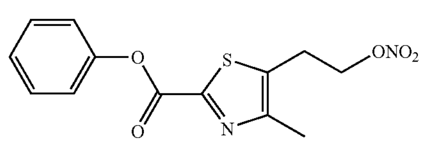 |
| Pet-170  | 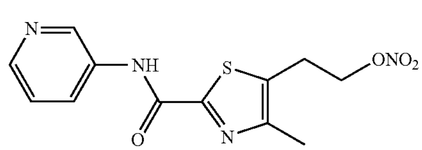 |

TABLE 1-continued

| Compound | Chemical Structure |
|---|---|
| Pet-171 | 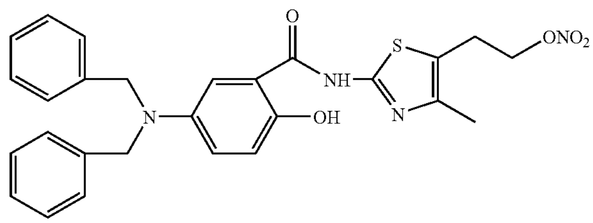 |
| Pet-172 | 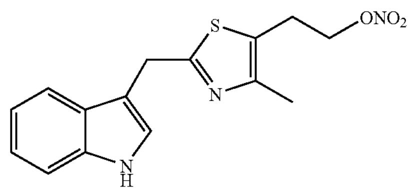 |
| Pet-173 | 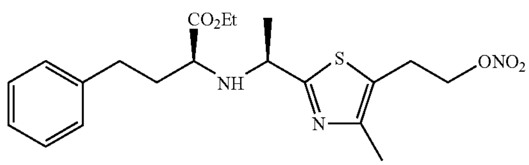 |
| Pet-174 | 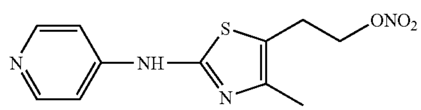 |
| Pet-175 | 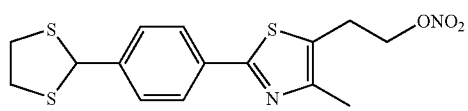 |
| Pet-176 | 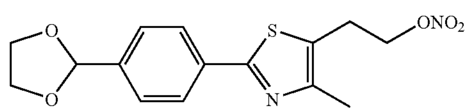 |
| Pet-177 | 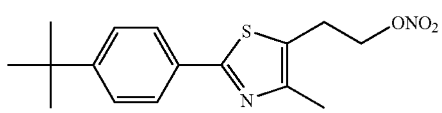 |
| Pet-178 | 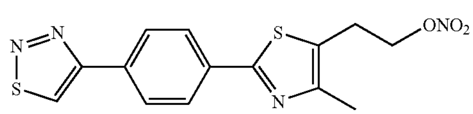 |
| Pet-179 | 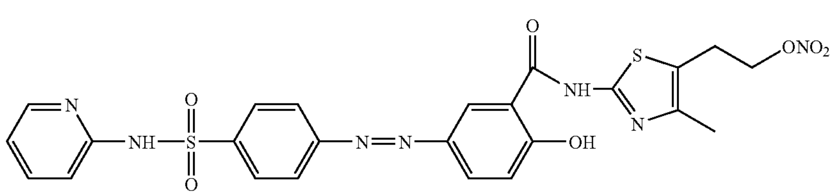 |
| Pet-180 | 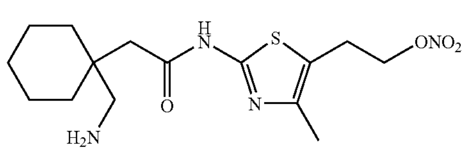 |

TABLE 1-continued

| Compound | Chemical Structure |
|---|---|
| Pet-181 | 2-(3,5-difluorophenyl)-4-methyl-5-(2-nitrooxyethyl)thiazole |
| Pet-182 | 2-(5-chloro-2-methoxyphenyl)-4-methyl-5-(2-nitrooxyethyl)thiazole |
| Pet-183 | 2-guanidino-4-methyl-5-(2-nitrooxyethyl)thiazole |
| Pet-184 | 2-[2-(2-chlorobenzylidene)hydrazinyl]-4-methyl-5-(2-nitrooxyethyl)thiazole |
| Pet-185 | 2-(4-chlorophenylamino)-4-methyl-5-(2-nitrooxyethyl)thiazole |
| Pet-186 | 2-(3,5-dichlorophenylamino)-4-methyl-5-(2-nitrooxyethyl)thiazole |

TABLE 2

| Compound | Chemical Name |
|---|---|
| Pet-2 | 2-Ethyl-4-methyl-5-(2-nitrooxy-ethyl)-thiazole |
| Pet-3 | 2,4-Dimethyl-5-(2-nitrooxy-ethyl)-thiazole |
| Pet-4 | 2-Isopropyl-4-methyl-5-(2-nitrooxy-ethyl)-thiazole |
| Pet-5 | 4-Methyl-5-(-2-nitrooxy-ethyl)-2-(1-nitrooxy-ethyl-thiazole |
| Pet-6 | 4-Methyl-5-(nitrooxy-ethyl)-2-trifluoromethyl-thiazole |
| Pet-7 | Dimethyl-[4-methyl-5-(2-nitrooxy-ethyl)-thiazol-2-yl]-amine |
| Pet-8 | 4-Methyl-5-(2-nitrooxy-ethyl)-2-phenyl-thiazole |
| Pet-9 | 2-Methoxy-4-methyl-5-(2-nitrooxy-ethyl)-thiazole |
| Pet-10 | 4-methyl-5-(2-nitrooxy-ethyl)-thiazole-2-ylamine |
| Pet-11 | 4-[4-Methyl-5-(2-nitrooxy-ethyl)thiazole-2-yl]-piperidine |
| Pet-12 | 3-[4-Methyl-5-(2-nitrooxy-ethyl)-thiazole-2-yl]-pyridine |
| Pet-13 | 1,4-Bis-[4-Methyl-5-(2-nitrooxy)-ethyl)-thiazol-2-yl]-Butane |
| Pet-14 | 2-Benzyloxy-4-methyl-5-(2-nitrooxy-ethyl)-thiazole |
| Pet-15 | 1,2-Bis-[4-methyl-5-(2-nitrooxy)-ethyl)-thiazol-2-yl]-ethane |
| Pet-16 | Bis-[4-Methyl-5-(2-nitrooxy)-ethyl)-thiazol-2-yl]-methane |
| Pet-17 | 2-[1-(6-Methoxy-naphthalen-2-yl-ethyl]-4-methyl-5-(2-nitrooxy-ethyl)-thiazole |

TABLE 2-continued

| Compound | Chemical Name |
|---|---|
| Pet-18 | 2-Chloro-3-[4-methyl-5-(2-nitrooxy-ethyl)-thiazol-2-yl]-6-trifluoromethyl-pyridine |
| Pet-19 | Diethyl-{3-[4-methyl-5-(2-nitrooxy-ethyl)-thiazol-2-yl]-pyridin-4-yl}-amine |
| Pet-20 | 2-Methyl-5-[4-methyl-5-(2-nitrooxy-ethyl)-thiazol-2-yl]-pyridine |
| Pet-21 | 3-[4-Methyl-5-(2-nitrooxy-ethyl)-thiazol-2-yl]-pyridine 1-oxide |
| Pet-22 | 5-[4-Methyl-5-(2-nitrooxy-ethyl)-thiazol-2-yl]-2-trifluoromethyl-pyridine |
| Pet-23 | 2-Methoxy-6-[4-methyl-5-(2-nitrooxy-ethyl)-thiazol-2-yl]-pyrazine |
| Pet-24 | Methyl-{6-[4-methyl-5-(2-nitrooxy-ethyl)-thiazol-2-yl]-pyrazin-2-yl}-amine |
| Pet-25 | 2-Ethyl-4-[4-methyl-5-(2-nitrooxy-ethyl)-thiazol-2-yl]-pyridine 1-oxide |
| Pet-26 | 5-[4-Methyl-5-(2-nitrooxy-ethyl)-thiazol-2-yl]-2-trifluoromethyl-pyridine 1-oxide |
| Pet-27 | 2-(2,3-Dichloro-phenyl)-4-methyl-5-(2-nitrooxy-ethyl)-thiazole |
| Pet-28 | 2-(2,4-Dichloro-phenyl)-4-methyl-5-(2-nitrooxy-ethyl)-thiazole |
| Pet-29 | 2-(2,6-Dichloro-phenyl)-4-methyl-5-(2-nitrooxy-ethyl)-thiazole |
| Pet-30 | 2-(3,4-Dichloro-phenyl)-4-methyl-5-(2-nitrooxy-ethyl)-thiazole |
| Pet-31 | 2-(3,5-Dichloro-phenyl)-4-methyl-5-(2-nitrooxy-ethyl)-thiazole |
| Pet-32 | 2-(2,3-Difluoro-4-methyl-phenyl)-4-methyl-5-(2-nitrooxy-ethyl)-thiazole |
| Pet-33 | 2-(2,6-Difluoro-3-methyl-phenyl)-4-methyl-5-(2-nitrooxy-ethyl)-thiazole |
| Pet-34 | 2-(2,3-Dimethyl-phenyl)-4-methyl-5-(2-nitrooxy-ethyl)-thiazole |
| Pet-35 | 2-(3,4-Dimethyl-phenyl)-4-methyl-5-(2-nitrooxy-ethyl)-thiazole |
| Pet-36 | 2-(2,4-Dichloro-5-fluoro-phenyl)-4-methyl-5-(2-nitrooxy-ethyl)-thiazole |
| Pet-37 | 2-(2-Fluoro-phenyl)-4-methyl-5-(2-nitrooxy-ethyl)-thiazole |
| Pet-38 | 2-(4-Fluoro-2-methyl-phenyl)-4-methyl-5-(2-nitrooxy-ethyl)-thiazole |
| Pet-39 | 2-(2-Fluoro-3-trifluoromethyl-phenyl)-4-methyl-5-(2-nitrooxy-ethyl)-thiazole |
| Pet-40 | 2-(4-Fluoro-2-trifluoromethyl-phenyl)-4-methyl-5-(2-nitrooxy-ethyl)-thiazole |
| Pet-41 | 2-(3-Fluoro-4-trifluoromethyl-phenyl)-4-methyl-5-(2-nitrooxy-ethyl)-thiazole |
| Pet-42 | N,N'-Bis-[4-methyl-5-(2-nitrooxy-ethyl)-thiazol-2-yl]-hydrazine |
| Pet-43 | Bis-[4-methyl-5-(2-nitrooxy-ethyl)-thiazol-2-yl]-amine |
| Pet-44 | 4-Methyl-5-(2-nitrooxy-ethyl)-2-pentafluorophenyl-thiazole |
| Pet-45 | 4-Methyl-5-(2-nitrooxy-ethyl)-2-pentafluoroethyl-thiazole |
| Pet-46 | 4-Methyl-5-(2-nitrooxy-ethyl)-2-(2-phenyl-propyl)-thiazole |
| Pet-47 | Hexyl-[4-methyl-5-(2-nitrooxy-ethyl)-thiazol-2-yl]-amine |
| Pet-48 | N-[4-Methyl-5-(2-nitrooxy-ethyl)-thiazol-2-yl]-N'-phenyl-hydrazine |
| Pet-49 | 3-Methyl-1-[4-methyl-5-(2-nitrooxy-ethyl)-thiazol-2-yl]-butylamine |
| Pet-50 | N-[4-Methyl-5-(2-nitrooxy-ethyl)-thiazol-2-yl]-hydroxylamine |
| Pet-51 | C-[4-Methyl-5-(2-nitrooxy-ethyl)-thiazol-2-yl]-methylamine |
| Pet-52 | N-[4-Methyl-5-(2-nitrooxy-ethyl)-thiazol-2-yl]-formamide |
| Pet-53 | Formic acid N'-[4-methyl-5-(2-nitrooxy-ethyl)-thiazol-2-yl]-hydrazide |
| Pet-54 | Bis-[4-methyl-5-(2-nitrooxy-ethyl)-thiazol-2-yl]-disulfide |
| Pet-55 | 4-Methyl-5-(2-nitrooxy-ethyl)-2-(2,3,4,5-tetrafluoro-phenyl)-thiazole |
| Pet-56 | 2-(4-Chloro-phenyl)-4-methyl-5-(2-nitrooxy-ethyl)-thiazole |
| Pet-57 | 5-[4-Methyl-5-(2-nitrooxy-ethyl)-thiazol-2-yl]-benzene-1,2,3-triol |
| Pet-58 | 4-Methyl-5-(2-nitrooxy-ethyl)-2-(2,4,6-trimethyl-phenyl)-thiazole |
| Pet-59 | 4-Methyl-5-(2-nitrooxy-ethyl)-2-(4-trifluoromethyl-phenyl)-thiazole |
| Pet-60 | 4-Methyl-5-(2-nitrooxy-ethyl)-2-(3-trifluoromethyl-phenyl)-thiazole |
| Pet-61 | 4-Methyl-5-(2-nitrooxy-ethyl)-2-(2-trifluoromethyl-phenyl)-thiazole |
| Pet-62 | 4-Methyl-5-(2-nitrooxy-ethyl)-2-(2-trifluoromethoxy-phenyl)-thiazole |
| Pet-63 | 4-Methyl-5-(2-nitrooxy-ethyl)-2-(4-trifluoromethoxy-phenyl)-thiazole |
| Pet-64 | 4-Methyl-5-(2-nitrooxy-ethyl)-2-p-tolyl-thiazole |
| Pet-65 | 4-Methyl-5-(2-nitrooxy-ethyl)-2-m-tolyl-thiazole |
| Pet-66 | 2-[1-(4-Isobutyl-phenyl)-ethyl]-4-methyl-5-(2-nitrooxy-ethyl)-thiazole |
| Pet-67 | 2-(4-[1,2]Dithiolan-3-yl-butyl)-4-methyl-5-(2-nitrooxy-ethyl)-thiazole |
| Pet-68 | 3-(4-Amino-2-methyl-pyrimidin-5-ylmethyl)-4-methyl-5-(2-nitrooxy-ethyl)-thiazol-3-ium; chloride |
| Pet-69 | 2-Furan-2-yl-4-methyl-5-(2-nitrooxy-ethyl)-thiazole |
| Pet-70 | [4-Methyl-5-(2-nitrooxy-ethyl)-thiazol-2-yl]-hydrazine |
| Pet-71 | 4-Methyl-5-(2-nitrooxy-ethyl)-2-thiophen-2-yl-thiazole |
| Pet-72 | 2-Benzo[b]thiophen-2-yl-4-methyl-5-(2-nitrooxy-ethyl)-thiazole |
| Pet-73 | 4-Methyl-5-(2-nitrooxy-ethyl)-2-(2,2,5,5-tetramethyl-pyrrolidin-3-yl)-thiazole |
| Pet-74 | 4-Methyl-5-(2-nitrooxy-ethyl)-2-(2,2,5,5-tetramethyl-2,5-dihydro-1H-pyrrol-3-yl)-thiazole |
| Pet-75 | 2,2,5,5-Tetramethyl-3-[4-methyl-5-(2-nitrooxy-ethyl)-thiazol-2-yl]-2,5-dihydro-pyrrol-1-ol |
| Pet-76 | 2-Cyano-N-[4-methyl-5-(2-nitrooxy-ethyl)-thiazol-2-yl]-acetamide |
| Pet-77 | 4-Methyl-5-(2-nitrooxy-ethyl)-2-pyrrolidin-2-yl-thiazole |
| Pet-78 | [4-Methyl-5-(2-nitrooxy-ethyl)-thiazol-2-yl]-phenyl-amine |
| Pet-79 | N-[4-Methyl-5-(2-nitrooxy-ethyl)-thiazol-2-ylmethyl]-acetamide |
| Pet-80 | [4-Methyl-5-(2-nitrooxy-ethyl)-thiazol-2-yl]-pyridin-3-ylmethyl-amine |
| Pet-81 | 4-[4-Methyl-5-(2-nitrooxy-ethyl)-thiazol-2-yl]-pyridine |
| Pet-82 | 3-[4-Methyl-5-(2-nitrooxy-ethyl)-thiazol-2-yl]-piperidine |
| Pet-83 | 2-(3,5-Dimethyl-pyrazol-1-yl)-4-methyl-5-(2-nitrooxy-ethyl)-thiazole |
| Pet-84 | 5-[4-Methyl-5-(2-nitrooxy-ethyl)-thiazol-2-yl]-1H-imidazol-4-ylamine |
| Pet-85 | 4-Methyl-5-(2-nitrooxy-ethyl)-2-vinyl-thiazole |
| Pet-86 | 4-Methyl-5-(2-nitrooxy-ethyl)-2-thiophen-2-ylmethyl-thiazole |
| Pet-87 | 4-Methyl-5-(2-nitrooxy-ethyl)-2-(1-thiophen-2-yl-ethyl)-thiazole |
| Pet-88 | [4-Methyl-5-(2-nitrooxy-ethyl)-thiazol-2-yl]-thiophen-2-yl-methanone |
| Pet-89 | 4-Methyl-5-(2-nitrooxymethoxy-ethyl)-thiazole |
| Pet-90 | 2,4-Dimethyl-5-(2-nitrooxymethoxy-ethyl)-thiazole |
| Pet-91 | [2-(2-Ethyl-4-methyl-thiazol-5-yl)-ethyl]-nitrooxymethyl-amine |
| Pet-92 | 2-Isopropyl-4-methyl-5-(2-nitrooxymethylsulfanyl-ethyl)-thiazole |
| Pet-93 | 4-Methyl-5-(2-nitrooxy-ethyl)-2-(4-nitrooxy-pyrrolidin-2-yl)-thiazole |
| Pet-94 | Diethyl-[4-methyl-5-(2-nitrooxy-ethyl)-thiazol-2-yl]-amine |

TABLE 2-continued

| Compound | Chemical Name |
|---|---|
| Pet-95 | 4-Methyl-5-(2-nitrooxy-ethyl)-2-(nitrooxy-thiophen-2-yl-methyl)-thiazole |
| Pet-96 | N-[4-Methyl-5-(2-nitrooxy-ethyl)-thiazol-2-yl]-2-nitrooxy-acetamide |
| Pet-97 | N-[4-Methyl-5-(2-nitrooxy-ethyl)-thiazol-2-yl]-acetamide |
| Pet-98 | N-[4-Methyl-5-(2-nitrooxy-ethyl)-thiazol-2-ylmethyl]-acetamide |
| Pet-99 | 4'-Methyl-5'-(2-nitrooxy-ethyl)-2,3,4,5-tetrahydro-[2,2']bithiazolyl |
| Pet-100 | 2-Cyclopropyl-4-methyl-5-(2-nitrooxy-ethyl)-thiazole |
| Pet-101 | 2-Cyclohexyl-4-methyl-5-(2-nitrooxy-ethyl)-thiazole |
| Pet-102 | Bis-[4-methyl-5-(2-nitrooxy-ethyl)-thiazole-2-yl]-diazene |
| Pet-103 | 2-Amino-3-[4-methyl-5-(2-nitrooxy-ethyl)-thiazol-2-yl]-propionic acid |
| Pet-104 | 2-[4-Methyl-5-(2-nitrooxy-ethyl)-thiazol-2-yl]-phenylamine |
| Pet-105 | N-{2-[4-Methyl-5-(2-nitrooxy-ethyl)-thiazol-2-yl]-phenyl}-acetamide |
| Pet-106 | 4-[4-Methyl-5-(2-nitrooxy-ethyl)-thiazol-2-yl]-phenylamine |
| Pet-107 | N-{4-[4-Methyl-5-(2-nitrooxy-ethyl)-thiazol-2-yl]-phenyl}-acetamide |
| Pet-108 | 2-Isobutyl-4-methyl-5-(2-nitrooxy-ethyl)-thiazole |
| Pet-109 | Diisopropyl-[4-methyl-5-(2-nitrooxy-ethyl)-thiazol-2-yl]-amine |
| Pet-110 | 2,2,5,5-Tetramethyl-3-[4-methyl-5-(2-nitrooxy-ethyl)-thiazol-2-yl]-2,5-dihydro-pyrrol-1-ol (free radical) |
| Pet-111 | Dibutyl-[4-methyl-5-(2-nitrooxy-ethyl)-thiazol-2-yl]-amine |
| Pet-112 | Amino-{3-[4-methyl-5-(2-nitrooxy-ethyl)-thiazol-2-yl]-propylamino}-acetic acid |
| Pet-113 | 4-Methyl-5-(2-nitrooxy-ethyl)-thiazole-2-carboxylic acid ethyl ester |
| Pet-114 | [4-Methyl-5-(2-nitrooxy-ethyl)-thiazol-2-yl]-acetonitrile |
| Pet-115 | 4,4'-Bis-[4-methyl-5-(2-nitrooxy-ethyl)-thiazole-2-yl]-diphenyl-disulfide |
| Pet-116 | Acetic acid 2-[4-methyl-5-(2-nitrooxy-ethyl)-thiazol-2-yl]-phenyl ester |
| Pet-117 | 2-[4-Methyl-5-(2-nitrooxy-ethyl)-thiazol-2-yl]-phenol |
| Pet-118 | 4,4'-Dimethyl-5,5'-bis-(2-nitrooxy-ethyl)-[2,2']bithiazolyl |
| Pet-119 | 1-[4-Methyl-5-(2-nitrooxy-ethyl)-thiazol-2-yl]-2-phenyl-ethylamine |
| Pet-120 | 4-Methyl-5-(2-nitrooxy-ethyl)-2-(4-nitro-phenyl)-thiazole |
| Pet-121 | 2-(4-Ethoxy-phenyl)-4-methyl-5-(2-nitrooxy-ethyl)-thiazole |
| Pet-122 | Diethyl-{4-[4-methyl-5-(2-nitrooxy-ethyl)-thiazol-2-yl]-phenyl}-amine |
| Pet-123 | Dimethyl-{4-[4-methyl-5-(2-nitrooxy-ethyl)-thiazol-2-yl]-phenyl}-amine |
| Pet-124 | 1-Methyl-4-[4-methyl-5-(2-nitrooxy-ethyl)-thiazol-2-yl]-piperidine |
| Pet-125 | 2-[4-Methyl-5-(2-nitrooxy-ethyl)-thiazol-2-yl]-pyrazine |
| Pet-126 | 2-[4-Methyl-5-(2-nitrooxy-ethyl)-thiazol-2-yl]-pyrazine 4-oxide |
| Pet-127 | 2-[4-Methyl-5-(2-nitrooxy-ethyl)-thiazol-2-yl]-pyrazine 1,4-dioxide |
| Pet-128 | 4-Methyl-2-naphthalen-1-yl-5-(2-nitrooxy-ethyl)-thiazole |
| Pet-129 | 2-(2-Chloro-6-methyl-phenyl)-4-methyl-5-(2-nitrooxy-ethyl)-thiazole |
| Pet-130 | 2-(2-Chloro-6-fluoro-phenyl)-4-methyl-5-(2-nitrooxy-ethyl)-thiazole |
| Pet-131 | 2-(2-Chloro-4-fluoro-phenyl)-4-methyl-5-(2-nitrooxy-ethyl)-thiazole |
| Pet-132 | 2-(2-Chloro-5-fluoro-phenyl)-4-methyl-5-(2-nitrooxy-ethyl)-thiazole |
| Pet-133 | 2-(4-Chloro-2-fluoro-phenyl)-4-methyl-5-(2-nitrooxy-ethyl)-thiazole |
| Pet-134 | 2-(3-Chloro-4-fluoro-phenyl)-4-methyl-5-(2-nitrooxy-ethyl)-thiazole |
| Pet-135 | 2-Benzo[1,3]dioxol-5-ylmethyl-4-methyl-5-(2-nitrooxy-ethyl)-thiazole |
| Pet-136 | {2-Benzo[1,3]dioxol-5-yl-1-[4-methyl-5-(2-nitrooxy-ethyl)-thiazol-2-yl]-ethyl}-methyl-amine |
| Pet-137 | 2,2,4-Trimethyl-6-[4-methyl-5-(2-nitrooxy-ethyl)-thiazol-2-yl]-1,2,3,4-tetrahydro-quinoline |
| Pet-138 | 2,2,4-Trimethyl-6-[4-methyl-5-(2-nitrooxy-ethyl)-thiazol-2-yl]-3,4-dihydro-2H-quinolin-1-oxide |
| Pet-139 | trans-2-{4-[2-(3,5-Dimethoxy-phenyl)-vinyl]-phenyl}-4-methyl-5-(2-nitrooxy-ethyl)-thiazole |
| Pet-140 | 4-{4-[4-Methyl-5-(2-nitrooxy-ethyl)-thiazol-2-yl]-butyl}-tetrahydro-thieno[3,4-d]imidazol-2-one |
| Pet-141 | (4-{1-[4-Methyl-5-(2-nitrooxy-ethyl)-2-yl]-ethyl}-phenyl)-phenyl-methanone |
| Pet-142 | 2-[1-(2-Fluoro-biphenyl-4-yl0-ethyl-4-methyl-5-(2-nitrooxy-ethyl)-thiazole |
| Pet-143 | (2,6-Dichloro-phenyl)-{2-nitrooxy-ethyl)-thiazol-2-ylmethyl]-phenyl}-amine |
| Pet-144 | 2-Ethyl-5-[4-methyl-5-(2-nitrooxy-ethyl)-thiazol-2-yl]-pyridine |
| Pet-145 | (2-Fluoro-phenyl)-[4-methyl-5-(2-nitrooxy-ethyl)-thiazol-2-yl]-amine |
| Pet-146 | (5-Fluoro-2-methyl-phenyl)-[4-methyl-5-(2-nitrooxy-ethyl)-thiazol-2-yl]-amine |
| Pet-147 | Ethyl-[4-methyl-5-(2-nitrooxy-ethyl)-thiazol-2-yl]-amine |
| Pet-148 | (3,5-Bis-trifluoromethyl-phenyl)-[4-methyl-5-(2-nitrooxy-ethyl)-thiazol-2-yl]-amine |
| Pet-149 | [4-Methyl-5-(2-nitrooxy-ethyl)-thiazol-2-yl]-naphthalen-1-yl-amine |
| Pet-150 | 2-(6-Methoxy-naphthalen-2-yl)-N-[4-methyl-5-(2-nitrooxy-ethyl)-thiazol-2-yl]-propionamide |
| Pet-151 | 5-[1,2]Dithiolan-3-yl-pentanoic acid [4-methyl-5-(2-nitrooxy-ethyl)-thiazol-2-yl]-amide |
| Pet-152 | 2-(4-Isobutyl-phenyl)-N-[4-methyl-5-(2-nitrooxy-ethyl)-thiazol-2-yl]-propionamide |
| Pet-153 | 4-Methyl-5-(2-nitrooxy-ethyl)-thiazole-2-carboxylic acid N'-phthalazin-1-yl-hydrazide |
| Pet-154 | N-[4-methyl-5-(2-nitrooxy-ethyl)-thiazol-2-yl]-nicotinamide |
| Pet-155 | allyl-[4-methyl-5-(2-nitrooxy-ethyl)-thiazol-2-yl]-amine |
| Pet-156 | N-[4-methyl-5-(2-nitrooxy-ethyl)-thiazol-2-yl]-1-oxy-nicotinamide |
| Pet-157 | 4-acetylamino-N-[4-methyl-5-(2-nitrooxy-ethyl)-thiazol-2-yl]-benzamide |
| Pet-158 | hexadecanoic acid [4-methyl-5-(2-nitrooxy-ethyl)-thiazol-2-yl]-amide |
| Pet-159 | acetic acid 2-[4-methyl-5-(2-nitrooxy-ethyl)-thiazol-2-ylcarbamoyl]-phenyl ester |
| Pet-160 | pyrrolidine-2-carboxylic acid [4-methyl-5-(2-nitrooxy-ethyl)-thiazol-2-yl]-amide |
| Pet-161 | 2,6-difluoro-N-[4-methyl-5-(2-nitrooxy-ethyl)-thiazol-2-yl]-benzamide |
| Pet-162 | 2-(2,4-dichloro-phenyl)-N-[4-methyl-5-(2-nitrooxy-ethyl)-thiazol-2-yl]-acetamide |
| Pet-163 | 2-(2,4-dichloro-phenoxy)-N-[4-methyl-5-(2-nitrooxy-ethyl)-thiazol-2-yl]-acetamide |
| Pet-164 | 4-methyl-5-(2-nitrooxy-ethyl)-thiazole-2-carboxylic acid 10,13-dimethyl-3-oxo-2,3,6,7,8,9,10,11,12,13,14,15,16,17-tetradecahydro-1H-cyclopenta[a]phenanthren-17-yl ester |
| Pet-165 | 1-[4-Methyl-5-(2-nitrooxy-ethyl)thiazol-2-ylmethyl]-pyrrolidin-2-one |
| Pet-166 | 2-Propyl-pentanoic acid [4-methyl-5-(2-nitrooxy-ethyl)-thiazol-2-yl]-amide |
| Pet-167 | 4-Methyl-5-(2-nitrooxy-ethyl)-thiazole-2-carboxylic acid |
| Pet-168 | 4-Methyl-5-(2-nitrooxy-ethyl)-thiazole-2-carboxylic acid ethyl ester |
| Pet-169 | 4-Methyl-5-(2-nitrooxy-ethyl)-thiazole-2-carboxylic acid phenyl ester |
| Pet-170 | 4-Methyl-5-(2-nitrooxy-ethyl)-thiazole-2-carboxylic acid pyridin-3-ylamide |

TABLE 2-continued

| Compound | Chemical Name |
|---|---|
| Pet-171 | 5-Dibenzylamino-2-hydroxy-N-[4-methyl-5-(-2-nitrooxy-ethyl)-thiazol-2-yl]-benzamide |
| Pet-172 | 3-[4-Methyl-5-(2-nitrooxy-ethyl)thiazol-2-ylmethyl]-1H-indole |
| Pet-173 | 2-{1-[4-Methyl-5-(2-nitrooxy-ethyl)-thiazol-2-yl]-ethylamino}-4-phenyl-butyric acid ethyl ester |
| Pet-174 | [4-Methyl-5-(2-nitrooxy-ethyl)-2-yl]-pyridin-4-yl-amine |
| Pet-175 | 2-(4-[1,3]Dithiolan-2-yl-phenyl)-4-methyl-5-(2-nitrooxy-ethyl)-thiazole |
| Pet-176 | 2-(4-[1,3]Dioxolan-2-yl-phenyl)-4-methyl-5-(2-nitrooxy-ethyl)-thiazole |
| Pet-177 | 2-(4-tert-Butyl-phenyl)-4-methyl-5-(2-nitrooxy-ethyl)-thiazole |
| Pet-178 | 4-{4-[4-Methyl-5-(2-nitrooxy-ethyl)-thiazol-2-yl]-phenyl}-[1,2,3]thiadiazole |
| Pet-179 | 2-Hydroxy-N-[4-methyl-5-(2-nitrooxy-ethyl)-thiazole-2-yl]-5-[4-(pyridine-2-ylsulfamoyl)-phenylazo]-benzamide |
| Pet-180 | 2-(1-Aminomethyl-cyclohexyl)-N-[4-methyl-5-(2-nitrooxy-ethyl)-thiazol-2-yl]-acetamide |
| Pet-181 | 2-(3,5-difluoro-phenyl)-4-methyl-5-(2-nitrooxy-ethyl)-thiazole |
| Pet-182 | 2-(5-chloro-2-methoxy-phenyl)-4-methyl-5-(2-nitrooxy-ethyl)-thiazole |
| Pet-183 | N-[4-methyl-5-(2-nitrooxy-ethyl)-thiazol-2-yl]-guanidine |
| Pet-184 | N-(2-chloro-benzylidene)-N'-[4-methyl-5-(nitrooxy-ethyl)-thiazol-2-yl]-hydrazine |
| Pet-185 | (4-chlorophenyl)-[4-methyl-5-(2-nitrooxy-ethyl)-thiazol-2-yl]-amine |
| Pet-186 | (3,5-dichloro-phenyl)-[4-methyl-5-(2-nitrooxy-ethyl)-thiazol-2-yl]-amine |

In Vitro Studies

Experimental Methods:

In Vitro Vasorelaxation:

In order to measure the vasorelaxation effect in vitro, two parameters were followed in the assays: the mechanical contraction and relaxation of aortae tissue before and during dose response exposure of aortae tissues to the compounds of the present invention as well as to the control compound GTN, and the quantitative levels of c-GMP before and after exposing aortae tissues to the compounds of the present invention as well as to the control compound GTN.

Male Sprague Dawley rats were anaesthetized using intraperitoneal injection of ketamine and xylazine (50 and 10 milligram per kilogram, respectively) and the thoracic aorta, the large upper portion of the descending aorta, starting at the caudal border of the chest bone, was removed thereafter, while carefully removing the paraadventetial tissue surrounding the vessel. Aortae were cut into rings of 4-5 millimeters and mounted onto the tissue path. The path buffer (Krebs-bicrbonate) was constantly gassed with carbogen and maintained at 37° C. The rings were preloaded under 2 g tension and equilibrated for 90 minutes, while refreshing the buffer every 15 minutes. After stabilization, the rings were contracted with epinephrine (1 μM). Cumulative Concentration-Response Curves (CCRC) were measured for the vasorelaxing effect induced by adding various concentrations, ranging from $10^{-10}$ M to $10^{-5}$ M of Pet-2, Pet-3, Pet-7, Pet-8, Pet-12, Pet-24, Pet-43, Pet-59, Pet-147, Pet-152 and Pet-154, and glyceryltrinitrate (GTN), according to the procedure described in Feelich et al., *Molecular Pharmacology*, 56:243-253 (1999) The vehicle, which was used for this experiment was water:ethanol:propyleneglycol at proportional ratio of 1:1:1.

In Vitro Induction of Tolerance to NO Releasing Compounds:

Aortic rings were prepared as described hereinabove, and were exposed to 0.44 mM GTN (vehicle was water:ethanol:propyleneglycol at proportional ratio of 1:1:1) for 1 hour before CCRC construction, to thereby induce tolerance to nitroglycerine. At the end of the tolerance induction period, rings were thrice washed with the path buffer (Krebs-bicrbonate) every 15 minutes for the following hour and then CCRC for vasorelaxation on GTN-induced tolerance rings were constructed for GTN (pretreated versus untreated rings, FIG. 15), in order to verify the ability to induce and measure GTN tolerance induction in vitro Attempted induction of tolerance to the NO-donating compounds of the present invention was performed under the same conditions as for GTN. Thus, in an exemplary experiment, rings were exposed to 0.44 mM solution of Pet-3 in the attempt to induce tolerance for Pet-3. CCRC were then measured for the vasorelaxing effect of Pet-3 on a group of rings which were pre-exposed to Pet-3 as to induce tolerance to Pet-3, and for an untreated control group. The above protocol was repeated with Pet-2, Pet-7, Pet-8, Pet-12, Pet-24, Pet-43, Pet-149 and Pet-152.

Cross-tolerance studies were conducted using the same technique described above for measuring vasorelaxation of aortic rings from rats. Two groups of aortic rings samples were pre-treated with GTN, then one group was measured for vasorelaxation by GTN and the second group for vasorelaxation by Pet-12, an exemplary NO-donor according to the present invention. For the opposite cross-tolerance studies, two groups of aortic rings samples were pre-treated with Pet-12, then one group was measured for vasorelaxation by GTN and the second group for vasorelaxation by Pet-12.

Cyclic-GMP Measurement in Aortic Rat Tissue:

To determine the c-GMP-producing effect of some exemplary NO-donors according to the present invention, as compared with that of GTN, rings were treated as described above in the vasorelaxation effect studies except that they were not hooked to the transducer. GTN ($10^{-6}$ M) was added to the chamber and, 1 minute after exposure to the drug, rings (usually 3-5) were taken, wrapped with aluminum foil and immediately frozen in liquid nitrogen for storage. Control sample group was treated with the vehicle solution only. At the time of analysis, rings were thawed, blotted over a dry gauzed and weighted. A known weight of tissue was homogenized in 2 ml ice-cold modified Hank's balanced salt solution containing (in gram/liter) NaCl 8; KCl 0.4; glucose 1; $KH_2PO_4$ 0.06; $Na_2HPO_4$ 0.047; Phenol red 0.017 and further containing 25 mM EDTA (disodium salt). The homogenate was centrifuged at 4000 g (force units) for 10 minutes at 2-4° C. and the supernatant was thereafter transferred into fresh pre-cooled test tube containing 1 ml of acetonitrile. The tubes were vortex mixed for a few seconds and subsequently centrifuged at 4000 g for 5 minutes at 2-4° C., to remove the precipitated protein. Each supernatant was transferred into a clean test tube and evaporated to dryness under a stream of nitrogen at 55° C. The dry residue was reconstituted with 10 volumes of Tris-EDTA buffer pH 7.5 (0.05 M Tris containing 4 mM EDTA). Aliquots of 100 μl of the reconstituted solution in duplicate were used for c-GMP measurements using Amersham RIA kit, as is described in Haj-Yehia & Benet [*Pharmacology*, 1995, 273, 1, pp. 94-100]. Standard curves were plotted with six concentrations (0, 0.5, 1, 2, 4 and 8 pmoles of c-GMP per tube).

Experimental Results:

In Vitro Vasorelaxation:

The vasorelaxing effect of the thiazole-derived NO-donors according to the present invention was measured on slices of thoracic aorta of rats contracted with epinephrine, as described hereinabove.

The obtained results for Pet-2, Pet-3, Pet-7, Pet-8, Pet-12, Pet-24, Pet-43, Pet-59, Pet-147, Pet-152 and Pet-154 are presented in FIGS. 2-14, and are summarized in Table 3 below. The results clearly show that the thiazole-based NO-donors according to a preferred embodiment of the present invention are highly active in inducing a vasorelaxation effect and are highly superior in this respect to GTN, being 10-fold more active than GTN in exemplary cases.

TABLE 3

| Compound | Concentration | $EC_{50}$ | FIG. No. |
|---|---|---|---|
| GTN | 4.47E−08 | −7.55 | 3 to 6 and 8 to 14 |
| Pet-2 | 2.51E−08 | −7.6 | 2 and 3 |
| Pet-3 | 3.55E−08 | −7.45 | 4 |
| Pet-7 | 2.82E−08 | −7.55 | 5 |
| Pet-8 | 2.82E−08 | −7.7 | 6 |
| Pet-12 | 3.98E−08 | −7.4 | 7 |
| Pet-24 | 2.00E−07 | −6.7 | 8 |
| Pet-43 | 1.59E−07 | −6.8 | 9 |
| Pet-59 | 7.94E−08 | −7.1 | 10 |
| Pet-147 | 3.16E−08 | −7.5 | 11 |
| Pet-152 | 5.01E−08 | −7.3 | 12 |
| Pet-154 | 3.98E−08 | −7.4 | 13 |

In Vitro Induction of Tolerance to NO Releasing Compounds:

The absence of tolerance induction by the thiazole-based NO-donors according to the present invention was demonstrated by pre-exposing slices of thoracic aorta of rats to the test compounds followed by vasorelaxation measurements as described hereinabove.

The obtained results for Pet-2, Pet-3, Pet-7, Pet-8, Pet-12, Pet-24, Pet-43, Pet-149 and Pet-152 are presented Table 4 below and are further shown in FIGS. 15-23. These results clearly demonstrate that the NO-donors of the present invention do not induce tolerance and are thus highly superior to GTN.

The results obtained in the cross-tolerance studies described above are presented in FIGS. 19 and 20 and clearly show that the induced tolerance effect to GTN has no effect on the vasorelaxation capacity of Pet-12, an exemplary NO-donor according to the present invention (FIG. 19), and that Pet-12 does not evoke tolerance to itself not to GTN. The results obtained in these (FIG. 20).

TABLE 4

| Compound | Concentration | $EC_{50}$ | FIG. No. |
|---|---|---|---|
| GTN | 4.47E−08 | −7.5 | 15 |
| Pet-2 | 3.98E−08 | −7.4 | 3 |
| Pet-3 | 5.01E−08 | −7.3 | 16 |
| Pet-7 | 5.01E−08 | −7.45 | 17 |
| Pet-8 | 2.51E−08 | −7.6 | 6 |
| Pet-12 | 6.31E−08 | −7.2 | 18 to 20 |
| Pet-24 | 2.51E−07 | −6.6 | 21 |
| Pet-43 | 2.51E−07 | −6.6 | 22 |
| Pet-149 | 4.33E−08 | −7.4 | 23 |
| Pet-152 | 5.01E−08 | −7.3 | 33 |
| Pet-154 | 3.98E−08 | −7.4 | 34 |
| Pet-155 | 5.01E−08 | −7.3 | 32 |

Cyclic-GMP Measurement in Aortic Rat Tissue:

The NO-tolerance effect of GTN and NO-donor compounds according to the present invention was measured by following the production of c-GMP in slices of thoracic aorta of rats. Thus, the production of c-GMP was measured as described in the methods section above for the reference NO-donor compound GTN, and for the NO-donors of the present invention Pet-2, Pet-3, Pet-7, Pet-8, Pet-10, Pet-12, Pet-24, Pet-59, Pet-147, Pet-149, Pet-152, Pet-154 and Pet-155.

The results are summarized in Table 5 hereinbelow and clearly show that while the c-GMP level was significantly reduced following a repeated treatment with GTN, it remained almost unchanged following a repeated treatment with each of the tested NO-donors of the present invention, thus the lack of tolerance induction thereby. These obtained results are further presented in FIG. 25, for Pet-3, Pet-7 and Pet-8, FIG. 27 for Pet-24 and Pet-149, and FIG. 33 for Pet-10, Pet-59, Pet-147, Pet-152, Pet-154 and Pet-155, all of which show the increased levels of cGMP when treated with the exemplary NO-donating compound of the present invention, as compared with GTN.

TABLE 5

| | cGMP (pmol/g tissue) | |
|---|---|---|
| Tested Compound | Pre-infusion | Post-infusion |
| GTN | 127 ± 11 | 45 ± 12[¥] |
| Pet-2 | 143 ± 13 | 140 ± 13[§] |
| Pet-3 | 122 ± 14 | 118 ± 10[§] |
| Pet-7 | 120 ± 12 | 123 ± 12[§] |
| Pet-8 | 133 ± 10 | 136 ± 12[§] |
| Pet-12 | 127 ± 11 | 112 ± 12[§] |
| Pet-24 | 115 ± 14 | 112 ± 10[§] |
| Pet-149 | 112 ± 12 | 115 ± 14[§] |

[¥]Significantly different from pre-infusion values and denotes tolerance
[§]Not significantly different from pre-infusion values and denotes the lack of tolerance In Vivo Studies Experimental Methods:

In order to measure the vasorelaxation effect in vivo, two parameters were observed: the mechanical contraction and relaxation of aortae tissue before and during exposure of aortae tissues to the compounds of the present invention as well as to the reference compound GTN, and the quantitative levels of c-GMP before and after exposing aortae tissues to the compounds of the present invention as well as to the reference compound GTN. These techniques were also used to detect tolerance induction by the NO-donors of the present invention and by GTN.

For c-GMP levels and tolerance development, the rat's thoracic aorta was isolated after exposure to the tested compound in vivo, and measured as described above in the in vitro assays.

Hypotensive Effects:

Mean arterial pressure (MAP) was monitored and determined during bolus infusion of Pet-2, Pet-3, Pet-7, Pet-8, Pet-12 and Pet-13. Briefly, polyethylene catheters (PE50) were inserted into the carotid artery and into the jugular vein of anesthetized hypertensive Sprague-Dawley male rats (200-300 grams). A blood pressure recorder was placed within the carotid artery. Phenylephrine (0.1 mg) was then injected and the mean arterial blood pressure (MABP) was monitored continuously until a stable baseline was reached. The hypotensive effects of intravenous (iv) bolus doses (0.1 mg of each tested compound) administered intravenously at the jugular vein in minimal volume of vehicle (0.2 ml per dose) were evaluated. Five minutes were allowed between each dose, during which the maximal decrease in MAP was recorded and a dose-response graph comparing the hypotensive effect of the compounds was constructed.

Induction of in Vivo Nitrate Tolerance:

Male Sprague Dawley rats (220 to 250 grams) were housed under constant temperature and humidity conditions. Light was maintained at a 12/12 light dark cycle. Except for 12 hours before the experiment, when food fasting was initiated, all rats had free access to standard rat pellet diet and tap water. The animals were anesthetized by intraperitoneal injection of ketamine and xylazine combination (50 and 10 milligram per kilogram, respectively). Chronic catheterization of the superior vena cava was performed as described by Boesgaard et al. [*Circ Res.* 1994, 74, 115-120], and two catheters (medical-grade Tygon catheters) with the tips in the right atrium were implanted through a transverse incision at the mid portion of the neck via the left and right external jugular veins. The catheters were filled with normal saline solution containing 1000 IU/ml of heparin and plugged with a metal pin. Catheters were externalized to the back of the neck region and secured by a polyester felt disk.

After implantation, the rats were individually housed until they regained their preoperative weight and appeared healthy (3 to 4 days post-operation). At this time point (day 0), an osmotic mini-pump (Alza Corp., Palo Alto, Calif.) delivering constant volume (10 μl/hour) of vehicle or drug was connected to one of the intravenous catheters.

For inducing tolerance to the tested NO-donor according to the present invention, the animals received 200 μg/hour of the tested compound for 16 hours (short-term-induced tolerance). A similar number of animals were processed by the same surgical procedure and received the vehicle alone (10 μl/hour of a solution consisting of 30% ethanol and 30% propylene glycol in sterile distilled water for injection).

At the end of the infusion periods used for the development of tolerance (16 hour), the rats were anesthetized as described above, the two catheters were externalized and the delivering catheters were disconnected from the mini-pump. The abdomen was opened by midline incision and the thoracic aorta were isolated, washed and cleaned from the surrounding tissues. Strips of the treated aortas were pooled in chambers containing Krebs-Hanseliet buffer (10 ml), and exposed to 1 μM of the tested NO-donor (final concentration) for 120 seconds. The tissues were quickly collected and frozen in liquid nitrogen for cGMP measurement, described hereinabove.

Experimental Results:

Hypotensive Effects:

The results obtained from evaluating the hypotensive effects of Pet-2, Pet-3, Pet-7, Pet-8, Pet-12, Pet-13 and GTN in vivo, are presented in FIGS. 28-31. These results clearly demonstrate the high activity of the compound of the present invention as hypotensive agents. Unlike GTN, in which attenuation in its effect on MAP was observed, the hypotensive effect of the NO-donating compounds of the present invention on MAP was consistent and reproducible following successive administrations of the compounds, thus indicating the prevention of tolerance development by these exemplary compounds.

Induction of in Vivo Nitrate Tolerance:

The in vivo nitrate tolerance was measured, as described hereinabove, for GTN, Pet-2 and Pet-12. The results obtained are presented in FIG. 24, which shows the absence of tolerance effect induced by Pet-2 as compared with GTN, and in FIG. 26, which shows the absence of tolerance effect induced by Pet-12.

As is shown in FIG. 24, upon exposure to GTN, the level of cGMP following a repeated treatment with GTN was decreased, thus indicating tolerance induction, whereby upon exposure to Pet-2, the levels of c-GMP remained substantially unchanged following a repeated treatment with Pet-2. As is shown in FIG. 26, the same lack of tolerance induction was observed with repeated treatment with Pet-12. These results clearly demonstrate that Pet-2 and Pet-12, two exemplary NO-donor compounds according to the present invention, are highly superior to GTN by being a non-tolerance inducing NO-donating compound.

The results presented herein clearly demonstrate that the NO-releasing capacity of the NO-donors according to the present invention, measured as a capacity to include vasorelaxation both in vitro and in vivo, is superior to that of GTN. The results further demonstrate that the NO-donors of the present invention do not induce tolerance both in vitro and in vivo, nor is their capacity to exert vasorelaxation affected by induced tolerance to GTN.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An NO-donating compound having the general formula I:

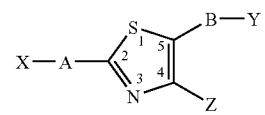

Formula I wherein:

A is absent;

X is a non substituted phenyl;

B is an ethylene chain;

Y is an —ONO$_2$ group; and

Z is methyl, the compound being 4-methyl-5-(2-nitrooxy-ethyl)-2-phenyl-thiazole.

2. A pharmaceutical composition comprising, as an active ingredient, the NO-donating compound of claim 1 and a pharmaceutically acceptable carrier.

3. The pharmaceutical composition of claim 2, being packaged in a packaging material and identified in print, in or on said packaging material, for use in the slowing or reversing the progression of a medical condition in which modulating an NO level is beneficial.

4. The pharmaceutical composition of claim 3, wherein said modulating comprises elevating said NO level.

\* \* \* \* \*